(12) United States Patent
Bar-Zion et al.

(10) Patent No.: US 11,446,523 B2
(45) Date of Patent: Sep. 20, 2022

(54) COMPOSITIONS, METHODS AND SYSTEMS FOR GAS VESICLE BASED CAVITATION

(71) Applicant: California Institute of Technology, Pasadena, CA (US)

(72) Inventors: Avinoam D. Bar-Zion, Pasadena, CA (US); Atousa Nourmahnad, Villanova, PA (US); David Maresca, Pasadena, CA (US); Mikhail Shapiro, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 167 days.

(21) Appl. No.: 16/833,637

(22) Filed: Mar. 29, 2020

(65) Prior Publication Data

US 2020/0306564 A1 Oct. 1, 2020

Related U.S. Application Data

(60) Provisional application No. 62/825,612, filed on Mar. 28, 2019, provisional application No. 62/895,553, filed on Sep. 4, 2019.

(51) Int. Cl.
*A61N 7/00* (2006.01)

(52) U.S. Cl.
CPC ........ *A61N 7/00* (2013.01); *A61N 2007/0004* (2013.01); *A61N 2007/0039* (2013.01);
(Continued)

(58) Field of Classification Search
CPC ............. A61N 7/00; A61N 2007/0004; A61N 2007/0039; A61N 2007/0052;
(Continued)

(56) References Cited

U.S. PATENT DOCUMENTS 5,558,092 A * 9/1996 Unger ................. A61B 8/0833
                                                                                                                                  601/3
5,824,309 A 10/1998 Dassarma et al.
(Continued)

FOREIGN PATENT DOCUMENTS

CN        105232045 A     1/2016
EP         3908656 A1    11/2021
(Continued)

OTHER PUBLICATIONS

EPO Communication pursuantto Rules 161(2) and 162 EPC for EP Application No. 20739042 filed on Jul. 14, 2021 on behalfof California Institute of Technology dated Aug. 18, 2021 3 pages.
(Continued)

*Primary Examiner* — Hien N Nguyen
(74) *Attorney, Agent, or Firm* — Steinfl + Bruno, LLP

(57) ABSTRACT

The system and process of therapeutic and effective cavitation by using ultrasound to collapse gas vesicles as well as cavitate the bubbles produced from the collapsed gas vesicles. Therapeutic effect includes, but is not limited to lysing cells by cavitation. The cells expressing the gas vesicles can optionally be used as delivery cells to preform tasks such as transporting the gas vesicles into deep tissue areas, releasing compounds at the cavitation site, and more. The gas vesicles can optionally be modified to facilitate getting the bubbles near the cavitation targets by functionalizing the gas vesicles.

27 Claims, 28 Drawing Sheets

(52) U.S. Cl.
CPC ............... *A61N 2007/0052* (2013.01); *A61N 2007/0082* (2013.01)

(58) Field of Classification Search
CPC ..... A61N 2007/0082; A61B 2090/374; A61M 37/0092
See application file for complete search history.

(56) References Cited

U.S. PATENT DOCUMENTS

| | | | |
|---|---|---|---|
| 7,498,024 | B2 | 3/2009 | Fang et al. |
| 9,107,949 | B2 | 8/2015 | Ju |
| 10,493,172 | B2 | 12/2019 | Lakshmanan et al. |
| 10,955,496 | B2 | 3/2021 | Lu et al. |
| 11,118,210 | B2 | 9/2021 | Bourdeau et al. |
| 2002/0115717 | A1* | 8/2002 | Gervais ............... A61K 51/088 514/553 |
| 2003/0147812 | A1 | 8/2003 | Ueberle |
| 2003/0157025 | A1 | 8/2003 | Unger et al. |
| 2004/0204922 | A1 | 10/2004 | Beadle et al. |
| 2004/0265393 | A1* | 12/2004 | Unger ............... A61K 49/1812 424/600 |
| 2005/0058605 | A1 | 3/2005 | Schneider et al. |
| 2006/0025683 | A1* | 2/2006 | Hoffmann ............... A61B 8/08 600/439 |
| 2006/0058618 | A1 | 3/2006 | Nishiura |
| 2006/0216810 | A1 | 9/2006 | Ju |
| 2010/0069757 | A1 | 3/2010 | Yoshikawa et al. |
| 2010/0239170 | A1 | 9/2010 | Asnis |
| 2012/0020878 | A1* | 1/2012 | Qi ............... C07K 14/475 424/9.4 |
| 2014/0288411 | A1 | 9/2014 | Shapiro et al. |
| 2014/0288412 | A1 | 9/2014 | Schwartz |
| 2014/0288421 | A1 | 9/2014 | Shapiro et al. |
| 2016/0220672 | A1 | 8/2016 | Chalasani et al. |
| 2018/0028693 | A1 | 2/2018 | Lakshmanan et al. |
| 2018/0030501 | A1 | 2/2018 | Bourdeau et al. |
| 2018/0038922 | A1 | 2/2018 | Lu et al. |
| 2020/0164095 | A1 | 5/2020 | Lakshmanan et al. |
| 2020/0237346 | A1 | 7/2020 | Sawyer et al. |
| 2020/0291409 | A1 | 9/2020 | Farhadi et al. |
| 2020/0306564 | A1 | 10/2020 | Bar-Zion et al. |
| 2021/0060185 | A1 | 3/2021 | Lakshman et al. |
| 2021/0301298 | A1 | 9/2021 | Bourdeau et al. |

FOREIGN PATENT DOCUMENTS

| | | |
|---|---|---|
| WO | 2007/014162 A2 | 2/2007 |
| WO | 2012/038950 A1 | 3/2012 |
| WO | 2018/069788 A1 | 4/2018 |
| WO | 2020/146367 A1 | 7/2020 |
| WO | 2020/146379 A1 | 7/2020 |
| WO | 2021/041934 A1 | 3/2021 |

OTHER PUBLICATIONS

Non-Final Office Action for U.S. Appl. No. 16/656,417, filed Oct. 17, 2019 on behalf of California Institute of Technology dated Mar. 23, 2021 20 pages.

Non-Final Office Action for U.S. Appl. No. 16/736,581, filed Jan. 7, 2020, on behalf of California Institute of Technology, dated Aug. 6, 2021. 62 Pages.

Notice of Allowance for U.S. Appl. No. 15/663,635, filed Jul. 28, 2017, on behalf of California Institute of Technology, dated May 27, 2021. 10 pages.

Notice of Allowance for U.S. Appl. No. 16/656,417, filed Oct. 17, 2019, on behalf of California Institute of Technology, dated Sep. 3, 2021. 9 Pages.

Restriction Requirement for U.S. Appl. No. 16/736,683, filed Jan. 7, 2020 on behalf of California Institute of Technology dated Sep. 14, 2021 8 pages.

Lakshmanan A. et al., "Acoustic biosensor for ultrasound imaging of enzyme activity" Nature Chemical Biology, Jul. 2020, 23 pages.

Lakshmanan A. et al., "Acoustic biosensor for ultrasound imaging of enzyme activity (Supplementary Information)" Nature Chemical Biology, Jul. 2020, 3 pages.

Restriction Reguirement for U.S. Appl. No. 15/613,104, filed Jun. 2, 2017 on behalf of California Institute of Technology, dated Feb. 21, 2019. 9 pages.

Smith-Bindman, R., et al., "Use of diagnostic imaging studies and associated radiation exposure for patients enrolled in large integrated health care systems", 1996-2010. JAMA, 2012. 307(22): p. 2400-9.

International Search Report and Written Opinion for PCT App. No. PCT/US2020/048572 filed on Aug. 28, 2020, on behalf of California Institute of Technology, dated Dec. 29, 2020. 11 Pages.

Notice of Allowance for U.S. Appl. No. 15/663,600, filed Jul. 28, 2017 on behalf of California Institute of Technology, dated Dec. 11, 2020.13 Pages.

Notice of Allowance for U.S. Appl. No. 15/663,635, filed Jul. 28, 2017 on behalf of California Institute of Technology dated Jan. 26, 2021 15 pages.

Abdul Rahman, H.S., et al., "Fast and robust three-dimensional best path phase unwrapping algorithm". Applied Optics, 2007. 46(26): p. 6623-6635.

Aguilera et al., "Systemic in vivo distribution of activatable cell penetrating peptides is superior to cell penetrating peptides." Integr Biol (Camb). 2009. 1(5-6): p. 371-381. 22 pages.

Ahrens, E.T. et al., "Tracking immune cells in vivo using magnetic resonance imaging". Nature Reviews: Immunology, 2013. 13(10): p. 755-763. 19 pages.

Altschul, et al., Gapped BLAST and PSI-BLAST: a new generation of protein database search programs. Nucleic Acids Res., 1997. 25(17): 3389-3402. p. 14.

Archer, E.J., et al., "Engineered *E. coli* that detect and respond to gut inflammation through nitric oxide sensing". ACS synthetic biology, 2012. 1(10): p. 451-457.

Atanasijevic, T., et al., "Calcium-sensitive MRI contrast agents based on superparamagnetic iron oxide nanoparticles and calmodulin". Proceedings of the National Academy of Sciences, 2006. 103(40): p. 14707-14712.

Baker, T.A. et al., "ClpXP, an ATP-powered unfolding and protein-degradation machine." Biochimica et Biophysica Acta (BBA)-Molecular Cell Research, 2012. 1823(1): p. 15-28. 33 pages.

Barrett, T. et al., "MRI of Tumor Angiogenesis", Journal of Magnetic Resonance Imaging 26, pp. 235-249, (2007), 15 pages.

Bar-Zion, A. et al. Acoustically Detonated Biomolecules for Genetically Encodable Inertial Cavitation. bioRxiv 620567 (2019) 11 pages.

Beard, P. "Biomedical photoacoustic imaging." *Interface Focus*1, 602-631(2011).

Belkaid, Y. et al., "Role of the microbiota in immunity and inflammation". Cell, 2014. 157(1): p. 121-141.

Blanco, E., et al., "Principles of nanoparticle design for overcoming biological barriers to drug delivery". Nature biotechnology, 2015. 33(9): p. 941-951.

Blum-Oehler, G., et al., "Development of strain-specific PCR reactions for the detection of the probiotic *Escherichia coli* strain Nissle 1917 in fecal samples." Research in Microbiology, 2002. 154(1): p. 59-66.

Bourdeau, R.W., et al., "Acoustic Reporter Genes for Non-lnvasive Imaging of Microorganisms in Mammalian Hosts." Nature 553, 86-90, (Jan. 2018). 19 pages.

Bowen, C.V., et al., Application of the static dephasing regime theory to superparamagnetic iron-oxide loaded cells. Magnetic Resonance in Medicine, 2002. 48(1): p. 52-61.

Braat, H., et al., "A phase I trial with transgenic bacteria expressing interleukin-10 in Crohn's disease". Clinical gastroenterology and hepatology, 2006. 4(6): p. 754-759.

Brock, R., "The uptake of arginine-rich cell-penetrating peptides: putting the puzzle Together". Bioconjugate chemistry, 2014. 25(5): p. 863-868.

Brooks, et al., "On T2-shortening by weakly magnetized particles: The chemical exchange model". Magnetic Resonance in Medicine, 2001. 45(6): p. 1014-1020.

(56) References Cited

OTHER PUBLICATIONS

Buchholz, B., et al., "The distribution of the outer gas vesicle protein, GvpC, on the Anabaena gas vesicle, and its ratio to GvpA". Microbiology, 1993. 139(10): p. 2353-2363.

Buchler, et al., "On schemes of combinatorial transcription logic", Proceedings of the National Academy of Sciences, 2003. 100(9): p. 5136-5141.

Burns, P.N., "Harmonic imaging with ultrasound contrast agents". Clin. Radiol., 1996. 51: p. 50-55.

Caldwell et al. "A *Zoogloea* sp. associated with blooms of Anabaena flosaquae" Canadian Journal of Microbiology, NRC Research Press. Aug. 1978. vol. 24, No. 8. pp 922-931. (Abstract Only) 2 pages.

Calvo, et al, Upstream open reading frames cause widespread reduction of protein expression and are polymorphic among humans. Proc Natl Acad Sci U S A, 2009. 106(18): p. 7507-12.

Cameron, D.E. and Collins, J.J., "Tunable protein degradation in bacteria." Nature Biotechnology 2014. 32 (12): p. 1276-1281. 19 pages.

Caravan, P., et al., "Gadolinium(III) Chelates as MRI Contrast Agents: Structure, Dynamics, and Applications", Chemical Reviews, 1999. 99(9): p. 2293-2352.

Cha-Molstad et al., "Modulation of SQSTM1/p62 activity by N-terminal arginylation of the endoplasmic reticulum chaperone HSPA5/GRP78/BiP." Autophagy, 2016. 12(2): p. 426-428.

Chassin H. et al., "A modular degron library for synthetic circuits in mammalian cells." Nature Communications 2019. 10: 2013. 11 pages.

Cherin, E., et al., "Acoustic Behavior of Halobacterium salinarum Gas Vesicles in the High-Frequency Range: Experiments and Modeling". Ultrasound in Medicine & Biology, 2017. 43(5): p. 1016-1030. 33 pages.

Choi, J.J., et al., Noninvasive, transcranial and localized opening of the blood-brain barrier using focused ultrasound in mice. Ultrasound in Medicine & Biology, 2007. 33(1): p. 95-104.

Chu, et al., "A bright cyan-excitable orange fluorescent protein facilitates dual-emission microscopy and enhances bioluminescence imaging in vivo". Nat Biotech 34 (7), 760-767 (2016). 29 pages.

Church C. "Frequency, pulse length, and the mechanical index." *Acoustics Research Letters Online,* 6(3), 162-168, 8 pages(2005).

Claesen, J., et al., "Synthetic microbes as drug delivery systems". ACS synthetic biology, 2014. 4(4): p. 358-364.

Cohen, B., et al., "Ferritin as an Endogenous MRI Reporter for Noninvasive Imaging of Gene Expression in C6 Glioma Tumors". Neoplasia, 2005. 7(2): p. 109-117.

Cohen, B., et al., "MRI detection of transcriptional regulation of gene expression in transgenic mice". Nat Med, 2007. 13(4): p. 498-503.

Corrected Notice of Allowability for U.S. Appl. No. 15/613,104, filed Jun. 2, 2017 on behalf of California Institute of Technology dated Sep. 9, 2019 10 pages.

Cosgrove, D., et al., "Clinical Uses of Microbubbles in Diagnosis and Treatment." Med. Biol. Eng. Comput. 47, 813-826, (2009), 14 pages.

Courbet, A., et al., "Detection of pathological biomarkers in human clinical samples via amplifying geneticswitches and logic gates". Science translational medicine, 2015. 7(289): p. 289ra83-289ra83. 49 pages Abstract Only.

Coussios, C. et al., "Applications of Acoustics and Cavitation to Noninvasive Therapy and Drug Delivery." *Annu. Rev. Fluid Meeh.* (2008) 40, 395-420. 28 pages.

Cunningham, C.H., et al., "Positive contrast magnetic resonance imaging of cells labeled with magnetic nanoparticles". Magnetic Resonance in Medicine, 2005. 53(5): p. 999-1005.

Dang, L. H. et al., "Combination bacteriolytic therapy for the treatment of experimental tumors." *Proc. Natl. Acad. Sci. U. S. A.* 98, 26, 15155-60(2001).

Daniel, C., et al., "Bioluminescence imaging study of spatial and temporal persistence of Lactobacillus plantarum and Lactococcus lactis in living mice". Applied and environmental microbiology, 2013. 79(4): p. 1086-1094.

Daniel, C., et al., "Recombinant lactic acid bacteria as mucosal biotherapeutic agents". Trends in biotechnology, 2011. 29(10): p. 499-508.

Danino, T., et al., "In vivo gene expression dynamics of tumor-targeted bacteria". ACS synthetic biology, 2012. 1(10): p. 465-470.

Danino, T., et al., "Programmable probiotics for detection of cancer in urine". Science translational medicine, 2015. 7(289): p. 289ra84-289ra84. 28 pages.

Dassarma, et al.,"An improved genetic system for bioengineering buoyant gas vesicle nanoparticles from Haloarchaea". BMC Biotechnol. 2013, 13, 112. 10 pgs.

Dassarma, P., et al., "Bioengineering Novel Floating Nanoparticles for Protein and Drug Delivery." Materials Today: Proceedings: Advances in Functional Materials (Conference 2015), 3(2), 206-210, (2016). 8 pages.

Datsenko, K.A. et al., "One-step inactivation of chromosomal genes in *Escherichia coli* K-12 using PCR products." Proceedings of the National Academy of Sciences, 2000. 97(12): p. 6640-6645.

Davila, M. L. et al. "Efficacy and Toxicity Management of 19-28z CAR T Cell Therapy in B Cell Acute Lymphoblastic Leukemia". 6(224), *Sci Transl Med*(2014). 23 pages.

Dawson, P.E., et al., "Synthesis of proteins by native chemical ligation". Science, 1994. 266 (5186): p. 776-779.

Del Vecchio, D and Muarray, R.M. "Biomolecular Feedback Systems" bfs-pupss. Jun. 13, 2014. 280 pages.

Derrien, M., et al., "Fate, activity, and impact of ingested bacteria within the human gut microbiota". Trends in microbiology, vol. 23, No. 6, 2015, pp. 354-366.

Din, M.O., et al., "Synchronized cycles of bacterial lysis for in vivo delivery". Nature, 2016. 536(7614): p. 81-85. 18 pages.

Donaldson, G.P., et al., "Gut biogeography of the bacterial microbiota". Nature Reviews Microbiology, vol. 14, 2016, pp. 20-32.

Drag, M. et al., "Emerging principles in protease-based drug discovery." Nature Reviews Drug Discovery 9 (9), 690-701, (2010). 27 pages.

Elowitz, M.B. and S. Leibler, A synthetic oscillatory network of transcriptional regulators. Nature, 2000. 403(6767): p. 335-338.

Errico, C., et al., "Ultrafast ultrasound localization microscopy for deep super-resolution vascular imaging". Nature, 2015. 527(7579): p. 499-502. 9 pages.

Evbuomwan, O.M., et al., "CEST and PARACEST Agents for Molecular Imaging, in the Chemistry of Molecular Imaging". 2015, John Wiley & Sons, Inc. p. 225-243.

Farhadi, A., et al., Recombinantly Expressed Gas Vesicles as Nanoscale Contrast Agents for Ultrasound and Hyperpolarized MRI. AIChE J, 2018. 64(8): p. 2927-2933. 20 pages.

Farhadi A. et al., "Ultrasound imaging of gene expression in mammalian cells" Science 365, 1469-1475, Sep. 2019, 43 pages.

Fernandez-Rodriguez, J. et al., "Post-translational control of genetic circuits using Potyvirus proteases." Nucleic Acids Research 44, No. 13, 6493-6502 (2016).

Ferrara, K., et al., "Ultrasound Microbubble Contrast Agents: Fundamentals and Application to Gene and Drug Delivery." Annu. Rev. Biomed. Eng. 9, 415-447, (2007). 35 pages.

Final Office Action for U.S. Appl. No. 15/663,635, filed Jul. 28, 2017 on behalf of California Institute of Technology dated Oct. 24, 2019 27 pages.

Fischbach, M.A., et al., "Cell-based therapeutics: the next pillar of medicine". Science translational medicine, 2013. 5(179): p. 179ps7-179ps7. 7 pages.

Fischer, et al., "Average protein density is a molecular-weight-dependent function". Protein Science, 2004. 13(10): p. 2825-2828.

Forbes N. S., et al., "Sparse initial entrapment of systemically injected *Salmonella typhimurium* leads to heterogeneous accumulation within tumors." Cancer Res. 63, 5188-5193(2003).

Foster, et al., "Advances in ultrasound biomicroscopy". Ultrasound in medicine & biology 26, 1-27 (2000).

Foster, F.S., et al., "Principles and applications of ultrasound backscatter microscopy". Ultrasonics, Ferroelectrics and Frequency Control, IEEE Transactions on, 1993. 40(5): p. 608-617.

Foucault, M.-L., et al., "In vivo bioluminescence imaging for the study of intestinal colonization by *Escherichia coli* in mice". Applied and environmental microbiology, 2010. 76(1): p. 264-274.

(56) References Cited

OTHER PUBLICATIONS

Gao, X.J. et al., "Programmable protein circuits in living cells." Science 361, 1252-1258 (2018).
Gardner, T.S. et al., "Construction of a genetic toggle switch in *Escherichia coli*." Nature, 2000. 403(6767): p. 339-342.
Genove, G., et al., "A new transgene reporter for in vivo magnetic resonance imaging". Nat Med, 2005. 11(4): p. 450-454.
Geva-Zatorsky, N., et al., "In vivo imaging and tracking of host-microbiota interactions via metabolic labeling of gut anaerobic bacteria." Nature Medicine, 2015. 21(9): p. 1091-1100. 27 pages.
Gilad, A.A., et al., "Artificial reporter gene providing MRI contrast based on proton exchange". Nat Biotech, 2007. 25(2): p. 217-219.
Gilad, A.A., et al., "Developing MR reporter genes: promises and pitfalls". NMR in Biomedicine, 2007. 20(3): p. 275-290.
Gilad, A.A., et al., "MRI Reporter Genes". Journal of Nuclear Medicine, 2008. 49(12): p. 1905-1908.
Gillis, et al., "On T2-shortening by strongly magnetized spheres: A partial refocusing model". Magnetic Resonance in Medicine, 2002. 47(2): p. 257-263.
Gillis, et al., "Transverse relaxation of solvent protons induced by magnetized spheres: Application to ferritin, erythrocytes, and magnetite". Magnetic Resonance in Medicine, 1987. 5(4): p. 323-345.
Goll, D.E., et al., "The calpain system." Physiological Reviews, 2003. 83(3): p. 731-801.
Gorbach, S.L., "Chapter 95: Microbiology of the Gastrointestinal Tract", Medical Microbiology, 4th Edition, Editor: Samuel Baron, University of Texas Medical Branch at Galveston, Galveston, TX (1996). 10 pages.
Griffiths, et al., "The homologies of gas vesicle proteins", Journal of General Microbiology (1992), 138, 1243-1250.
Haacke, E.M. et al., "Susceptibility-Weighted Imaging: Technical Aspects and Clinical Applications," Part 1. American Journal of Neuroradiology 30 (1), pp. 19-30, (Jan. 2009), 29 pages.
Hayes, et al., "Complete amino acid sequence of cyanobacterial gas-vesicle protein indicates a 70-residue molecule that corresponds in size to the crystallographic unit cell". Biochemical Journal, 1986. 236(1): p. 31-36.
Hayes, et al., "The gvpA/C cluster of Anabaena flos-aquae has multiple copies of a gene encoding GvpA", Archives of microbiology, 1995. 164(1): p. 50-57.
Hayes, P., et al., "Gas vesicles are strengthened by the outer-surface protein, GvpC". Archives of microbiology, 1992. 157(3): p. 229-234.
Häcker, G. et al., "Activation of the immune system by bacterial CpG-DNA." *Immunology* 105, 245-251 (2002).
He, et al, "Biophysical mechanisms of phase contrast in gradient echo MRI". Proceedings of the National Academy of Sciences, 2009. 106(32): p. 13558-13563.
Heim, R. et al., "Engineering green fluorescent protein for improved brightness, longer wavelengths and fluorescence resonance energy transfer." Current Biology 6, 178-182 (1996).
Holland C. et al., "An Improved Theory for the Prediction of Microcavitation Thresholds." vol. 36, No. 2, 204-208 IEEE (1989).
Huang, H. et al. "A G-Quadruplex-Containing RNA Activates Flourescence in a GFP-Like Flourophore", Nat Chem Biol., Aug. 2014, 10 (8); 686-691. 22 pages.
Hung, A.H., et al., "Magnetic Barcode Imaging for Contrast Agents." Magnetic Resonance in Medicine, 77(3), 970-978, (2017). 9 pages.
International Search Report and Written Opinion for PCT App. No. PCT/US2020/025608 filed on Mar. 29, 2020 on behalf of California Institute of Technology, dated Jul. 17, 2020. 13 Pages.
International Search Report for International Application No. PCT/US2020/012557 filed on Jan. 7, 2020 on behalf of California Institute of Technology dated May 1, 2020 5 pages.
International Search Report for International Application No. PCT/US2020/012572 filed on Jan. 7, 2020 on behalf of California Institute of Technology dated May 6, 2020 4 pages.
Jackson, H. J. et al., "Driving CAR T-cells forward." *Nat. Rev. Clin. Oncl.* 13 (6), 370-383(2016). 31 pages.
Jaffer, F.A. et al., "Molecular and Cellular Imaging of Atherosclerosis", Emerging Applications. Journal of the American College of Cardiology, vol. 47, No. 7, pp. 1328-1338, (2006), 11 pages.
Jang, M. J. et al., "NeuroCa: integrated framework for systematic analysis of spatiotemporal neuronal activity patterns from large-scale optical recording data." *Neurophotonics* 2(3), 035003(2015). 16 pages.
Jensen, et al., "NMR relaxation in tissues with weak magnetic inhomogeneities". Magnetic Resonance in Medicine, 2000. 44(1): p. 144-156.
Jolesz, F.A., "MRI-Guided Focused Ultrasound Surgery". Annual Review of Medicine, 2009. 60(1): p. 417-430. 17 pages.
Karlin, et al., "Applications and statistics for multiple high-scoring segments in molecular sequences",. Proceedings of the National Academy of Sciences, 1993. 90(12): p. 5873-5877.
Karlin, et al., "Methods for assessing the statistical significance of molecular sequence features by using general scoring schemes", Proceedings of the National Academy of Sciences, 1990. 87(6): p. 2264-2268.
Kaufmann, B.A., et al., "Molecular Imaging with Targeted Contrast Ultrasound." Current Opinion in Biotechnology 18(1), 11-16, (2007). 6 pages.
Khalil, A.S. et al., "Synthetic biology: applications come of age." Nature Reviews Genetics, 2010. 11(5): p. 367-379.
Kinsman, et al., "Genes encoding proteins homologous to halobacterial Gvps N, J, K, F & L are located downstream of gvpC in the cyanobacterium Anabaena flos-aquae", DNA Sequence, 1997. 7(2): p. 97-106.
Kinsman, R., et al., "GvpCs with reduced numbers of repeating sequence elements bind to and strengthen cyanobacterial gas vesicles". Molecular microbiology, 1995. 17(1): p. 147-154.
Kislukhin, A.A., et al., "Paramagnetic fluorinated nanoemulsions for sensitive cellular fluorine-19 magnetic resonance imaging". Nat Mater, 2016. 15(6): 662-668. 19 pages.
Klumpp, S., et al., "Bacterial growth: global effects on gene expression, growth feedback and proteome partition". Current opinion in biotechnology, 2014. 28: p. 96-102.
Koehne G. et al., "Serial in vivo imaging of the targeted migration of human HSV-TK-transduced antigen-specific lymphocytes." *Nature Biotechnology* vol. 21, 405-413(Apr. 2003).
Kotula, J.W., et al., "Programmable bacteria detect and record an environmental signal in the mammalian gut". Proceedings of the National Academy of Sciences, 2014. 111(13): p. 4838-4843.
Kunth, M. et al., "Protein Nanostructures Produce Self-Adjusting Hyperpolarized Magnetic Resonance Imaging Contrast through Physical Gas Partitioning." *ACS Nano*(2018). 12, 10939-10948. doi:10.1021/acsnano.8b04222.
Kwan, J. J. et al. "Ultrasound-Propelled Nanocups for Drug Delivery." *Small Journal* 11, No. 39, 5305-5314 (2015).
Lakshmanan, A., et al., "Molecular Engineering of Acoustic Protein Nanostructures". ACS Nano, 2016. 10(8): p. 7314-7322.
Lakshmanan, A., et al., Preparation of biogenic gas vesicle nanostructures for use as contrast agents for ultrasound and MRI. Nat Protoc, 2017. 12(10): p. 2050-2080.
Lakshmanan, et al., "Acoustic biosensors for ultrasound imaging of enzyme activity," Supplementary Information in Nature Chemical Biology. Jul. 13, 2020. 2 Pages.
Lakshmanan,A et al., "Acoustic Biosensors for Ultrasound Imaging of Enzyme Activity", Nature Chemical Biology, 16, pp. 988-996 (Jul. 13, 2020), 23 pages.
Lecoq, J. et al., "An Infrared Fluorescent Protein for Deeper Imaging", Nat Biotech, vol. 29, No. 8, pp. 715-716 (2011), 2 pages.
Lee, J.-H., et al., "Artificially engineered magnetic nanoparticles for ultra-sensitive molecular imaging", Nat Med, 2007. 13(1): p. 95-99.
Li, et al., "Gas vesicle genes identified in Bacillus megaterium and functional expression in *Escherichia coli*", J Bacteriol, 1998. 180(9): p. 2450-8.
Li, Z. et al., "Comparison of Reporter Gene and Iron Particle Labeling for Tracking Fate of Human Embryonic Stem Cells and Differentiated Endothelial Cells in Living Subjects", Stem Cells 26 (4), pp. 864-873, (2008), 21 pages.
Lin, M.Z. et al., "Genetically encoded indicators of neuronal activity." Nature Neuroscience 19, No. 9, 1142-1153 (2016).

(56) References Cited

OTHER PUBLICATIONS

Lopez-Otin, C et al., "Proteases: multifunctional enzymes in life and disease." Journal of Biological Chemistry 283, No. 45, 30433-7 (2008).
Lu, G.J., et al., Acoustically modulated magnetic resonance imaging of gas-filled protein nanostructures. Nat Mater, 2018. 17(5): p. 456-463. 15 pages.
Machtaler, S., et al., "Assessment of inflammation in an acute on chronic model of inflammatory bowel disease with ultrasound molecular imaging." Theranostics, 2015. 5(11): p. 1175-1186.
Mani, V., et al., "GRadient echo Acquisition for Superparamagnetic particles with Positive contrast (GRASP): Sequence Characterization in Membrane and Glass Superparamagnetic Iron Oxide Phantoms at 1.5T and 3T". Magnetic Resonance in Medicine, 2006. 55(1): p. 126-135.
Maresca D, et al ., "Nonlinear X-Wave Ultrasound Imaging of Acoustic Biomolecules" *Phys Rev X*vol. 8,(2018). 041002-1 to 041002-12. 12 pages.
Maresca D, et al., "Biomolecular Ultrasound and Sonogenetics" *Annu Rev Chem Biomol Eng*vol. 9, 229-252(Jun. 2018). 29 pages.
Maresca, D., et al., "Imaging microvasculature with contrast-enhanced ultraharmonic Ultrasound". Ultrasound in medicine & biology, 2014. 40(6): p. 1318-1328.
Maresca, D., et al., "Nonlinear Ultrasound Imaging of Nanoscale Acoustic Biomolecules". Applied Physics Letters, 2017. 110(7), 073704-1 to 073704-5. 6 pages.
Mark Welch, J.L., et al., "Spatial organization of a model 15-member human gut microbiota established in gnotobiotic mice." Proceedings of the National Academy of Sciences, 2017. 114(43): p. E9105-E9114.
Matsumoto, et al., "T2 relaxation induced by clusters of superparamagnetic nanoparticles: Monte Carlo simulations". Magnetic Resonance Imaging, 2008. 26(7): p. 994-998.
McMahon, M.T., et al., "New "multicolor" polypeptide diamagnetic chemical exchange saturation transfer (DIACEST) contrast agents for MRI". Magnetic Resonance in Medicine, 2008. 60(4): p. 803-812.
Meeker, D., Finite element method magnetics. FEMM, 2015. 4: p. 32. 162 pages.
Milenic D. E. et al., "Antibody-Targeted Radiation Cancer Therapy." *Nature*3,(2004). 488-498.
Milo, R., et al., "BioNumbers—the database of key numbers in molecular and cell biology". Nucleic Acids Research, 2010. 38(suppl 1): p. D750-D753.
Mitra, R.D. et al., "Fluorescence resonance energy transfer between blue emitting and red-shifted excitation derivatives of the green fluorescent protein." Gene 173, 13-17 (1996).
Miyawaki, A. et al., "Molecular spies for bioimaging-fluorescent protein-based probes." Molecular Cell 58, 632-643 (2015).
Mowat, A.M., et al., "Regional specialization within the intestinal immune system". Nature Reviews Immunology, vol. 14, 2014, 667-685.
Muradali, D. et al., "US of gastrointestinal tract disease." Radiographics, 2015. 35(1): p. 50-68.
Myers, et al., "Optimal alignments in linear space", Computer applications in the biosciences: CABIOS, 1988. 4(1): p. 11-17.
Natarajan, S, "NS3 protease from flavivirus as a target for designing antiviral inhibitors against dengue virus", Genetics and Molecular Biology, 33, 2, 214-219 (2010).
Needleman, et al., "A general method applicable to the search for similarities in the amino acid sequence of two proteins", Journal of molecular biology, 1970. 48(3): p. 443-453.
Ngamdee et al. "Competition between Burkholderia pseudomallei and B. thailandesis" *BMC Microbiology, BioMed Central.*2015. vol. 15, No. 56. 15 pages.
Nilsson, B.L., et al., "Chemical synthesis of proteins". Annu. Rev. Biophys. Biomol. Struct., 2005. 34: p. 91-118. 38 pages.
Non-Final Office Action for U.S. Appl. No. 15/663,600, filed Jul. 28, 2017 on behalf of California Institute of Technology, dated Jun. 23, 2020. 26 pages.

Non-Final Office Action for U.S. Appl. No. 15/663,635, filed Jul. 28, 2017, on behalf of California Institute of Technology, dated Jan. 2, 2019. 29 pages.
Non-Final Office Action for U.S. Appl. No. 15/663,635, filed Jul. 28, 2017 on behalf of California Institute of Technology dated May 29, 2020 24 pages.
Notice of Allowance for U.S. Appl. No. 15/613,104, filed Jun. 2, 2017 on behalf of California Institute of Technology dated Jul. 18, 2019 15 pages.
Ntziachristos, V., et al., "Looking and Listening to Light: the Evolution of Whole-Body Photonic Imaging." Nature Biotechnology, 23(3), 313-320, (2005). 8 pages.
Ntziachristos, V. "Going deeper than microscopy: the optical imaging frontier in biology." *Nature Methods*7, No. 8, 603-614 (2010).
Ong, I.L.H. et al., "Recent developments in protease activity assays and sensors." Analyst 142, 1867-1881 (2017).
Ono, Y. et al., "Calpain research fordrug discovery: challenges and potential." Nature Reviews Drug Discovery, 2016. 15(12): p. 854-876. 34 pages.
Ono, Y. et al., "Calpains—an elaborate proteolytic system." Biochimica et Biophysica Acta (BBA)-Proteins and Proteomics, 2012. 1824(1): p. 224-236.
Palmer, A.E. et al., "Design and application of genetically encoded biosensors." Trends in Biotechnology 29 (3), 144-152 (2011). 18 pages.
Parks, T.D., et al., "Release of proteins and peptides from fusion proteins using a recombinant plant virus proteinase." Analytical Biochemistry, 1994. 216(2): p. 413-417.
Pearson, et al., "Improved tools for biological sequence comparison", Proceedings of the National Academy of Sciences, 1988. 85(8): p. 2444-2448.
Perez, J.M., et al., "Magnetic relaxation switches capable of sensing molecular interactions". Nat Biotech, 2002. 20(8): p. 816-820.
Pfeifer, Felicitas. "Distribution, formation and regulation of gas vesicles" *Nature Reviews—Microbiology, Macmillan Publishers Ltd.*Oct. 2012. vol. 10. pp 705-715. 11 pages.
Phan, J., et al., "Structural basis for the substrate specificity of tobacco etch virus protease." Journal of Biological Chemistry, 2002. 277(52): p. 50564-50572.
Piraner, D. I. et al. Going Deeper: Biomolecular Tools for Acoustic and Magnetic Imaging and Control of Cellular Function. Biochemistry 56, 5202-5209 (2017).
Puderbach, M. et al. "MR Imaging of the Chest: A Practical Approach at 1.5 T." European Journal of Radiology 64, 345-355, (2007). 13 pages.
Purnick, P.E. and R. Weiss, "The second wave of synthetic biology: from modules to systems." *Nat Rev Mol Cell Biol*,2009. 10(6): p. 410-22.
Qin et al. "Bacterial abundance and diversity in pond water supplied with different feeds" *Nature—Scientific Reports, Nature Publishing Group.*Oct. 19, 2016. vol. 6, No. 35232. pp 1-13. 13 pages.
Ramnarine, et al., "Construction and geometric stability of physiological flow rate wall-less stenosis phantoms." *Ultrasound in medicine & biology*27, No. 2, 245-250 (2001).
Ramsay, J.P., et al., "A quorum-sensing molecule acts as a morphogen controlling gas vesicle organelle biogenesis and adaptive flotation in an enterobacterium." *Proc Natl Acad Sci U S A*,2011. 108(36): p. 14932-7.
Reits, E.A., et al., "From fixed to FRAP: measuring protein mobility and activity in living cells". Nature cell biology, 2001. 3(6): p. E145-E147.
Restriction Requirement for U.S. Appl. No. 15/663,600, filed Jul. 28, 2017 on behalf of California Institute of Technology, dated Dec. 27, 2019. 7 pages.
Rodriguez, E.A. et al. "The growing and glowing toolbox of fluorescent and photoactive proteins." Trends in Biochemical Sciences 42 (2), 111-129 (2017). 31 pages.
Rodriguez, P.L., et al., "Minimal"Self" peptides that inhibit phagocytic clearance and enhance delivery of nanoparticles". Science, 2013. 339(6122): p. 971-975. 11 pages.
Romero, P.A., et al., "Exploring protein fitness landscapes by directed evolution". Nature Reviews Molecular Cell Biology, 2009. 10(12): p. 866-876. 25 pages.

(56) References Cited

OTHER PUBLICATIONS

Rose, A.B., Intron-mediated regulation of gene expression. Curr Top Microbiol Immunol, 2008. 326: p. 277-90.
Round, J.L. et al., "The gut microbiota shapes intestinal immune responses during health and disease". Nature Reviews Immunology, 2009. 9(5): p. 313-323. 11 pages.
Ruoslahti, E., "RGD and other recognition seguences for integrins". Annual review of cell and developmental biology, 1996. 12(1): p. 697-715. 21 pages.
Ryan, R. M. et al. "Bacterial delivery of a novel cytolysin to hypoxic areas of solid tumors." *Gene Ther.*16, 329-339(2009).
Santos E. B. et al., "Sensitive in vivo imaging of T cells using a membrane-bound Gaussia princeps luciferase", *Nat Med*vol. 15, No. 3, 338-344(Mar. 2009).
Sauer, R.T. and Baker, T.A., "AAA+ Proteases: ATP-Fueled Machines of Protein Destruction." Annual Review of Biochemistry, 2011. 80: p. 587-612.
Sauer, R.T., et al., "Sculpting the proteome with AAA(+) proteases and disassembly machines." Cell, 2004. 119(1): p. 9-18. 21 pages.
Savage, D. C. "Microbial ecology of the gastrointestinal tract." *Annual review of microbiology*31, 107-133 (1977).
Schechter, et al, On the active site of proteases. 3. Mapping the active site of papain; specific peptide inhibitors of papain. Biochem Biophys Res Commun., 1968 32(5): p. 898-902.
Schechter, et al, On the size of the active site in proteases. I. Papain. Biochem Biophys Res Commun., 1967. 27(2): p. 157-162.
Schindelin, J., et al., "Fiji: an open-source platform for biological-image analysis". Nat Meth, 2012. 9(7): p. 676-682. 15 pages.
Schneider, C. et al., "NIH Image to ImageJ: 25 years of image analysis." *Nat. Methods*9(7), 671-675 (2012). 12 pages.
Schweser, F., et al., "Quantitative imaging of intrinsic magnetic tissue properties using MRI signal phase: An approach to in vivo brain iron metabolism?", NeuroImage, 2011. 54(4): p. 2789-2807.
Shaner, N.C., et al., "A bright monomeric green fluorescent protein derived from Branchiostoma lanceolatum". Nat Meth, 2013. 10(5): p. 407-409. 8 pages.
Shaner, N.C., et al., "Improved monomeric red, orange and yellow fluorescent proteins derived from *Discosoma* sp. red fluorescent protein". Nature biotechnology, 2004. 22(12): p. 1567-1572.
Shaner, N.C., et al., "Improving the photostability of bright monomeric orange and red fluorescent proteins". Nature methods, 2008. 5(6): p. 545-551. 25 pages.
Shapiro, M.G., et al., "Biogenic gas nanostructures as ultrasonic molecular reporters". Nature nanotechnology, 2014. 9(4): p. 311-316. 16 pages.
Shapiro, M.G., et al., "Directed evolution of a magnetic resonance imaging contrast agent for noninvasive imaging of dopamine". Nat Biotech, 2010. 28(3): p. 264-270. 15 pages.
Shapiro, M.G., et al., "Genetically encoded reporters for hyperpolarized xenon magnetic resonance imaging". Nat Chem, 2014. 6(7): p. 629-34.
Shapiro, M.G., et al., "Protein Nanoparticles Engineered to Sense Kinase Activity in MRI". Journal of the American Chemical Society, 2009. 131(7): p. 2484-2486. 8 pages.
Silva-Rocha, et al., "Mining logic gates in prokaryotic transcriptional regulation networks", FEBS letters, 2008. 582(8): p. 1237-1244.
Simon, G. L. & Gorbach, S. L. Intestinal flora in health and disease. Gastroenterology 86, 174-193 (1984).
Simon, R.D., "Morphology and Protein Composition of Gas Vesicles from Wild Type and Gas Vacuole Defective Strains of Halobacterium salinarium Strain 5". Microbiology, 1981. 125(1): p. 103-111.
Smith, et al., "Comparison of biosequences", Advances in applied mathematics, 1981. 2(4): p. 482-489.
Smith TF, et al., Identification of common molecular subsequences. J Mol Biol, 1981. 147(1): 195-197. p. 3.
Sonnenborn, U. et al., "The non-pathogenic *Escherichia coli* strain Nissle 1917-features of a versatile probiotic." Microbial Ecology in Health and Disease, 2009. 21(3-4):p. 122-158.
Sprinzak, D., et al., "Reconstruction of genetic circuits". Nature, 2005. 438(7067): p. 443-448.
Sremac, M., et al., "Recombinant Gas Vesicles from *Halobacterium* sp. Displaying SIV Peptides Demonstrate Biotechnology Potential as a Pathogen Peptide Delivery Vehicle", BMC Biotechnology 8(9), (2008). 14 pages.
Srivastava, A.K., et al., "Advances in using MRI probes and sensors for in vivo cell tracking as applied to regenerative medicine". Disease Models and Mechanisms, 2015. 8(4): p. 323-336.
Steidler, L., et al., "Treatment of murine colitis by Lactococcus lactis secreting interleukin-10". Science, 2000. 289(5483): p. 1352-1355.
Stein, V. et al. "Protease-based synthetic sensing and signal amplification." Proceedings of the National Academy of Sciences 111, No. 45, 15934-15939 (2014).
St-Pierre, F., et al., "One-step cloning and chromosomal integration of DNA." ACS synthetic biology, 2013. 2(9): p. 537-541.
Stuber, M., et al., "Positive contrast visualization of iron oxide-labeled stem cells using inversion-recovery with ON-resonant water suppression (IRON)". Magnetic Resonance in Medicine, 2007. 58(5): p. 1072-1077.
Suzuki, S., et al., "Development of an artificial calcium-dependent transcription factor to detect sustained intracellular calcium elevation." ACS Synthetic Biology, 2014. 3(10): p. 717-722.
Szymczak A. L. et al., "Development of 2A peptide-based strategies in the design of multicistronic vectors." *Expert Opin Biol*Th 5 (5), 627-638(2005).
Tang, J., et al., "SWIM: Susceptibility Mapping as a Means to Visualize Veins and Quantify Oxygen Saturation, in Susceptibility Weighted Imaging in MRI". 2011, John Wiley & Sons, Inc. p. 461-485.
Taratula, et al., "Functionalized 129Xe contrast agents for magnetic resonance imaging". Current Opinion in Chemical Biology, 2010. 14(1): p. 97-104. 14 pages.
Tashiro, et al., "Molecular genetic and physical analysis of gas vesicles in buoyant enterobacteria", Environmental microbiology, 2016. 18(4): p. 1264-1276.
Terreno, E., et al., "Challenges for Molecular Magnetic Resonance Imaging". Chemical Reviews, 2010. 110(5): p. 3019-3042.
Tigges, M., et al., "A tunable synthetic mammalian oscillator. Nature," 2009. 457(7227): p. 309-312.
Tsien R. Y., "Imagining imaging's future" *Nature Reviews Molecular Cell Biology*, Ss16-Ss21 (Sep. 2003).
Tsien, R. Y. The Green Fluorescent Protein. Annual Review of Biochemistry 67, 509-544 (1998).
Turk, B., et al., "Protease signaling: the cutting edge." The EMBO Journal 31, 1630-1643 (2012).
Van Keulen, G., et al., "Gas vesicles in actinomycetes: old buoys in novel habitats?", Trends in microbiology, 2005. 13(8): p. 350-354.
Walsby, A. E."Gas Vesicles." *Annu. Rev. Plant Physiol.*26, 427-439 (1975).
Walsby, A. E. "The pressure relationships of gas vacuoles." *Proc. R. Soc. London. Ser. B. Biol. Sci.* 178, 301-326 (1971).
Walsby, A.E., "Cyanobacteria: planktonic gas-vacuolate forms", The Prokaryotes, a Handbook on Habitats, Isolation, and Identification of Bacteria, 2013. 1: p. 224-235.
Walsby, A.E., et al., "The gas-permeability coefficient of the cyanobacterial gas vesicle wall". Journal of General Microbiology, 1992. 138: p. 837-845.
Walsby, A.E., Gas vesicles. Microbiol. Rev., 1994. 58(1): p. 94-144.
Walsby, A.E., "Gas-vacuolate bacteria (apart from cyanobacteria)", in the Prokaryotes. 1981, Springer, p. 441-447.
Walsby, et al., "Average thickness of the gas vesicle wall in Anabaena flos-aquae". Journal of Molecular Biology, 1979. 129(2): p. 279-285.
Walsby, et al., "Gas vesicle proteins". Biochem. J. 1989, 264, 313-322.
Wang, et al., "Quantitative susceptibility mapping (QSM): Decoding MRI data for a tissue magnetic biomarker". Magnetic Resonance in Medicine, 2015. 73(1): p. 82-101.
Wang, Y., et al., "The role of microbiome in central nervous system disorders". Brain, behavior, and immunity, 2014. 38: p. 1-12. 28 pages.

(56) References Cited

OTHER PUBLICATIONS

Watanabe et al. "Distribution and identification of proteolytic *Bacillus* spp. in paddy field soil under rice cultivation" Canadian Journal of Microbiology, NRC Research Press. Jul. 1993. vol. 39. No. 7. pp. 674-680. (Abstract Only) 2 pages.
Weissleder, R., et al., "Ultrasmall superparamagnetic iron oxide: characterization of a new class of contrast agents for MR imaging", Radiology, 1990. 175(2): p. 489-493.
Wells, J.M., et al., "Mucosal delivery of therapeutic and prophylactic molecules using lactic acid bacteria". Nature Reviews Microbiology, 2008. 6(5): p. 349-362.
Woese, C.R., Bacterial evolution. Microbiological reviews, 1987. 51(2): p. 221-271.
Written Opinion for International Application No. PCT/US2020/012572 filed on Jan. 7, 2020 on behalf of California Institute of Technology dated May 6, 2020 6 pages.
Written Opinion for International Application No. PCT/US2020/012557 filed on Jan. 7, 2020 on behalf of California Institute of Technology dated May 1, 2020 6 pages.
Yablonskiy, D.A., et al., "Theory of NMR signal behavior in magnetically inhomogeneous tissues: The static dephasing regime". Magnetic Resonance in Medicine, 1994. 32(6): p. 749-763.
Yi, et al., "Identifying clusters of functionally related genes in genomes", Bioinformatics, 2007. 23(9): p. 1053-1060.
Yin, L. et al., "Quantitatively Visualizing Tumor-Related Protease Activity in Vivo Using a Ratiometric Photoacoustic Probe." J. Am. Chem. Soc., 2019. 141(7): p. 3265-3273.
Yurist-Doutsch, S., et al., "Gastrointestinal microbiota-mediated control of enteric pathogens". Annual review of genetics, 2014. 48: p. 361-382.
Zabow, G., et al., "Shape-changing magnetic assemblies as highsensitivity NMR-readable nanoprobes". Nature, 2015. 520(7545): p. 73-77. 24 pages.
Zakeri, B., et al., "Peptide tag forming a rapid covalent bond to a protein, through engineering a bacterial adhesin". Proc. Natl. Acad. Sci. U. S. A., 2012. 109(12): p. E690-7.
Zhang, H. F. et al., "Imaging of hemoglobin oxygen saturation variations in single vessels in vivo using photoacoustic microscopy." *Appl. Phys. Lett.*90, 5-7, 053901(2007). 4 pages.
Zhang, S., et al., "PARACEST Agents: Modulating MRI Contrast via Water Proton Exchange". Accounts of Chemical Research, 2003. 36(10): p. 783-790.
Zordan, R.E., et al., "Avoiding the ends: internal epitope tagging of proteins using transposon Tn7". Genetics, 2015. 200(1): p. 47-58. 42 pages.
Zurkiya, O., et al., "Off-resonance saturation as a means of generating contrast with superparamagnetic nanoparticles". Magnetic Resonance in Medicine, 2006. 56(4): p. 726-732.
Final Office Action for U.S. Appl. No. 16/736,581, filed Jan. 7, 2020 on behalf of California Institute of Technology dated Dec. 13, 2021 50 pages.
International Preliminary Report on Patentability for International Application No. PCT/US2020/048572 filed on Aug. 28, 2020 on behalf of California Institute of Technology dated Mar. 1, 2022 7 pages.
Non-Final Office Action issued for U.S. Appl. No. 16/736,683, filed Jan. 7, 2020, on behalf of California Institute of Technology, dated Apr. 8, 2022. 36 Pages.
Notice of Allowance for U.S. Appl. No. 16/656,417, filed Oct. 17, 2019, on behalf of California Institute of Technology, dated Dec. 8, 2021. 7 Pages.
Notice of Allowance for U.S. Appl. No. 16/656,417, filed Oct. 17, 2019, on behalf of California Institute of Technology, dated Mar. 31, 2022. 19 Pages.
Non-Final Office Action for U.S. Appl. No. 161736,581 filed Jan. 7, 2020 on behalf of California Institute of Technology dated May 31, 2022 51 pages.
Notice of Allowance for U.S. Appl. No. 18/656,417 filed Oct. 17, 2019 on behalf of California Institute of Technology dated Jun. 27, 2022 9 pages.

* cited by examiner

COMPOSITIONS, METHODS AND SYSTEMS FOR GAS VESICLE BASED CAVITATION

CROSS-REFERENCE TO RELATED APPLICATIONS

The present application claims priority to U.S. Provisional Application No. 62/825,612, entitled "Genetically Encodable Nuclei For Inertial Cavitation" filed on Mar. 28, 2019, and U.S. Provisional Application No. 62/895,553, entitled "BURST Ultrasound Reconstruction with Signal Templates" filed on Sep. 4, 2019, which are incorporated herein by reference in their entirety. The present application may also be related to U.S. application Ser. No. 15/613,104 entitled "Gas-Filled Structures And Related Compositions, Methods And Systems To Image A Target Site" filed on Jun. 2, 2017 and patented as U.S. Pat. No. 10,493,172; U.S. application Ser. No. 15/633,600 entitled "Gas-Filled Structures And Related Compositions, Methods And Systems For Magnetic Resonance Imaging" filed on Jul. 28, 2017; U.S. application Ser. No. 15/663,635 entitled "Genetically Engineered Gas Vesicle Gene Clusters, Genetic Circuits, Vectors, Prokaryotic Cells, Compositions, Methods And Systems For Contrast-Enhanced Imaging" filed on Jul. 28, 2017; and U.S. application Ser. No. 16/736,683 entitled "Mammalian Expression of Gas Vesicles As Acoustic Reporter Genes" filed on Jan. 7, 2020; and to U.S. application Ser. No. 16/736,681 filed on Jan. 7, 2020, the contents of all of which are incorporated herein by reference in their entirety.

STATEMENT OF GOVERNMENT SUPPORT

This invention was made with government support under Grant No. EB018975 awarded by the National Institutes of Health. The government has certain rights in the invention.

FIELD

The present disclosure relates to gas-filled structures and the related use to create cavitation at a target site. The present disclosure is in particular directed to compositions methods and systems for Gas Vesical based cavitation, which can be used to open cell membranes for therapeutic effect or to achieve other effects associated with cavitation activity performed in an environment where cells are preferably present.

BACKGROUND

Cavitation is a phenomenon used in several applications such as chemical engineering, biomedical, cleaning as well as food and beverages applications.

Despite the knowledge and use of cavitation of microbubbles in both in vitro and in vivo application, precise microbubbles targeting and related uses appears to still be challenging. Specifically, microbubbles are purely intravascular and their biomolecular selectivity as imaging and therapeutic agents is limited. Bubble delivery can be performed using synthetic nuclei, which travel passively to their target and, due to their size, are limited to intravascular travel. They are also fairly unstable, leading to a decreased efficiency in terms of attachment to the target prior to dissolution of the bubbles.

SUMMARY

Provided herein are compositions, methods and systems for Gas-Vesicle (GV) based cavitation which in several embodiments allow precise nanobubble delivery and related biomolecular cavitation targeting and initiating cavitation in deep tissue regions. In contrast to current cavitation nuclei, GVs can be expressed in various cells, enabling them to reach new targets by sensing molecular signals that do not appear inside blood vessels. By expressing GVs only in response to specific signals, one can combine reporting with treatment.

Even purified GVs have advantages of being nano-scale and stable, improving their access to targets previously out of reach to cavitation.

According to a first aspect, an ultrasound pressure-based method is disclosed comprising: delivering a gas vesicle (GV) to a target site, the GV having a GV type collapse threshold pressure; setting an ultrasound generation system to produce ultrasound pulses having a positive pressure set above the GV type collapse threshold pressure, a negative pressure and at least one of: a duty cycle above 0.2% and a mechanical index above 2.8; and applying the ultrasound pulses to the target site, thus: collapsing the GV by the positive pressure of the ultrasound pulses, thereby forming gas bubbles; and cavitating the gas bubbles by the negative pressure.

The system comprises gas vesicles, either targeted or un-targeted, high intensity focused ultrasound system including a signal generator, an amplifier, and an ultrasound transducer. The system might or might not include an imaging modality such as ultrasound, MRI, OCT, or other. Also, the system might or might not include a passive acoustic detection or imaging system for feedback or control on the cavitation process. The gas vesicles can be purified from wild-type or engineered bacteria or archaea; they can include shell proteins modified by genetic engineering or chemical alterations to change the collapse pressure, circulation time or to facilitate attachment to specific cells.

According to a second aspect, a method of applying a mechanical stress to a cavitation target in a target site is described, the method comprising: delivering to the target site containing the cavitation target one or more gas vesicles (GVs) having a GV type collapse threshold, the delivering positioning the GVs in proximity of the cavitation target, and applying ultrasound pulses to the target site after the delivering, the ultrasound pulses selected to be sufficient to both collapse the GV type and to cavitate bubbles released by the GVs after collapse, the cavitated bubbles applying the mechanical stress to the cavitation target.

The cavitation target can be organic or inorganic. The mechanical stress can include, or deforming (e.g. pushing, pinching), damaging, destroying, dispersing, mixing, or moving, among other effects as would be known to one skilled in the art. The cavitation target can be already present at the target site or can be delivered to the target site with the GVs, such as a chemotherapy agent to be dispersed at the site. The GVs can be purified or in a delivery cell.

According to a third aspect, a method is described of lysing a target cell of a target tissue. The method comprises:

delivering to a target site containing the target tissue a gas vesicle (GV) type having a GV type collapse threshold, the delivering performed to provide the GV type in proximity of the target cell; and applying ultrasound pulses to the target site after the delivering, the ultrasound pulses selected to be sufficient to both collapse the GV type and to cavitate bubbles released by the GVs after collapse, the cavitated bubbles lysing the target cell.

The delivering the GV type in proximity of the target cell can include functionalizing the GV type to include binding sites that bind to the target cell.

The system comprises gas vesicles, either targeted or un-targeted, high intensity focused ultrasound system including a signal generator, an amplifier, and an ultrasound transducer. The kit might or might not include an imaging modality such as ultrasound, MRI, OCT, or other. Also, the kit might or might not include a passive acoustic detection or imaging system for feedback or control on the cavitation process. The gas vesicles can be purified from wild-type or engineered bacteria or archaea. They can include shell proteins modified by genetic engineering or chemical alterations. Alterations can include coating that increase circulation time (e.g. with polyethylene glycol (PEG)); coating with that enable attachment to specific cells (by adding a RGD peptide at the end of the GV, or coating with hyaluronic acid (HA) for example). Additional approaches can include the use click chemistry or antibodies.

According to a fourth aspect, a method is described of lysing a target cell of a target tissue. The method comprises:

delivering to a target site containing the target tissue a delivery cell containing a gas vesicle (GV) type having a GV type collapse threshold, the GV type having a GV type collapse threshold, the delivering performed for a time and under conditions allowing expression of the GV type in the delivery cell; and when the delivery cell is in proximity of the target cell, applying ultrasound pulses to the target site after the delivering, the ultrasound pulses selected to be sufficient to both collapse the GV type and to cavitate bubbles released by the GVs after collapse, the cavitated bubbles lysing the delivery cell thereby lysing the target cell.

According to a fifth aspect, a method is described of delivering a target compound to a target tissue, the method comprising:

delivering to the target tissue a delivery cell configured to contain the target compound and to express a gas vesicle (GV) type, the delivering performed for a time and under conditions allowing expression of the GV type in the cell; and applying ultrasound pulses to the target site after the delivering, the ultrasound pulses selected to be sufficient to both collapse the GV type and to cavitate bubbles released by the GVs after collapse, the cavitated bubbles lysing the delivery cell and delivering the target compound to the tissue.

The system comprises a delivery cells engineered to express gas vesicles, high intensity focused ultrasound system including a signal generator, an amplifier, and an ultrasound transducer. The kit might or might not include an imaging modality such as ultrasound, MRI, OCT, or other. Also, the kit might or might not include a passive acoustic detection or imaging system for feedback or control on the cavitation process. The GVs might be expressed at the time at which the delivery cell is delivered or produced in situ after the delivery cell reached its target and colonized it. In situ production of GVs can be initiated in response to local chemical signals, change in local temperature, or any other signal. The cell can include or produce genetically engineered GV types having a GvpC modified to bind to the cell membrane or other location within the cell. Alternatively, the cell can include GVs modified to bind to the extracellular environment in proximity of the cell membrane. It can also include or produce GV types having a GvpC modified to have lower collapse pressure, either continuously or in response to an external signal.

According to a sixth aspect, a method is described for damaging a material at the target site comprise delivering to a target site containing the target tissue a gas vesicle (GV) type having a GV type collapse threshold, the delivering performed to provide the GV type in proximity of the material; and applying ultrasound pulses to the target site after the delivering, the ultrasound pulses selected to be sufficient to both collapse the GV type and to cavitate bubbles released by the GVs after collapse, the cavitated bubbles damaging the material at the target site.

Methods and systems for Gas Vesicle-based cavitation and related compositions herein described, can be used in several embodiments to allow precise nanobubble delivery, bubble growth, and subsequent application of mechanical stress (e.g. rupture, bending, propelling, pinching, stretching, mixing) to a cavitation target in a target site, wherein cavitation targets can be a portion of materials (e.g. co-administered drugs, capsules, or implants), deposit formations within a living organism or portions thereof, as well as organs, tissues, cells or portions thereof.

Methods and systems for Gas Vesicle-based cavitation and related compositions herein described, can be used in several embodiments to nucleate cavitation activity based on molecular signals or lower the threshold for cavitation activity for an extended amount of time due to the stability of gas vesicles.

Methods and systems for Gas Vesicle-based cavitation and related compositions herein described, can be used in several embodiments wherein the cavitation target site is a living individual, a related organ, tissue, ex vivo or in vitro sample, cell culture, and additional target sites identifiable by a skilled person.

Methods and systems for Gas Vesicle-based cavitation and related compositions herein described, can be used in several embodiments wherein the cavitation target is a cell or portions thereof to lyse cell walls or other portions thereof and/or kill cells for experimental diagnostic and/or therapeutic effect or to achieve other effects associated with a cavitation performed in an environment where cells are present.

The methods and systems for GV based-cavitation and related compositions, herein described can be used in connection with various applications wherein cell lysis and/or controlled cavitation in a target site is desired. For example, methods and systems for GV based-cavitation and related compositions herein described can be used in connection with various applications wherein controlled cavitation in a target site is desired. For example, methods and systems for GV based-cavitation and related compositions herein described can be used for the selective lysis of tumor cells, the uncaging of drugs from GV containing materials, the delivery of co-injected materials into cells, the activation of the immune system, and the delivery of therapeutic cellular agents, among other advantages identifiable by a skilled person, in medical applications.

Other applications of GV cavitation herein described comprise selective removal of materials from within the body (clots, stones, etc.), seeding cavitation enhanced hyperthermia, enhanced drug delivery for chemotherapy treatment. Additional exemplary applications include uses of methods and systems for GV based-cavitation and related compositions herein described in several fields including basic biology research, applied biology, bio-engineering, bio-energy, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTIONS OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 1 describes the ultrasound parameters that control the process of GV cavitation FIG. 2 shows an example method of using GVs for therapeutic cavitation.

Figure 8:
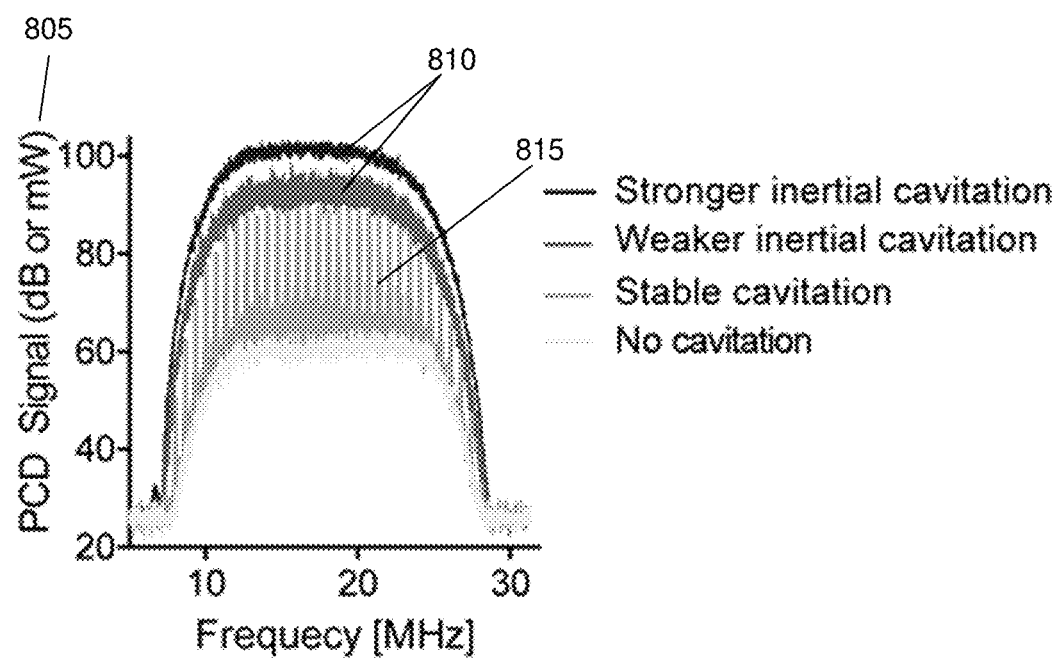

FIG. 8 Includes an example of the acoustic signature of stable cavitation and two levels of inertial cavitation.

Figure 9A:
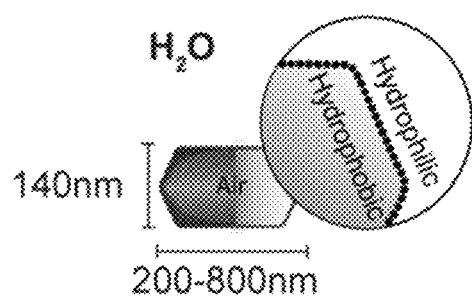
Figure 9B:
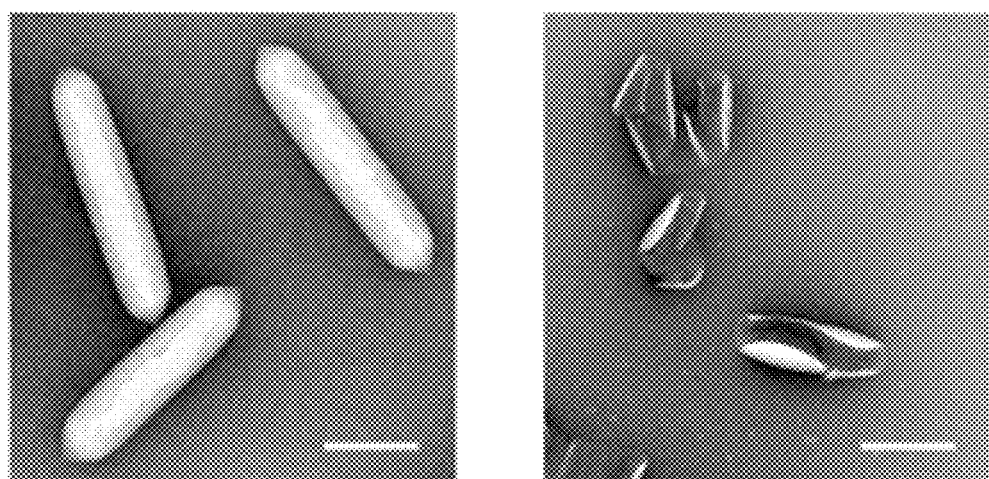
Figure 9C:
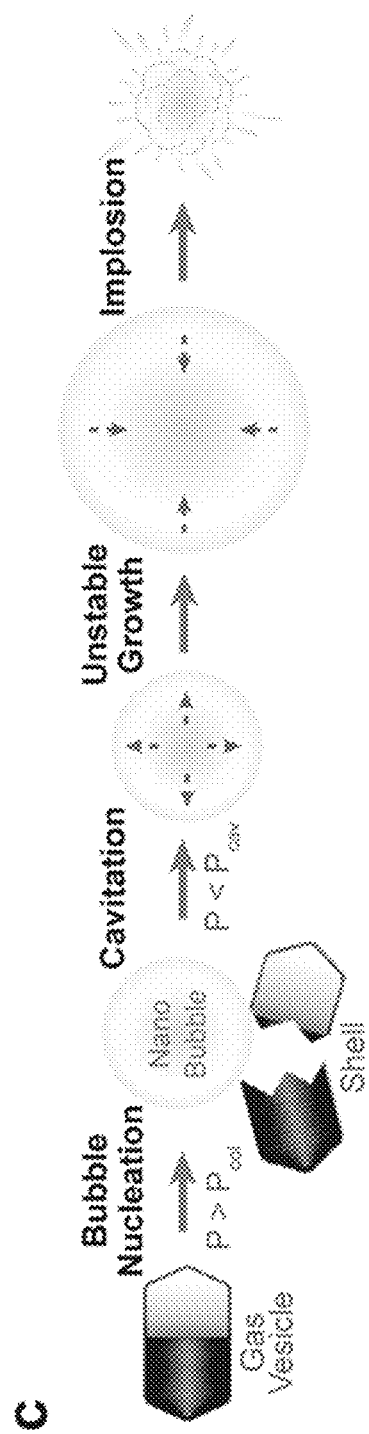

FIGS. 9A-9C show an example of gas vesicles as nuclei for inertial cavitation. FIG. 9A shows a schematic representation of an exemplary GV with a chart indicating the related exemplary dimensions and color coding indicating the amphiphilic nature of protein shell enclosing a stable, gas-filled structure. FIG. 9B shows an example representative transmission electron microscopy (TEM) images of intact (left) and collapsed (right) exemplary GV from *Anabaena flos-aquae*. FIG. 9C shows a schematic representation of an example mechanism of GV-seeded cavitation. Scale bar represents 200 nm.

Figure 10:
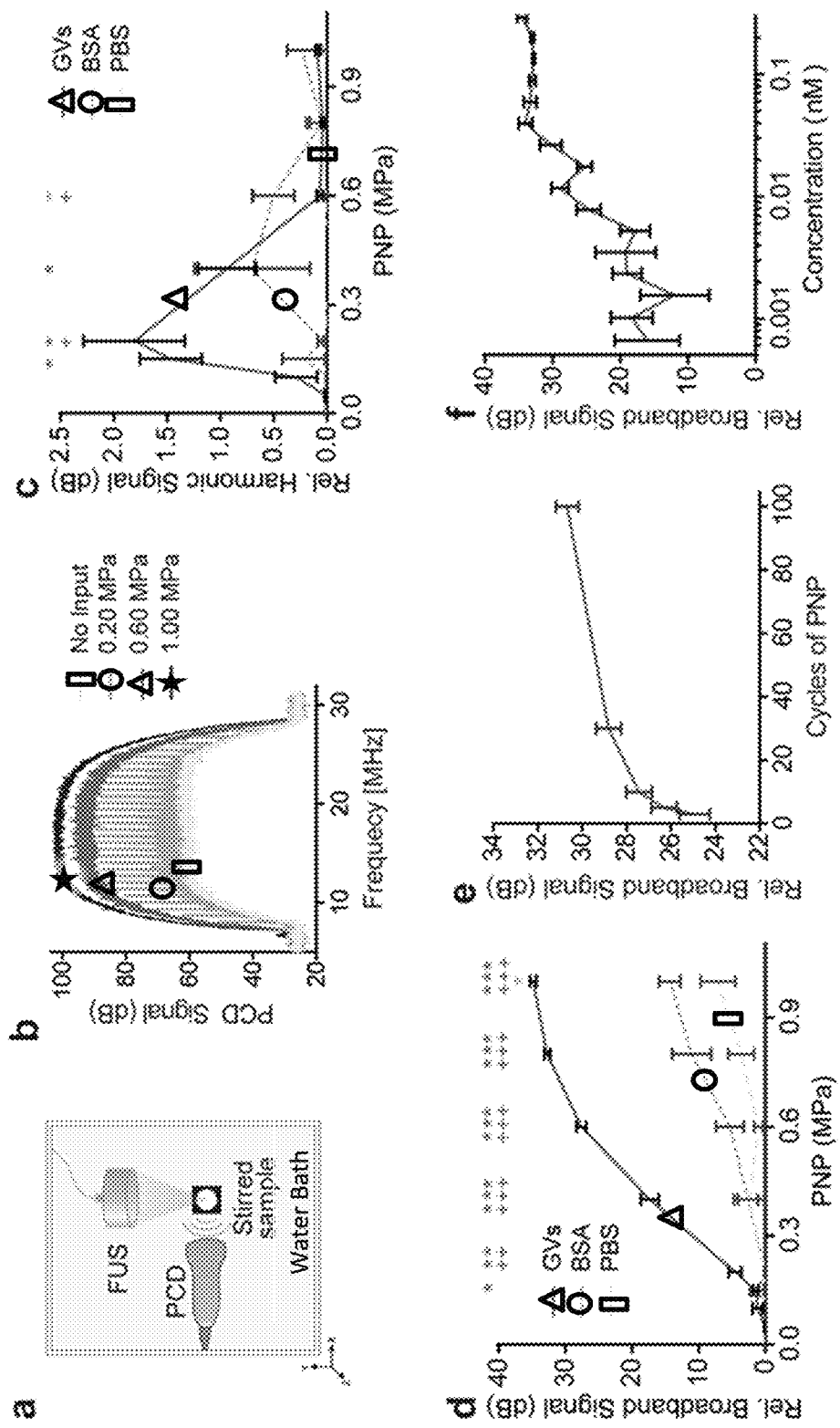

FIG. 10 shows the results of an example of purified GVs acting as seeds for stable and inertial cavitation. FIG. 10 Panel a shows a diagram of in vitro passive cavitation detection (PCD) setup used to measure the acoustic signatures of cavitation activity in response to focused ultrasound (FUS). FIG. 10 Panel b shows representative frequency spectra of backscattered signals from purified GVs insonated by a single US pulse at varying peak negative pressures (PNP). FIG. 10 Panel c shows a mean harmonic signal from GVs, bovine serum albumin, and PBS as a function of PNP. FIG. 10 Panel d shows a mean broadband signal from GVs, BSA, and PBS as a function of PNP. FIG. 10 Panel e shows average broadband measurements from GVs insonated with varying ultrasound pulse lengths. FIG. 10 Panel f shows a broadband signal from different concentrations of GVs insonated with a single 1.0 MPa pulse.

Figure 11:
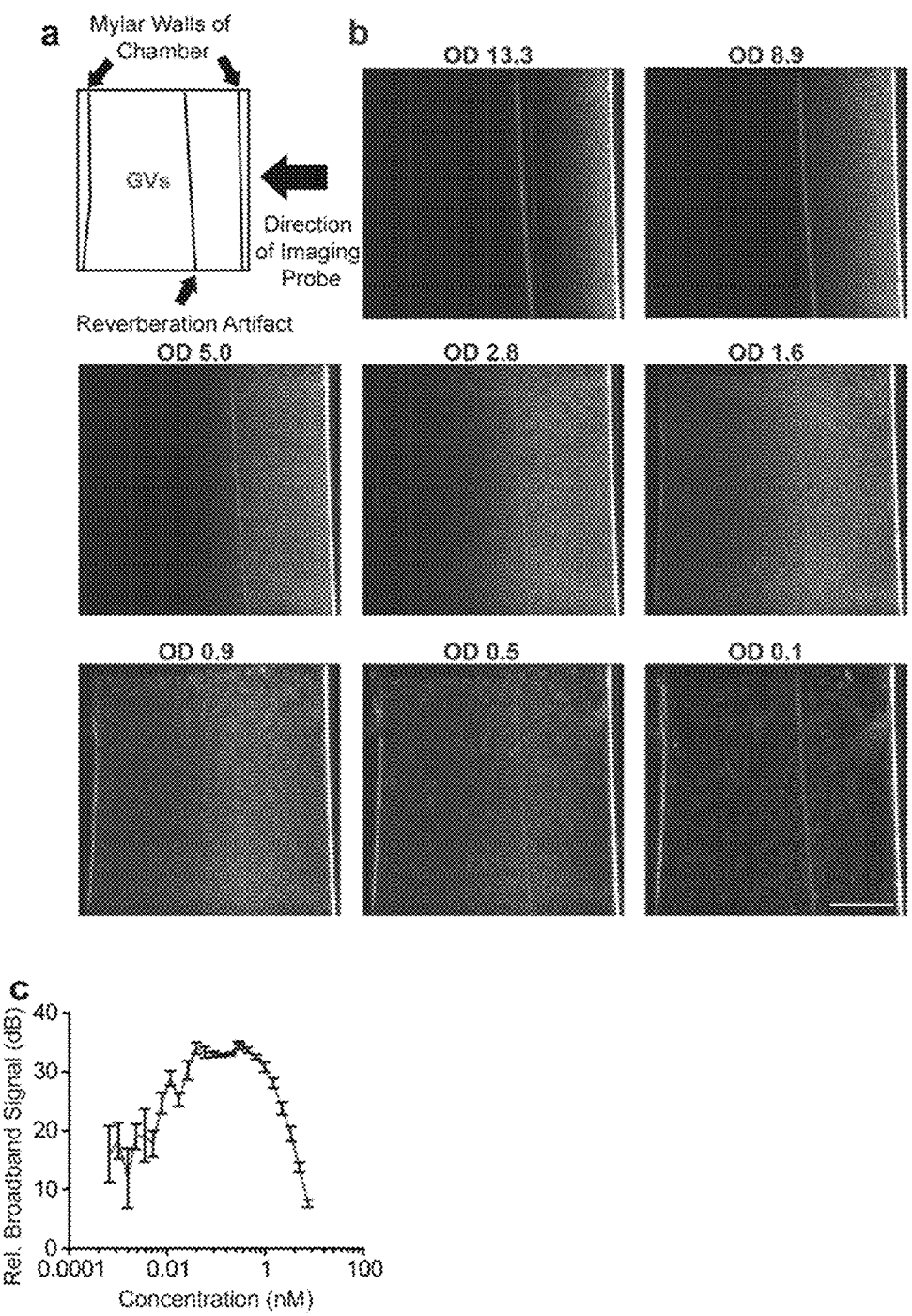

FIG. 11 shows an example of shows the effect of GV concentration on cavitation activity. FIG. 11 Panel a shows an illustration of the sample chamber and setup as seen in the images. FIG. 11 Panel b shows B-mode images of purified Ana GVs in different concentrations showing acoustic shadowing in high concentrations. Scale bars represent 3 mm. Panel c shows the effect of high GV concentrations on average broadband measurements.

Figure 12:
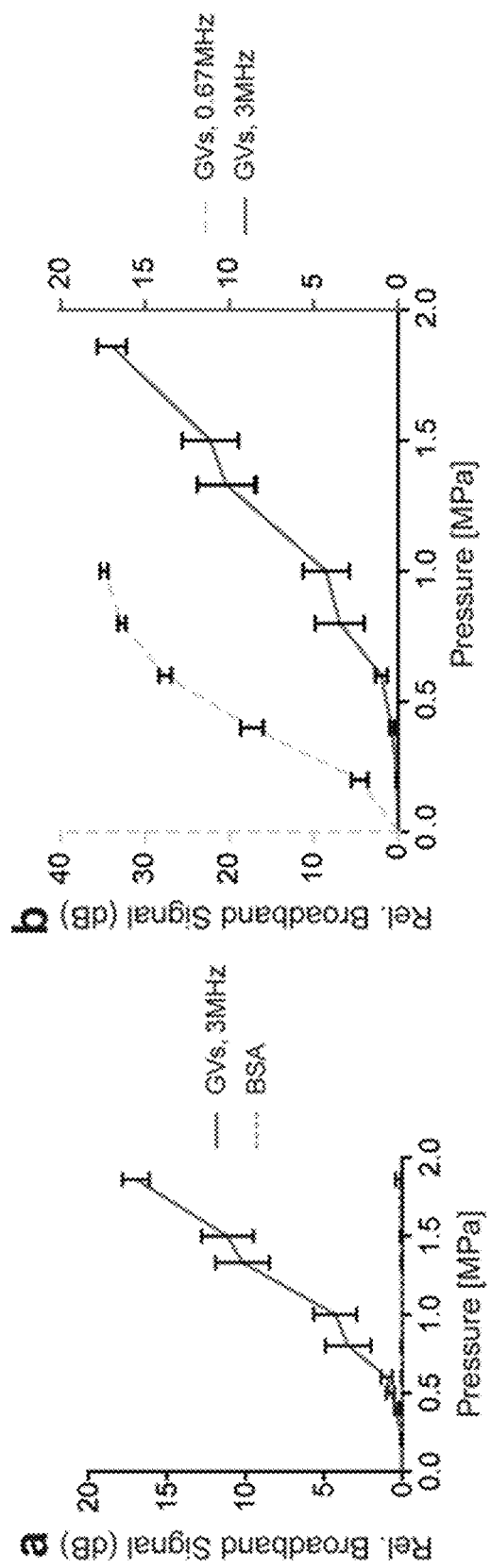

FIG. 12 shows an example that GV-seeded cavitation at 3 MHz requires higher pressure levels. FIG. 12 Panel a shows broadband signals recorded from GVs (0.3 nM) and BSA (matched in mg/mL to GVs concentration) insonated at 3 MHz. FIG. 12 Panel b shows a comparison between broadband signals from GVs insonated with 0.67 MHz and 3 MHz pulses.

Figure 13A:
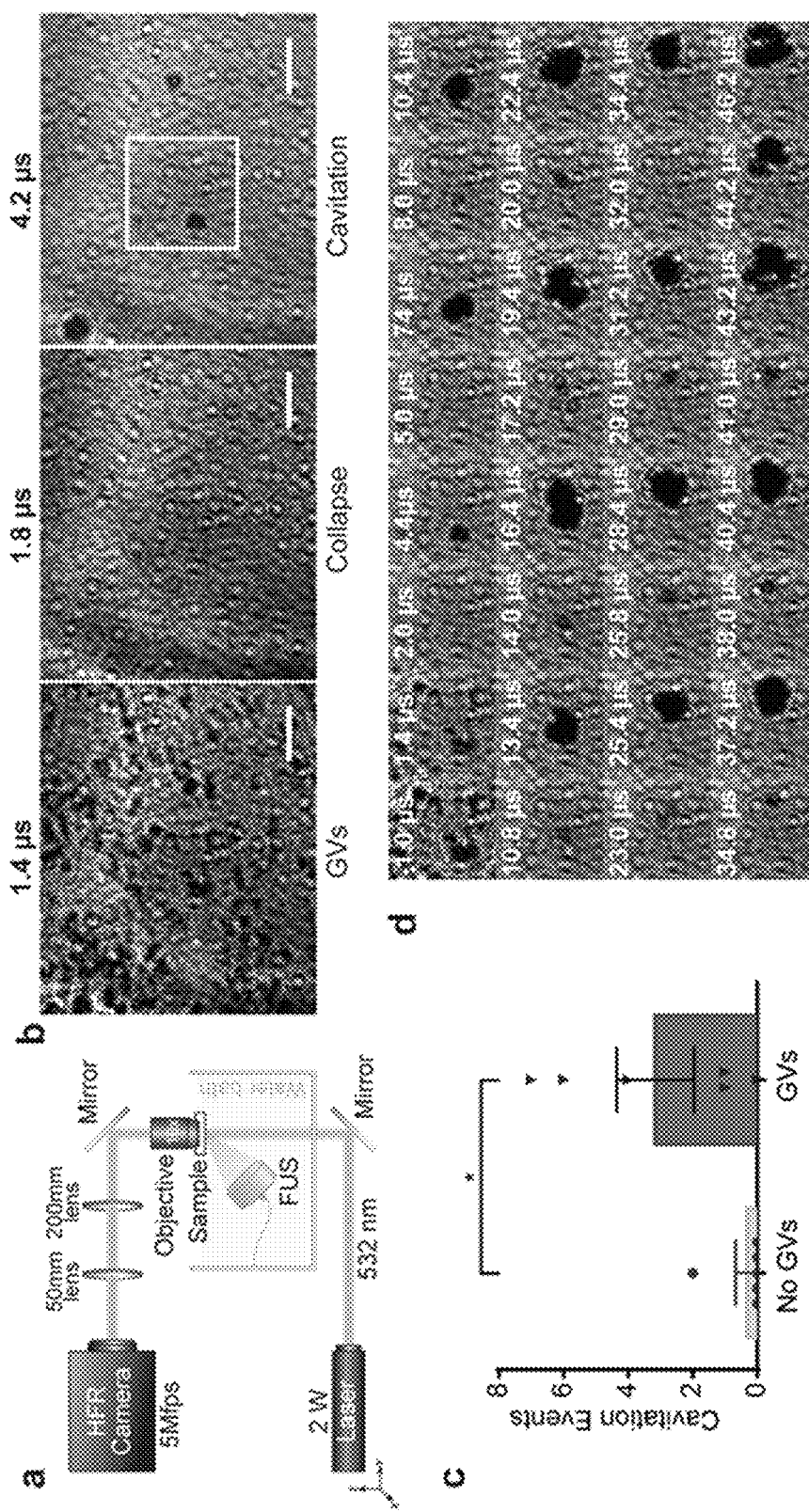
Figure 13B:
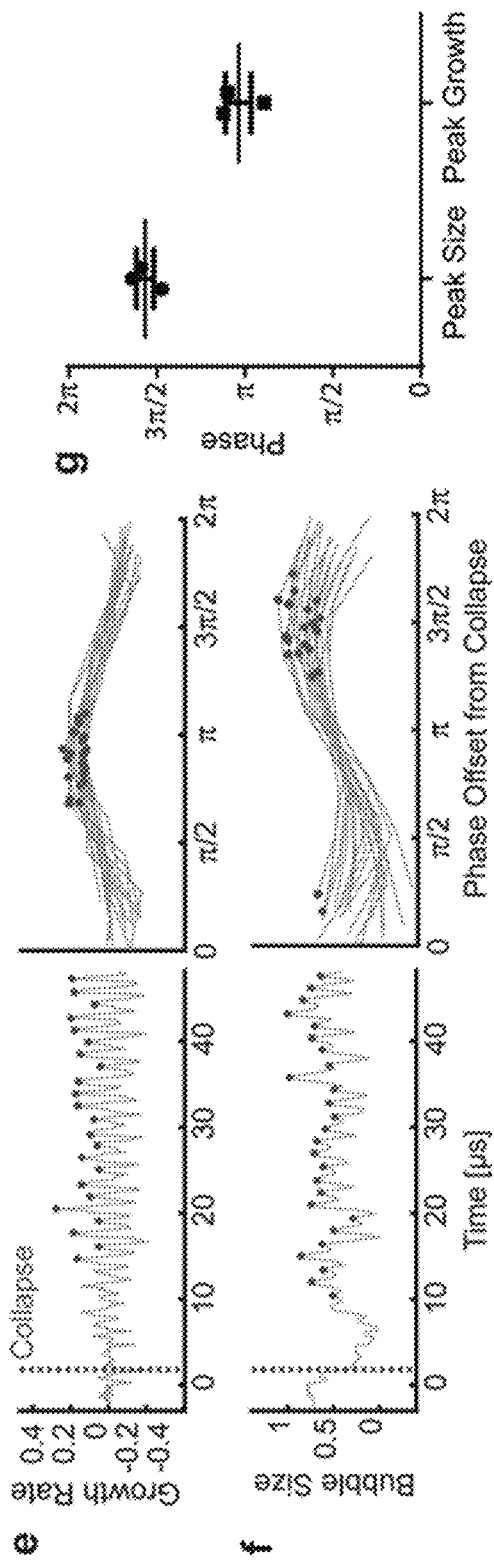

FIGS. 13A-13B show an example of ultrafast optical imaging of GV-seeded bubble formation and cavitation. In particular, FIG. 13A Panel a shows a schematic drawing of the high frame rate (HFR) camera setup enabling GV cavitation imaging at a frame rate of 5 MHz. FIG. 13A Panel b shows HFR camera images immediately before GV collapse (left), immediately after GV collapse (middle), and after the formation of bubbles (right). FIG. 13A Panel c shows the number of unique cavitation loci in biotinylated dishes with and without GVs, upon insonation with a single 1.4 MPa burst. FIG. 13A Panel d shows representative high-speed camera frames showing every other maximum and minimum of bubble cavitation, preceded by GV collapse. FIG. 13B Panel e shows bubble growth rate, quantified as the temporal derivative of the normalized average inverted pixel intensity in FIG. 13A Panel d (left). FIG. 13B Panel f shows bubble size and phase offset from GV collapse analyzed from HFR images as in FIG. 13A Panel d. FIG. 13B Panel g shows average phase offset for peak size and peak growth rate of bubbles in three different regions of interest. The scale bar represents 20 μm.

Figure 14:
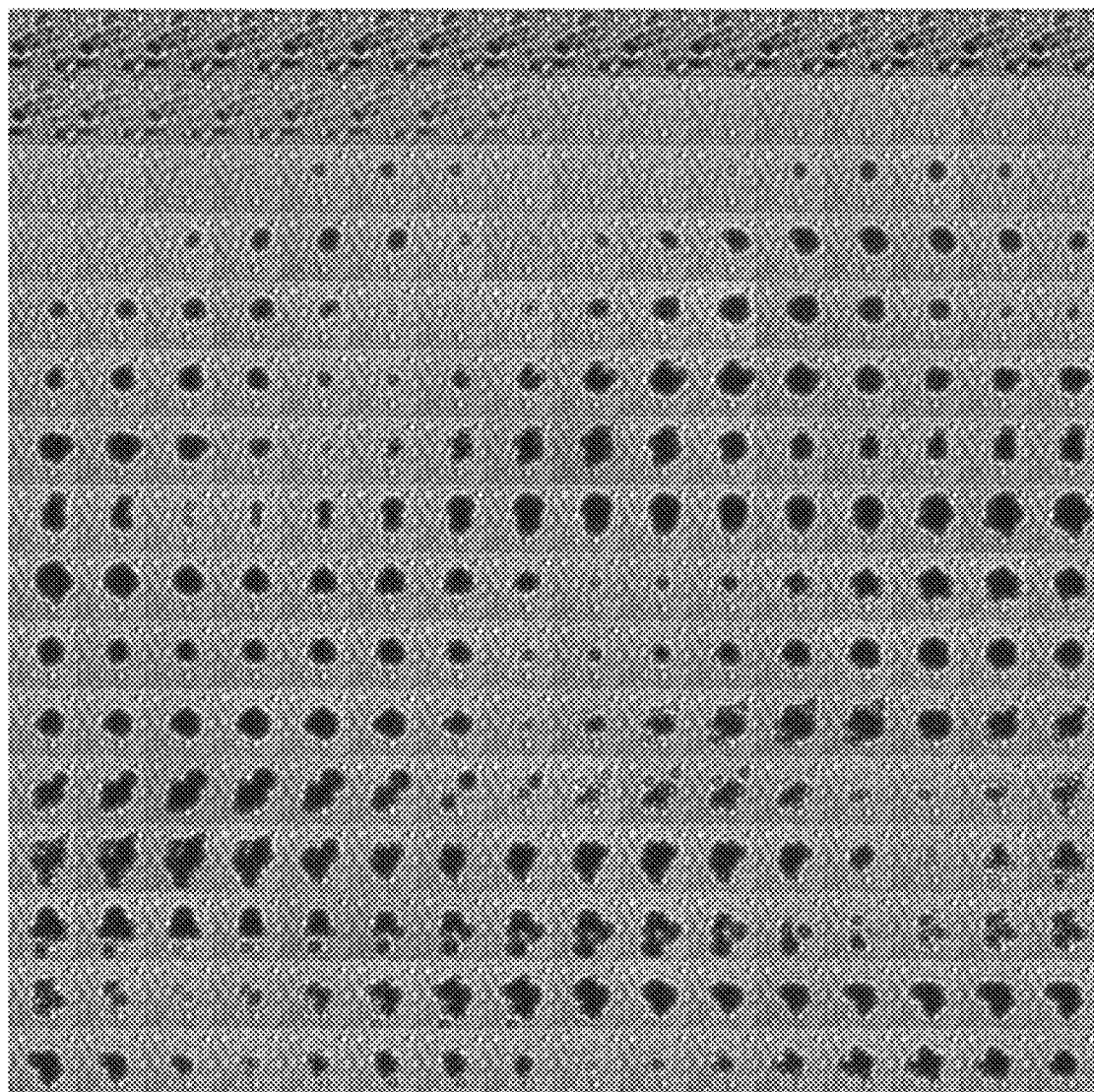

FIG. 14 shows an example of high frame rate optical imaging of GV collapse and bubble cavitation.

Figure 15A:
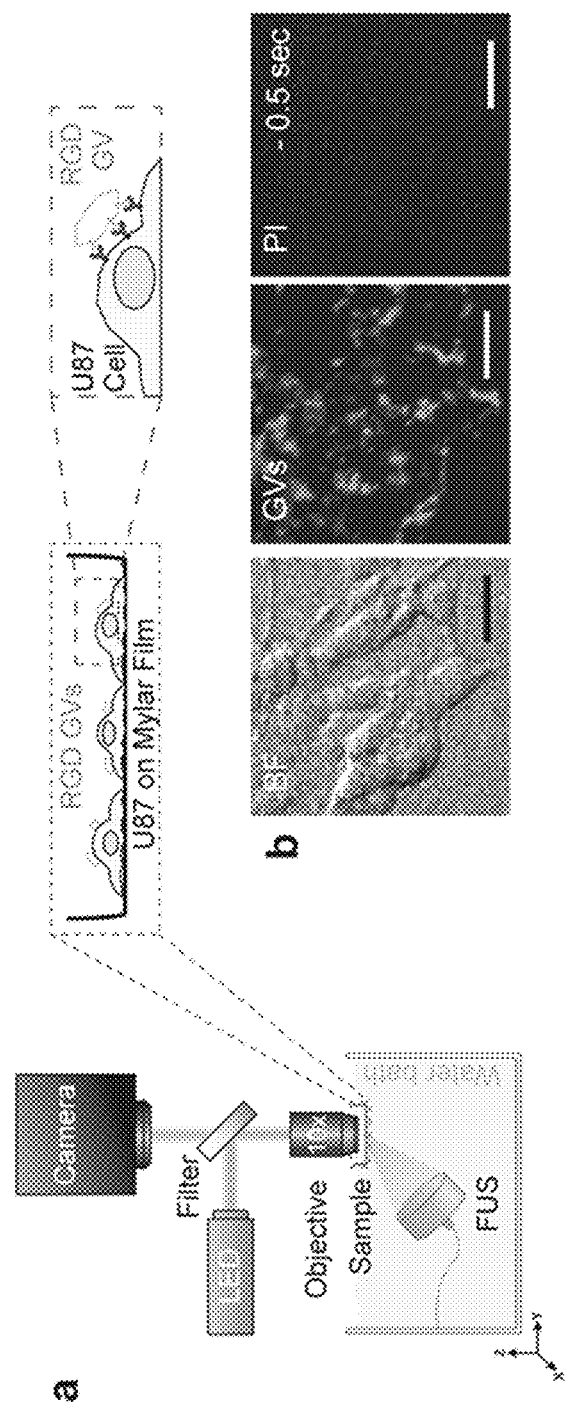
Figure 15B:
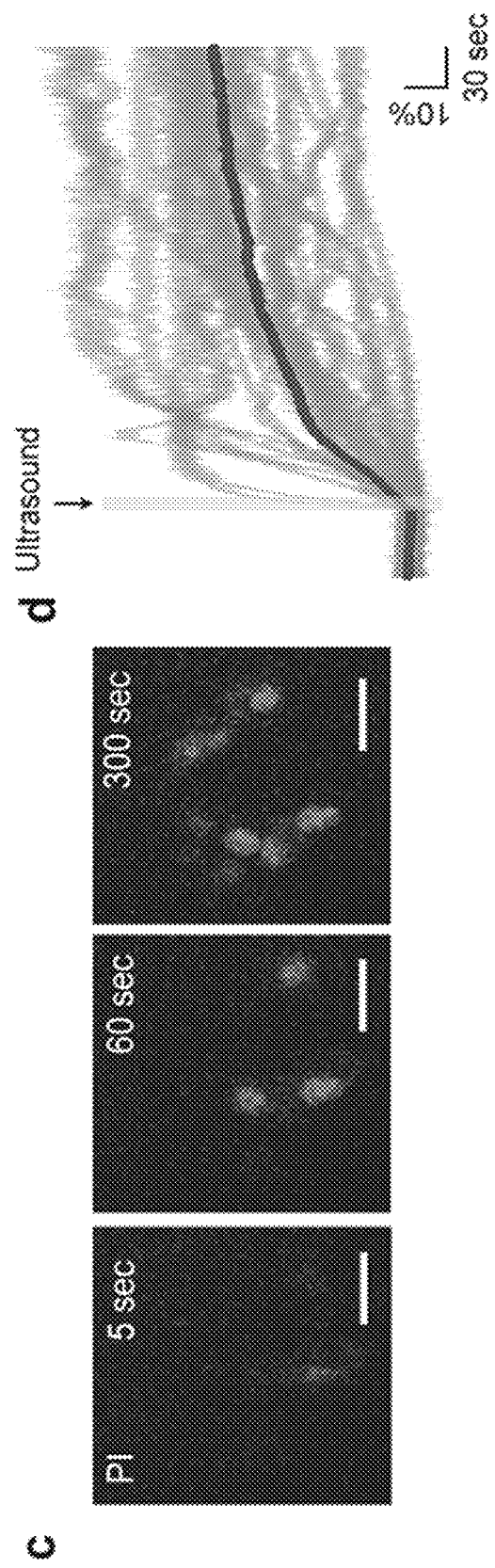
Figure 15C:
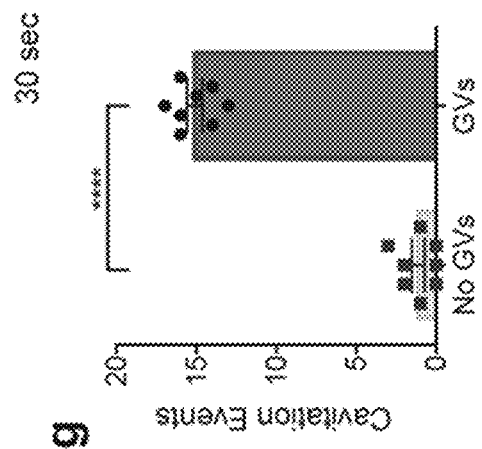
Figure 15C:
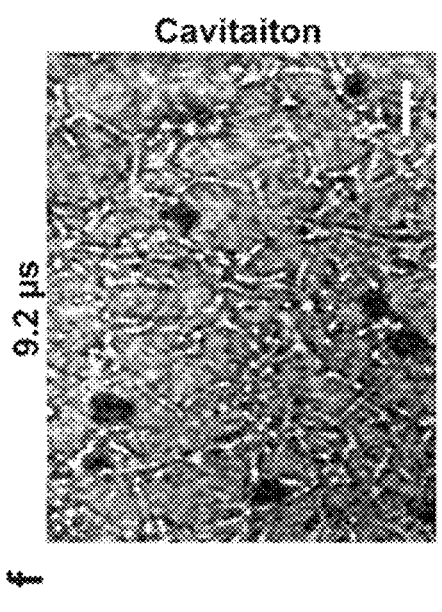
Figure 15C:
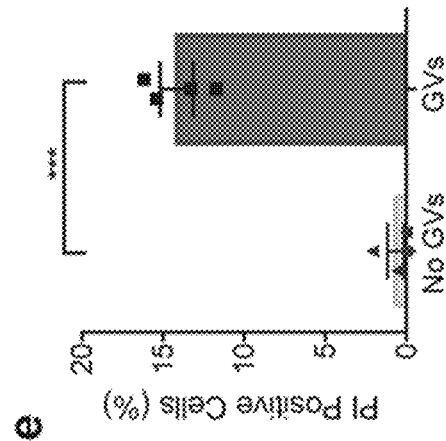

FIGS. 15A-15C show an example of molecularly-targeted GVs serving as ultrasound-triggered disruptors of mammalian cells. FIG. 15A Panel a shows a schematic drawing of the fluorescent microscopy setup used for imaging of GV-mediated cell disruption. FIG. 15A Panel b shows a bright field (BF) image of U87 cells (left), fluorescence images of GVs (middle), and propidium iodide (PI) (right), before the application of ultrasound. FIG. 15B Panel c shows PI fluorescence 5, 60, or 300 sec after ultrasound exposure. FIG. 15B Panel d shows a change in PI signal measured from individual cells (gray) and the average (black) before, during and after FUS application (vertical bar). FIG. 15C Panel e shows a percentage of PI-positive cells following ultrasound exposure with and without GV attachment. FIG. 15C Panel f shows an HFR camera image showing the formation of bubbles during ultrasound application to cells treated with GVs. FIG. 15C Panel g shows a number of unique cavitation loci observed in dishes containing U87 cells with and without GVs. Scale bars represent 20 μm.

Figure 16:
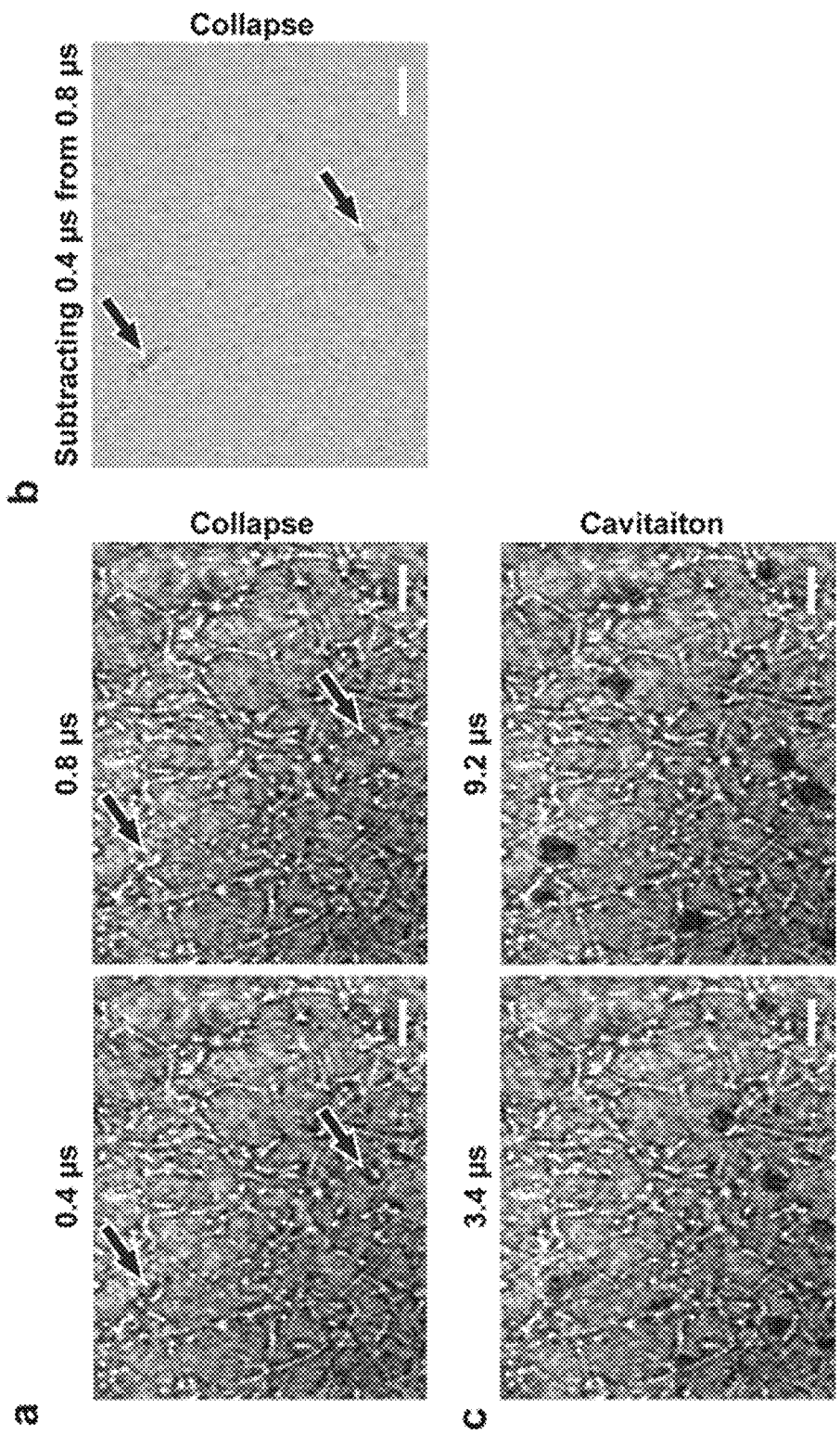

FIG. 16 shows an example of high frame rate recording of GVs attached to tumor cells. FIG. 16 Panel a shows the images of cells before and after GV collapse. FIG. 16 Panel b shows a differential image of GV collapse. FIG. 16 Panel c shows images of resulting bubbles cavitating next to the cells.

Figure 17A:
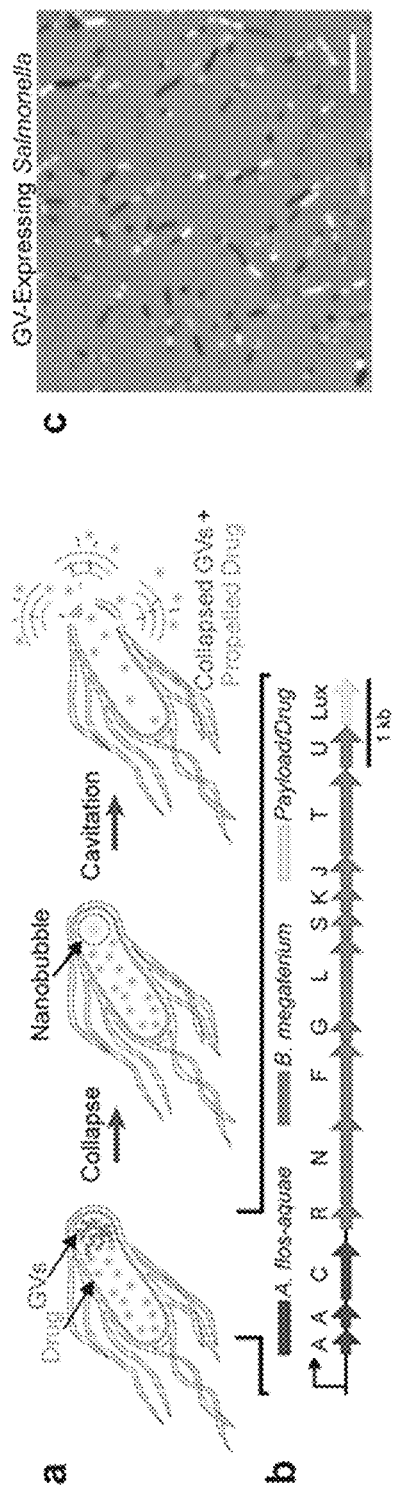
Figure 17B:
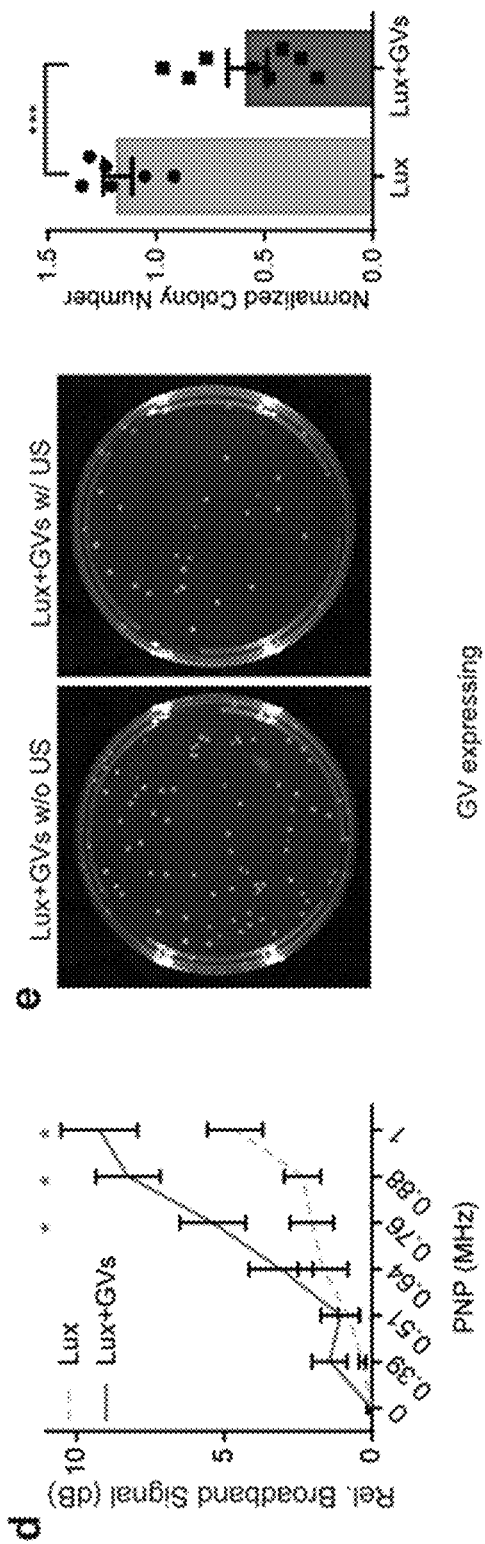
Figure 17C:
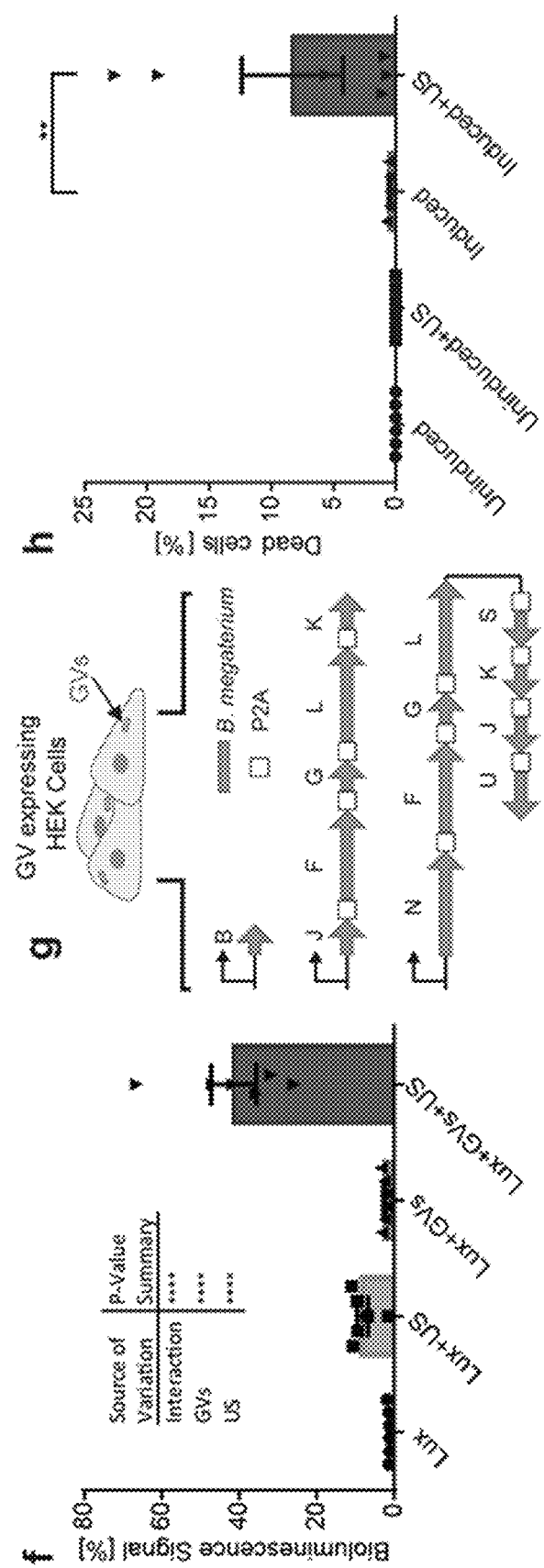

FIGS. 17A-17C show an example of GVs as genetically encoded seeds for cellular inertial cavitation and payload release. FIG. 17A Panel a shows a mechanism of intracellular GV-seeded cavitation and cell disruption. FIG. 17A Panel b shows a genetic construct combining a hybrid gas vesicle gene cluster from *A. flos-aquae* and *B. megaterium* with a luciferase (Lux) payload. FIG. 17A Panel c shows a phase contrast microscopy image of *S. typhimurium* cells expressing the construct in FIG. 17A Panel b. GVs appear inside the cells as white inclusions, while the rest of the cells appear black. FIG. 17B Panel d shows mean broadband emissions from Lux-expressing cells (Lux, negative control) and cells co-expressing GVs and Lux, at various pressure levels. FIG. 17B Panel e shows representative agar plates and average colony counts for Lux and Lux+GV cells exposed to ultrasound, normalized by the number of colonies from non-exposed control samples. FIG. 17C Panel f shows a bioluminescent signal in the media surrounding Lux or Lux+GV cells with and without exposure to ultrasound. FIG. 17C Panel g shows a structure of the three plasmids containing the mammalian gas vesicle gene cluster. FIG. 17C Panel h shows selective bursting of mammalian HEK293T cells using ultrasound. Scale bar represents 15 µm.

Figure 18A:
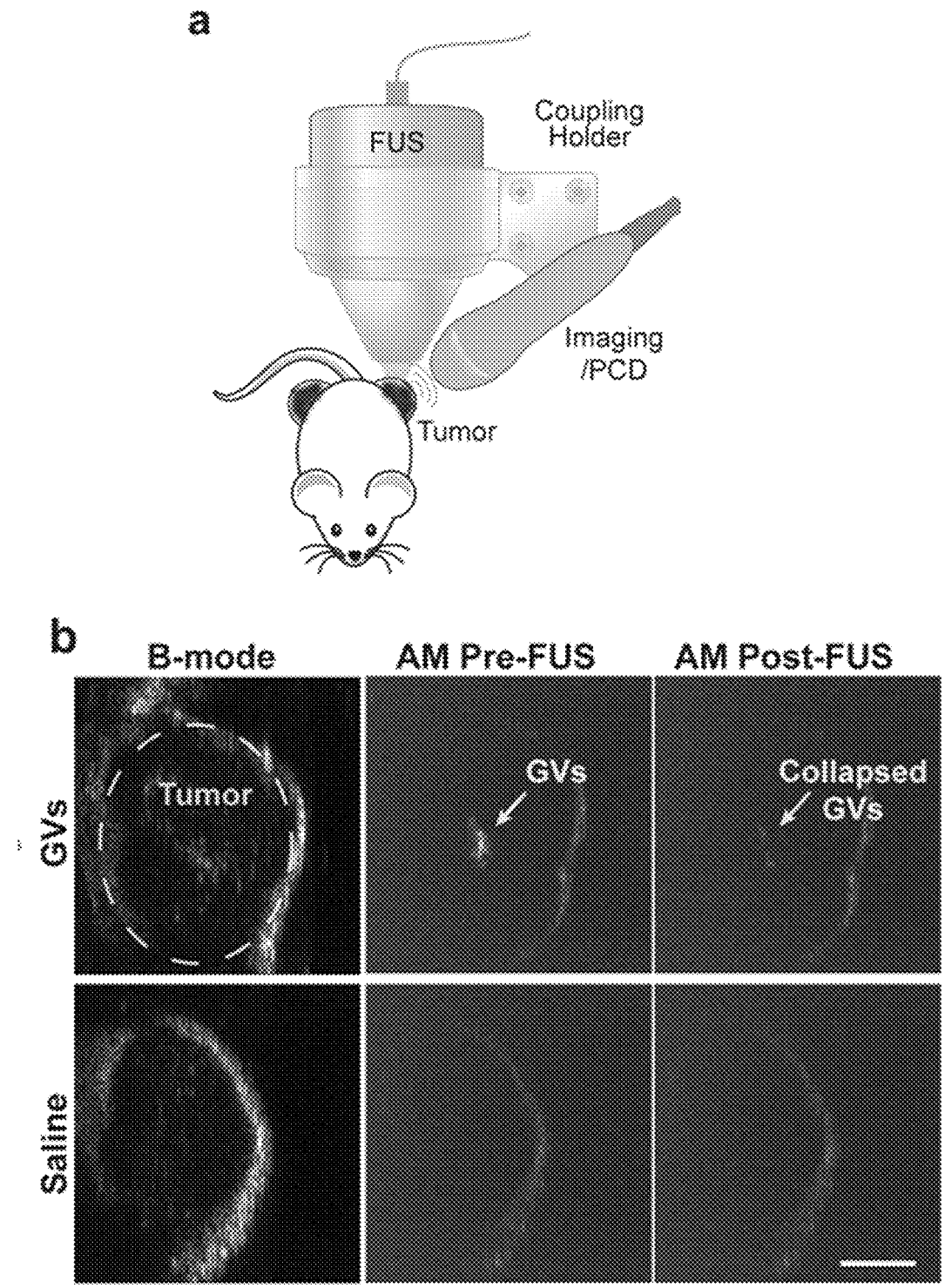
Figure 18B:
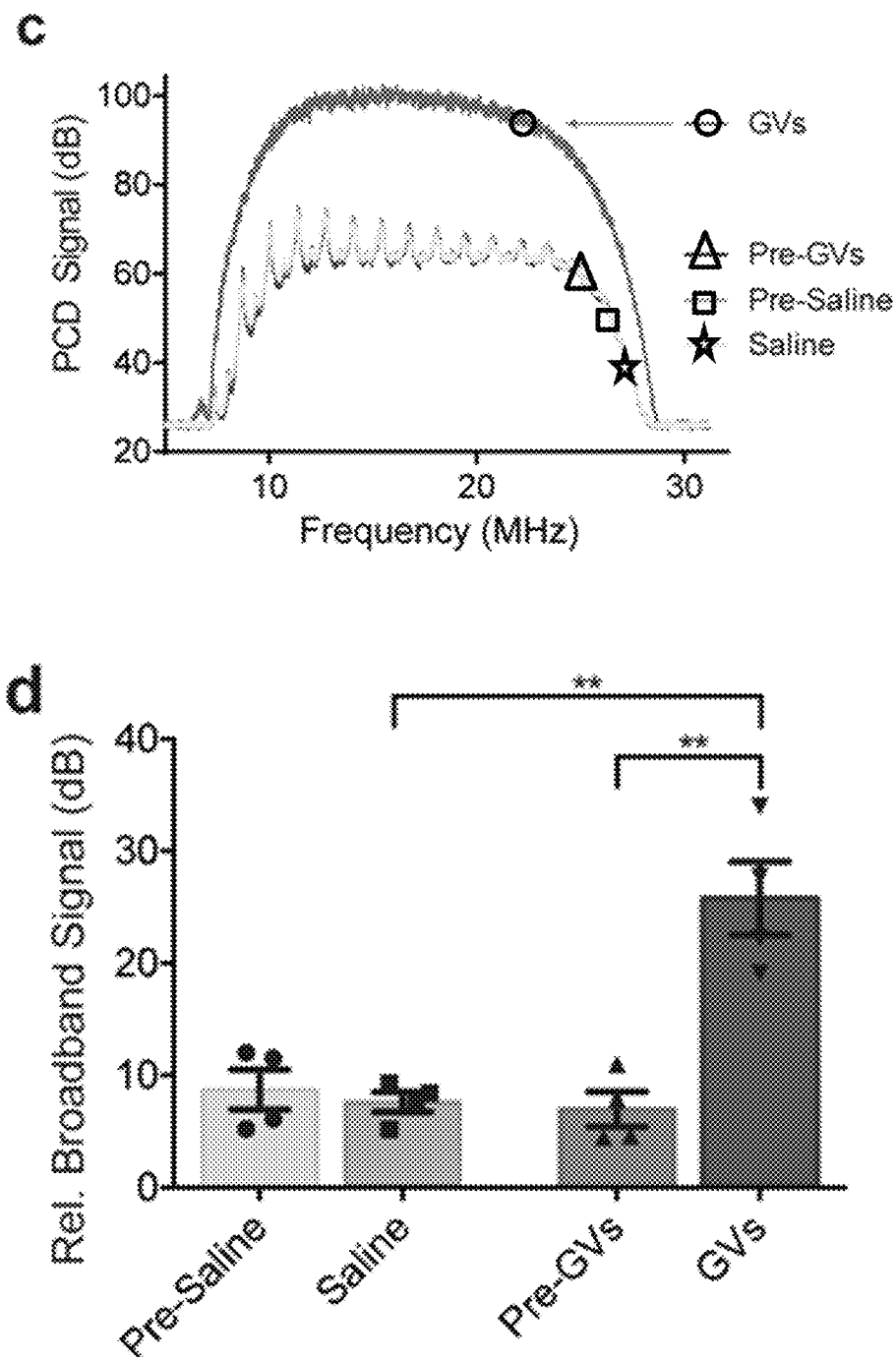
Figure 18C:
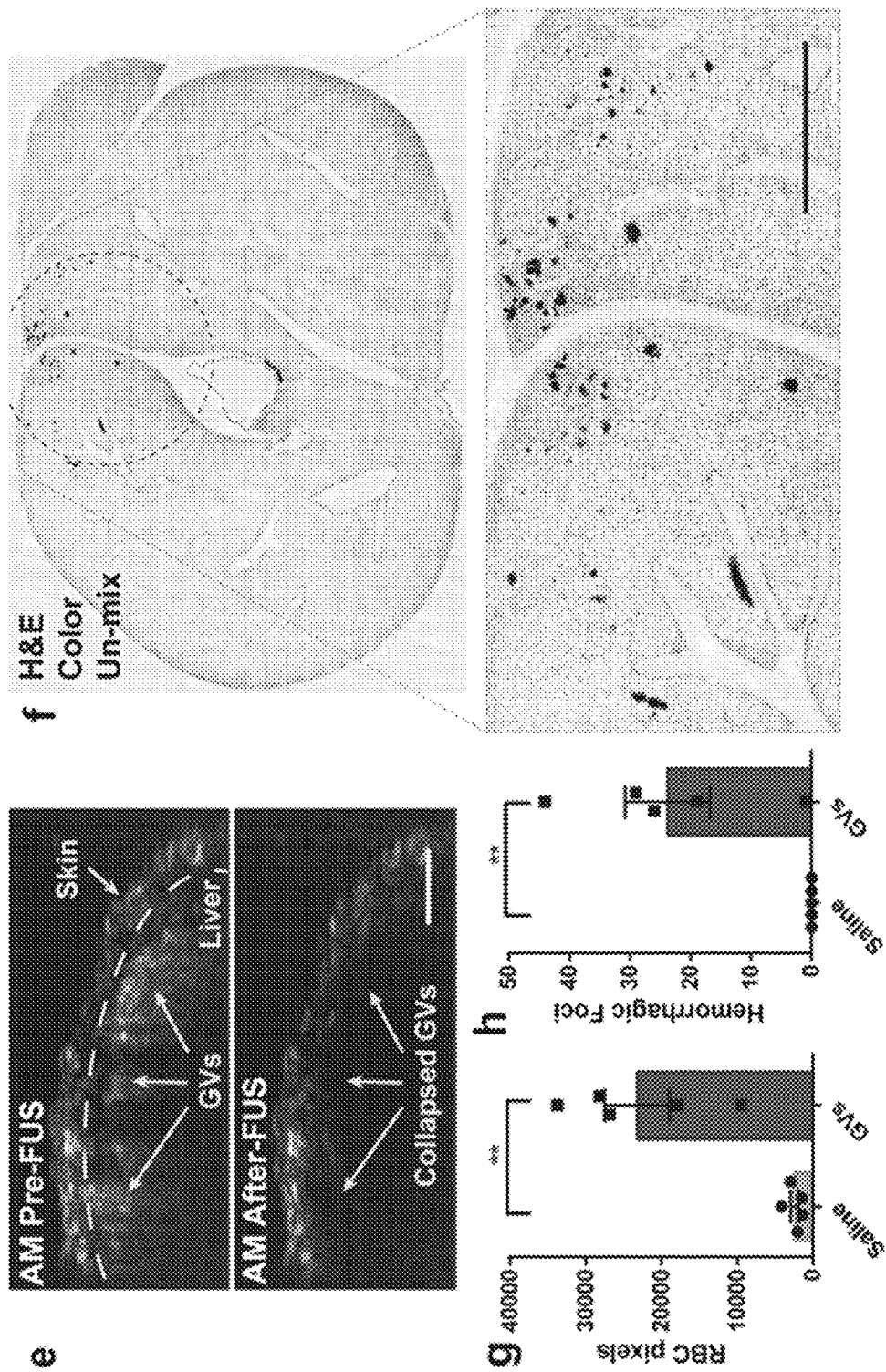

FIGS. 18A-18C show an example of theranosic imaging and GV-seeded cavitation in vivo. FIG. 18A Panel a shows a schematic drawing of in vivo FUS and imaging/PCD setup. FIG. 18A Panel b shows ultrasound images of tumors injected with engineered nonlinear GVs or saline (sham control). FIG. 18B Panel c shows representative PCD spectra measured before and after injection of purified GVs or saline into tumors. FIG. 18B Panel d shows a relative broadband signal measured from pre- and post-GV and saline injections into tumors. FIG. 18C Panel e shows amplitude modulation images showing GV accumulation inside the liver, 2 minutes after a systemic injection. FIG. 18C Panel f shows gas vesicle cavitation producing local tissue damage. FIG. 18C Panel g shows an increase in the number of blood related pixels in the medial lobe of mice injected with GVs vs. saline control. FIG. 18C Panel h shows a number of hemorrhagic foci surrounded by necrotic regions in livers of mice injected with GVs vs. saline control. Scale bar is 3 mm for Panel b and 1 mm for Panels e and f.

Figure 19:
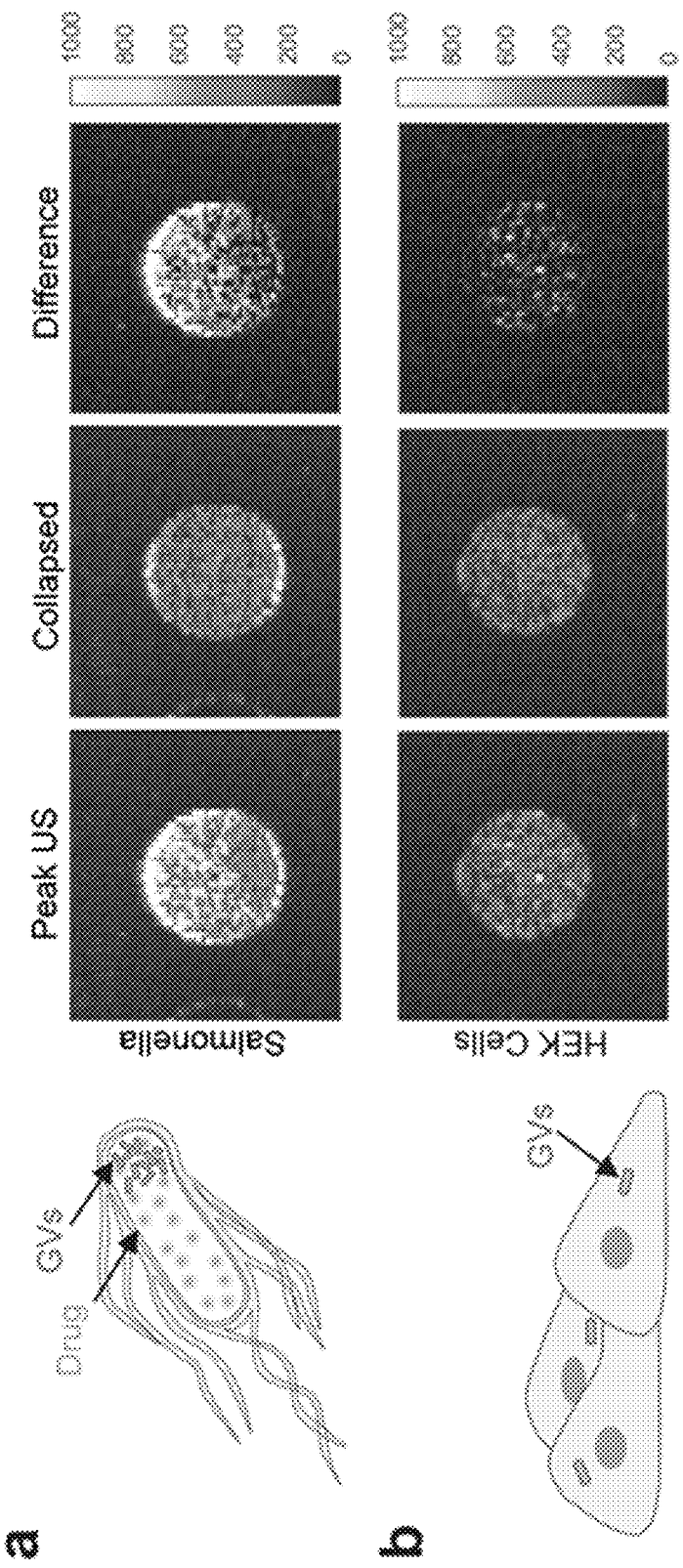

FIG. 19 illustrates ultrasound images comparing gas vesicle expression in bacteria and mammalian cells. FIG. 19 Panel a shows ultrasound images of agarose phantoms containing *S. typhimurium* cells expressing gas vesicles, taken after a pressure ramp. The initial amplitude modulation (AM) frame shows the echo from collapsing gas vesicles (left, Peak US,), and the second one presents the residual signal from the cells after bubble dissolution (middle, Collapsed). The gas vesicle specific signal, calculated as the difference between these two images, reveals high gas vesicle content in bacteria (right, Difference). FIG. 19 Panel b shows ultrasound images of agarose phantoms containing gas vesicle expressing HEK293T cells. The partial volume occupied by gas vesicle in mammalian cell is much lower than in bacteria, resulting in lower differential signal in the right image.

Figure 20:
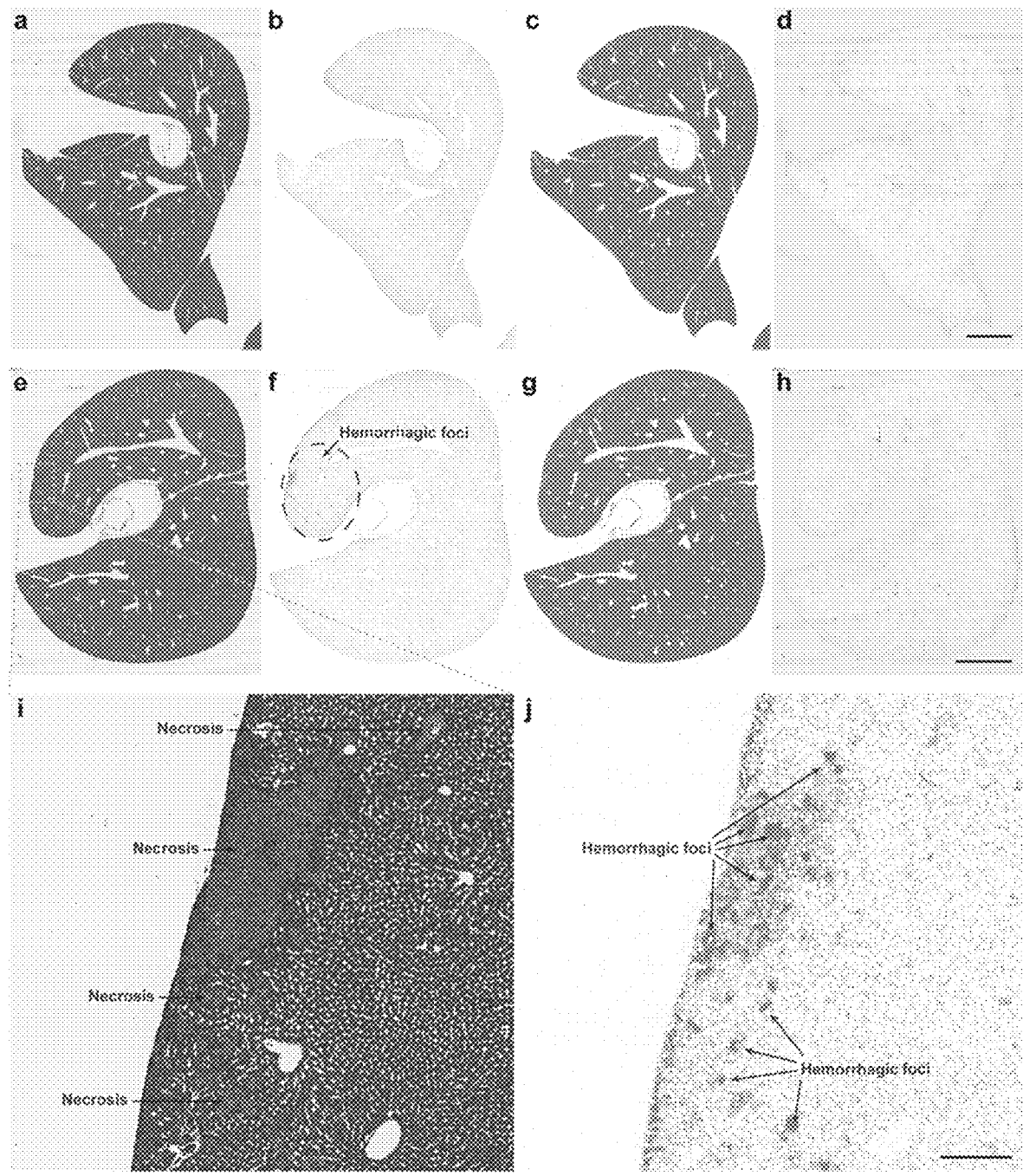

FIG. 20 illustrates the GV cavitation on surrounding tissues revealed by color deconvolution of H&E stains. Histologic stains of liver samples were collected after systemic saline injection followed by FUS exposure (negative control, FIG. 20 panels: a-d) or GV injection and sonication (FIG. 20 panels: e-h). Color deconvolution was applied to H&E stains of liver sections (panels: a, e) to create separate red blood cell (FIG. 20 panels: b, f) and tissue (panels: c, g) images. The residual un-mixed images are presented in (FIG. 20 panels: d, h). Necrotic regions in the H&E images (panel: e, zoom-in in panel: i) were found around hemorrhagic foci (FIG. 20 panel: f, zoom-in in FIG. 20 panel: j) in the livers of mice injected with gas vesicles following focused ultrasound exposure. Scale bar is 2 mm (FIG. 20 panels: d, h), 200 µm (panel: j).

DETAILED DESCRIPTION

Provided herein are methods as well as compositions and systems for performing the methods, for creating cavitation at a target site using gas vesicles and ultrasound, and uses thereof.

The wordings "Gas Vesicles", "gas vesicles protein structure" or "GV", "GVP" or as used herein refer to a gas-filled protein structure intracellularly expressed by certain bacteria or archaea as a mechanism to regulate cellular buoyancy in aqueous environments. See, for example, U.S. Pat. No. 10,493,172, entitled "Gas-Filled Structures and Related Compositions, Methods and Systems to Image a Target Site" by Lakshmanan et al., the contents of which are incorporated by reference herein. GV are typically nanostructures with widths and lengths of nanometer dimensions (in particular with widths of 45-250 nm and lengths of 100-800 nm) but can have lengths up to 2 µm as will be understood by a skilled person.

The wording "GV type" in the sense of the disclosure indicates a gas vesicle having dimensions and shape resulting in distinctive mechanical, acoustic, surface and/or magnetic properties as will be understood by a skilled person upon reading of the present disclosure. In particular, a skilled person will understand that different shapes and dimensions will result in different properties in view of the indications in provided in U.S. application Ser. Nos. 15/613,104 and 15/663,600 and additional indications identifiable by a skilled person. A GV type can be provided naturally occurring or engineered Gas Vesicle Gene Cluster (GVGC) comprising the Gas Vesicle Assembly (GVA) genes and Gas Vesicle Structural (GVS) genes required to form the GV type within a host cell prokaryotic or mammalian cell.

The Gas Vesicle Assembly genes encode for GVA proteins and are located in in a prokaryotic cell within one or more operons comprising at least one of a GvpN and a GvpF excluding any GvpA/B and GvpC gene possibly present within said one or more operons as described in details in U.S. application Ser. No. 15/663,635 filed on filed on Jul. 28, 2017 and incorporated by reference in its entirety. The Gas Vesicle Structural (GVS) genes encode GVS proteins are located in a prokaryotic cell within one or more operons that can be identified with reference to the consensus amino acid sequence of the encoded gvpA/B protein and gvpC protein sequences as described in details in U.S. application Ser. No. 15/663,635 filed on filed on Jul. 28, 2017 and incorporated by reference in its entirety.

The term "hybrid gene cluster" or "hybrid cluster" as used herein indicates a cluster comprising at least two genes native to different species and resulting in a cluster not natively in any organisms. Typically, a hybrid gene cluster comprises a subset of gas vesicle genes native to a first bacterial species and another subsets of gas vesicle genes native to one or more bacterial species, with at least one of the one or more bacterial species different from the first bacterial specie Accordingly, a hybrid GV gene clusters including a combination of GV genes which is not native in any naturally occurring prokaryotes.

The term "delivering" refers to placing the GV type from outside the target site to inside the target site.

A "delivery cell" as used herein is a cell, for example bacteria, archaea, or mammalian cell, naturally or engineered to be capable of carrying a GV type within it. In an embodiment, a delivery cell can express the GV type. A delivery cell that expresses the GV type can express the GV type naturally or it can be engineered to express the GV type.

The term "target site" as used herein indicates an environment comprising one or more cavitation targets. The term "cavitation target" refers to a structure or a combination of structures and fluids intended to be affected by the cavitation, such as a target material, target cells, target tissue, or a target solid formation. Accordingly, the term "target site" can refer to an organ, a in vitro container, or other medium/ container known in the art. In particular, the term "target site" can refer to biological environments such as cells, tissues, organs, in vitro, in vivo, or ex vivo that contain at least one target. Accordingly, a cavitation target can include any molecule (organic or inorganic), physical structure (living or non-living), cell, tissue, body part, body cavity, organ system, whole organisms, collection of any number of organisms within any suitable environment in vitro, in vivo or ex vivo as will be understood by a skilled person. Accordingly, exemplary target sites include collections of microorganisms, including, bacteria or archaea in a solution in vitro, as well as cells grown in an in vitro culture, including, primary mammalian, cells, immortalized cell lines, tumor cells, stem cells, and the like. Additional exemplary target sites include tissues and organs in an ex vivo culture and tissue, organs, or organs systems in a subject, for example, lungs, brain, kidney, liver, heart, the central nervous system, the peripheral nervous system, the gastrointestinal system, the circulatory system, the immune system, the skeletal system, the sensory system, within a body of an individual and additional environments identifiable by a skilled person. The term "individual" or "subject" or "patient" as used herein in includes a single plant or animal and in particular higher plants or animals and in particular vertebrates such as mammals and more particularly human beings.

The term "ultrasound" refers to sound with frequencies higher than the audible limits of human beings, herein taken to be frequencies over 20 kHz. Ultrasound devices typically can range up to the gigahertz range of frequencies, with most diagnostic medical ultrasound devices operating in the 1 to 18 MHz range. Therapeutic ultrasound devices operate at lower frequencies, typically ranging between 0.2 to 3 MHz. An "ultrasound pulse" in the sense of the disclosure refers to a single sonic disturbance of a medium with a center frequency in the ultrasonic range, or a plurality of such pulses. In embodiments, applying an ultrasound pulse has a peak positive pressure indicating pressure higher than the normal pressure of the medium, a peak negative pressure indicating pressure lower than the normal pressure of the medium, a center frequency ($f_o$), and a pulse duration or "pulse length".

As used herein, "frequency" refers to the center frequency ($f_o$) of the applied ultrasound. As used herein, "amplitude" refers to the peak positive or negative pressure of the applied ultrasound. The applied ultrasound can be symmetric (peak positive pressure equal to peak negative pressure) or asymmetric. For descriptions of collapse pressure, "collapse amplitude" refers to peak positive pressure. For descriptions of cavitation pressure, "cavitation amplitude" refers to peak negative pressure. As used herein, "pulse length" refers to the duration the ultrasound is applied at the given amplitude, measured in terms of time or number of cycles. As used herein, "duty cycle" refers to the percentage of time the applied ultrasound is at the given amplitude. As used herein, "mechanical index" (MI) refers to a characteristic of the applied ultrasound measured as the peak negative pressure divided by the square root of the frequency in [MPa/MHz^0.5]. The applied ultrasound can be designed in shape both spatially and temporally as needed for the application.

Figure 1:
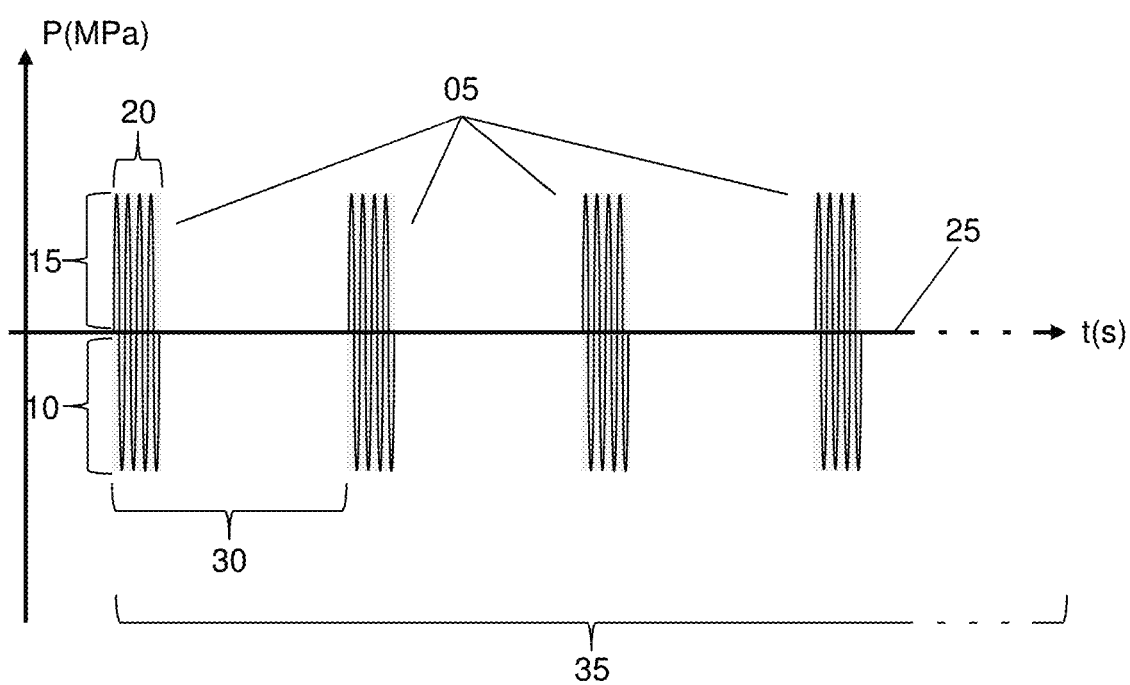

FIG. 1 shows an example of ultrasound pulses. Each pulse (05) has a pulse length (20), which can be measured in cycles or units of time, a peak positive pressure (15) and a peak negative pressure (10), both of which can be measured in Pascals, or more conveniently in megaPascals (MPa). The positive and negative pressures are measured with respect to the background pressure (25). The duty cycle is the percent ratio of pulse length (20) over the pulse repetition interval (30), or ((pulse length)/(pulse repetition interval)*100). The overall duration of the pulse sequence (35) equals the pulse repetition interval (30) times the number of pulses. For simplicity, the figure shows each pulse having a single frequency. In practice the pulses will include a range of frequencies, but with one dominant or "center frequency".

The term "collapse" as used herein refers to the opening, fragmentation, or fracturing of the GV such that the gas is released to the surrounding fluid, allowing bubble formation.

The term "collapse threshold" as used herein is a point selected on the collapse pressure profile of the GV type. A collapse pressure profile as used herein indicates a range of pressures over which collapse of a population of GVs of a certain type occurs. The critical collapse pressure profile of a GV is functional to the mechanical properties of the protein shell and the diameter of the shell structure. In particular, a collapse pressure profile in the sense of the disclosure comprise increasing acoustic collapse pressure values, starting from an initial collapse pressure value at which the GV signal/optical scattering by GVs starts to be erased to a complete collapse pressure value at which the GV signal/optical scattering by GVs is completely erased. The collapse pressure profile of a set type of GV is thus characterized by a mid-point pressure where 50% of the GVs of the set type have been collapsed (also known as the "midpoint collapse pressure"), an initial collapse pressure where 5% or lower of the GVs of the type have been collapsed, and a complete collapse pressure where at least 95% of the GVs of the type have been collapsed. In embodiments herein described collapse threshold can be any of these collapse pressures within a collapse pressure profile, as well as any point between them. See, for example, U.S. Pat. No. 10,493,172 incorporated by reference herein.

As used herein, the term "cavitation" refers to activity in which rapid changes in pressure in a liquid cause the oscillation and/or collapse of small cavities (bubbles) filled with gas (vapor). Inertial cavitation refers to an eventual violent destruction (fragmentation, collapse) of bubbles after expanding to at least twice their diameter. Stable, or non-inertial, cavitation refers to a sustained oscillation of the bubble's dimensions.

As used herein, the term "therapeutic cavitation" refers to the use of cavitating GV created nanobubbles to cause a mechanical change in some tissue or cell (e.g. lysing). Therapeutic cavitation can be therapeutic, for example, in using the mechanical energy of the cavitation to destroy unwanted tissue at a target site. It can also, for example, refer to the lysing of a delivery cell (or, more likely, a group of cells) from the inside in a way that the cells' destruction destroys unwanted tissue at a target site. It can also, for example, refer to the lysing of a delivery cell or cells from the inside such that a pre-determined substance (e.g. drug) is released from the cell at a target site. For example, FIG. 18C, panels e-h show how systemic injection of 200 uL of OD500=37 of GVs allows cell lysis and hemorrhage. Assuming that the average weight of a mouse liver is 2-3 g, and assuming perfect mixing and full accumulation in the liver, there will be a GV concentration equivalent to OD500=2.4-3.7 or 1.44-2.22 Nm in the liver tissue. In another example, FIG. 10 shows GV expressing cells with 20-40% of the cell volume on average filled by GVs facilitating selective lysis of these cells. It is important to note that the expression of GVs and the cell size differ dramatically between cells.

As used herein, "lysing" refers to causing the disintegration of a cell by rupturing the cell's membrane. In cavitation, lysing is caused by mechanical stress effects of the cavitation either directly (e.g. bubbles cavitating near cell walls imparting physical pressure forces on the membrane) or indirectly (e.g. bubbles cavitating within a delivery cell causing the delivery cell to lyse near the target cell, the physical pressure forces of the lysing of the delivery cell lysing the target cell). Lysing can be performed on a single cell or on multiple cells at the same time.

The term "mechanical stress" as used herein indicates a physical quantity that expresses the internal forces that neighboring particles of a cavitation target exert on each other, while "strain" is the measure of the deformation of the cavitation target. Strain in an object can arise by stress from contact or friction forces to its surface from another object or fluid.

As used herein, "proximity" refers to any of embedding into, attaching to, touching, or being in effective range of. For cavitation, effective range is variable based on the target composition and the desired effect, but generally is within 6 µm of the target (see e.g. Qin, Peng, et al. "Effect of non-acoustic parameters on heterogeneous sonoporation mediated by single-pulse ultrasound and microbubbles." Ultrasonics sonochemistry 31 (2016): 107-115).

As used herein, the term "target compound" or "payload" refers to a pre-determined substance to be released from a GV-expressing delivery cell after cellular lysing of the delivery cell by cavitation.

The term "contrast enhanced imaging" or "imaging", as herein indicates a visualization of a target site performed with the aid of a contrast agent administered to the target site to improve the visibility of structures or fluids by devices process and techniques suitable to provide a visual representation of a target site. Accordingly contrast agent is a substance that enhances the contrast of structures or fluids within the target site, producing a higher contrast image for evaluation.

The term "ultrasound imaging" or "ultrasound scanning" or "sonography" as used herein indicate imaging performed with techniques based on the application of ultrasound. Accordingly, the wording "ultrasound imaging" as used herein refers in particular to the use of high frequency sound waves, typically broadband waves in the megahertz range, to image the target site. See for example U.S. Pat. No. 10,493,172 incorporated by reference herein. Passive acoustic mapping (PAM) is an imaging tool for monitoring cavitation activity during focused ultrasound therapy. PAM comprises recording (listening) the acoustic emissions from cavitating bubbles while they vibrate under focused ultrasound pressure field (as in passive acoustic detection) as will be understood by a skilled person. Passive acoustic detection (PCD) is a sensing tool for monitoring cavitation activity at a specific location or region during focused ultrasound therapy that doesn't involve forming a spatial cavitation map.

The term "magnetic resonance imaging" or "MRI" as used herein indicates an imaging technique performed by applying a magnetic field to a target site and detecting the resulting magnetic resonance of the GV type. See for example U.S. application Ser. No. 15/633,600 entitled "Gas-Filled Structures And Related Compositions, Methods And Systems For Magnetic Resonance Imaging" incorporated by reference herein.

Figure 2:
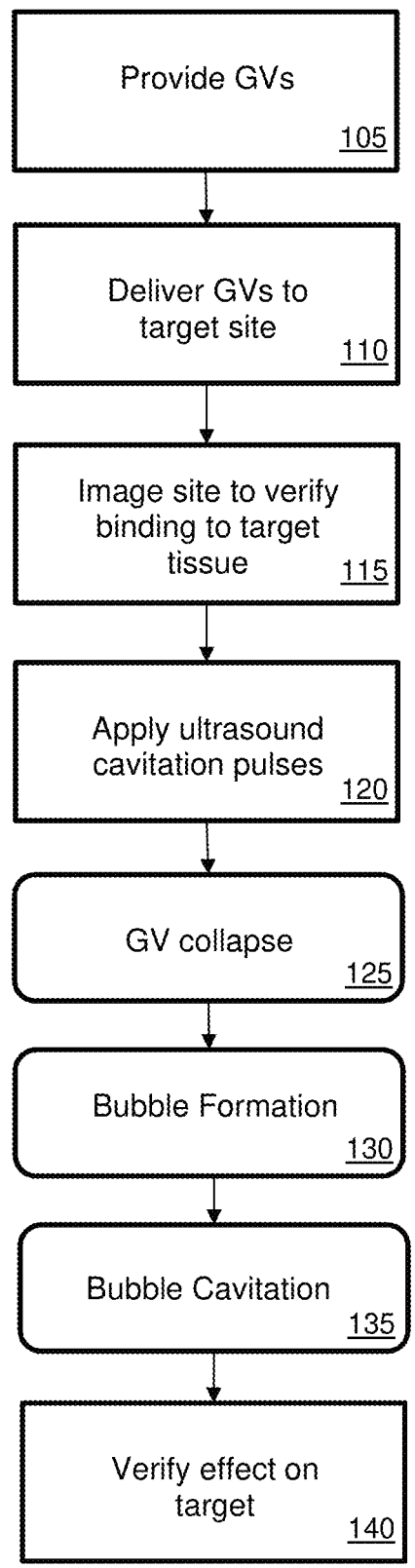

FIG. 2 provides an example method for using GVs for therapeutic cavitation, further comprising imaging steps to verify delivery of GVs and the effect of the cavitation. First, GVs are provided (105); for example, by taking previously engineered GVs or engineering and expressing new GVs. These GVs can be delivered to the target site (110), either by delivering in a purified form after being expressed or by delivering the cells that express the GVs. Examples of delivery methods include injection and ingestion (e.g. pill). Imaging (115) can then be used to determine when the GVs are present at the target site and bound to the target receptors. Any non-destructive (does not cause collapse of the GVs) imaging technique can be used, including B-mode ultrasound, amplitude modulation ultrasound, optical coherence tomography (OCT), MRI, etc. Imaging can be done with the GVs as the contrast agent, or with a separate contrast agent (including other GVs) being mixed in with the functionalized GVs. Once a sufficient number of GVs are confirmed to be bound to the target (e.g. estimated to create enough mechanical stress to the target site), an ultrasound pulse (or series of pulses, typically) can be applied to the site (120). The ultrasound pulses first collapse the GVs (125) through positive pressure effects. The collapsing GVs release the gas held in them, creating bubbles (130) at the site. The ultrasound pulses then cavitate the bubbles (135), creating the desired effect at the site. Further imaging can be used to verify that the GVs have collapsed and that the target has undergone the desired mechanical transformation (e.g. lysing of cells) (140).

Some advantages of using GV based cavitation over traditional microbubble, nanodroplet, or nanocup methods in a biological environment and in particular human body include:

GV stability, meaning that the delivery system can extend over a longer period of time (for example, microbubbles dissolve within minutes of administration);

GVs are small, so they can more easily reach many capillaries for an overall amount of gas;

GVs can be imaged without activation (collapse) using ultrasound—nanodroplets only have ultrasound contrast after vaporization;

unlike nanocups, GVs can be degraded in the body and can be deactivated by inducing collapse.

In embodiments herein, gas vesicles may be delivered to a target site to serve as nuclei for bubble formation, for cavitation at the target site.

A GV type can be provided from gene expression from a Gas Vesicle Gene Cluster (GVGC) comprising the Gas Vesicle Assembly (GVA) genes and Gas Vesicle Structural (GVS) genes required to form the GV type within a host cell prokaryotic or mammalian cell. The GVGC can be naturally occurring or engineered.

The Gas Vesicle Assembly genes encode for GVA proteins and are located in a prokaryotic cell within one or more operons comprising at least one of a GvpN and a GvpF excluding any GvpA/B and GvpC gene possibly present within said one or more operons as described in details in U.S. application Ser. No. 15/663,635 filed on filed on Jul. 28, 2017 and incorporated by reference in its entirety. The Gas Vesicle Structural (GVS) genes encode GVS proteins are located a prokaryotic cell within one or more operons that can be identified with reference to the consensus amino acid sequence of the encoded gvpA/B protein and gvpC protein sequences as described in details in U.S. application Ser. No. 15/663,635 filed on filed on Jul. 28, 2017 and incorporated by reference in its entirety.

For example, in one exemplary embodiment, all the gyp genes B, N, F, G, L, S, K, J and U are from *B. megaterium*. Mega GVs are typically cone-tipped cylindrical structures with a diameter of approximately 73 nm and length of 100-600 nm, encoded by a cluster of eleven or fourteen different genes, including the primary structural protein, gvpB, and several putative minor components and putative chaperones as would be understood by a person skilled in the art.

Reference is made in this connection to the methods to identify and select a functional hybrid GVGC described in U.S. application Ser. No. 15/663,665 entitled "Genetically Engineered Gas Vesicle Gene Clusters, Genetic Circuits, Vectors, Prokaryotic Cells, Compositions, Methods And Systems For Contrast-Enhanced Imaging" filed on Jul. 28, 2017 and U.S. application Ser. No. 16/736,683 entitled "Mammalian Expression of Gas Vesicles As Acoustic Reporter Genes" filed on Jan. 7, 2020 filed on incorporated herein by reference in its entirety. The GVs herein described can be GVs naturally expressed by bacteria or archaea. The GVs can be GVs expressed by cells genetically modified to contain a GV gene cluster adapted from another organism to express a natural GV type. The GVs can also expressed by cells genetically modified to contain a hybrid GV gene cluster comprising a combination of Gyp genes that are natively encoded in GV gene clusters from two or more different organisms.

A detailed description how to select native GVA (GV structural protein) and GVS (GV shell protein) genes in view of a specific GV type to be formed in a prokaryotic host can be found in U.S. Ser. No. 15/663,635, which is incorporated herein by reference in its entirety. In particular, a skilled person will be able to select native GVA and GVS genes according to an experimental design and engineer a hybrid GV gene cluster encoding the GV type in a configuration allowing co-expression in the prokaryotic host.

In some embodiments, the gene cluster is selected according the one or more of the following parameters: in situ expression capabilities, collapse pressure at the desired frequency, and stability of expression without mutations (low burden and toxicity). These parameters can be evaluated using the methodology shown in FIG. 6.

Different GV types have different shapes and dimensions depending on the GVGC providing the GV type naturally occurring or hybrid (Ref: U.S. application Ser. No. 15/663, 635). For example, GV type in the sense of the disclosure can be substantially spherical, ellipsoid, cylindrical, or have other shapes such as football shape or cylindrical with cone shaped end portions depending on the type of bacteria providing the gas vesicles. Different GV types can have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 10 nm or less. For example, the average diameter of the gas vesicles may range from 10 nm to 1000 nm, such as 25 nm to 500 nm, including 50 nm to 250 nm, or 100 nm to 250 nm. By "average" is meant the arithmetic mean.

In embodiments herein, GV delivery to the target site can be accomplished in one of two forms. One is to express the GVs in cells outside the target site (e.g. in vitro), and other is to deliver the GV expressing cells (delivery cells) to the target site.

For expressing the GVs in cells outside the target site, GV expressing cells are selected from cells that naturally produce GVs or from cells that have been engineered to have a GV producing hybrid cluster. In some embodiments, the GV producing cells are designed to be externally induced to express the GVs (for example, by chemical or thermal triggers), the cells are lysed, and the GVs are purified then placed in a delivery medium (e.g. solution, gel, etc.). In some embodiments, the delivering can be performed by providing an isolated GV type and contacting the isolated GV type with the target site can be performed by introducing the isolated GV type into the target site to allow the isolated GVs come in proximity to the cavitation target in the target site. In some embodiments, providing an isolated GV type can be performed by expressing the GV type in a cell in vitro, lysing the cell to release the GVs, and purifying the GVs to provide the isolated GV type. In some embodiments delivering the GV type includes injecting the GV type into the blood stream and waiting for the GV type to accumulate in the target site.

In methods herein described and related compositions and systems, delivering the GV type to the target site can be performed in vitro or ex vivo by placing the GV type or the cell expressing the GV type at the target site, for example by providing a solution containing the GV type and/or a cell to provide capability of expressing the GV type and introducing the solution to the target site. In methods herein described and related compositions and systems, delivering the GV type in vivo can be performed under conditions that depend on the nature of the target site. For example, administering to subcutaneous target site can comprise placing the purified GV type or cells containing the GV type (delivery cells, e.g. cells that express the GV type) in a solution that is injected into the site, or in a fluid pathway leading to the site, for example systemic injection into the blood stream. For example, a target site might be accessible by digestion, so an ingestible liquid, gel, or solid can be used (e.g. pill) to administer the GV type or cell expressing the GV type to the target site. In some cases, in vivo administration can require a surgical incision. Other means of administering a substance (like GV types or delivery cells) to a target site would be known to one skilled in the art. The target site contains the cavitation target, e.g. the cells to be effected by the cavitation. The cavitation target can be a tumorous cell, for example. In some embodiments, the expression is constitutive (e.g. from an always-on promoter such as CMV or EF1alpha). In some embodiments, the expression is connected to an endogenous promoter that gets turned on under certain conditions (for example, the NFAT promoter in a T-cell becoming turned on when the T-cell is activated or the ARG1 promoter in a macrophage becoming turned on when the macrophage enters into an immunosuppressed state).

Naturally, the GV type needs to be expressed and folded prior to the application of the ultrasound pulse. Therefore, the delivering the delivery cell includes allowing enough time for the GV type to be expressed and providing the conditions required to allow the GV type to be expressed during that time. The time and conditions depend on the particular GV type to be expressed. For example, for in situ expression of GVs in bacteria that colonize tumors, give the cells three days after systemic injection to colonize the tumor. Then, induce one a day for four days before cavitating the GVs. However, note that it has been shown that a GV signal can be detected even after a single day of induction.

Figure 6:
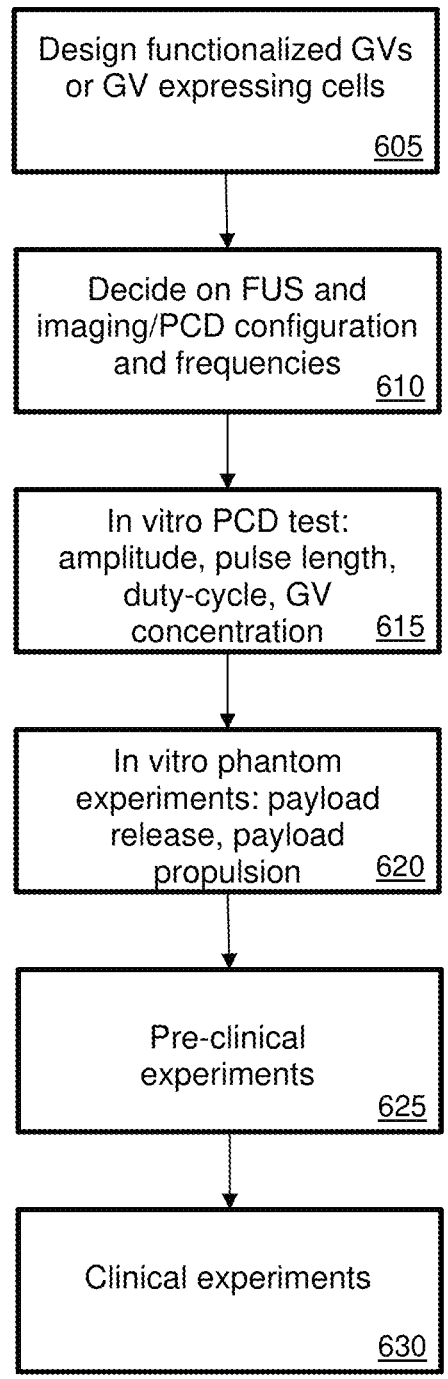
FIG. 6 shows an example method of determining and validating the ultrasound parameters used for GV cavitation.

In order to effect therapeutic cavitation, the delivering the GV type includes delivering a sufficient number of GVs for therapeutic cavitation. By placing a sufficient number of bubbles close to tissue (e.g. cell walls), this inertial cavitation can damage or destroy, by the mechanical effects of cavitation, parts of that nearby tissue while leaving more distant tissue unharmed. Note that bubbles do not necessarily fracture immediately after inertial cavitation starts, so the damage the bubbles produce while undergoing inertial cavitation can be extended over a short period of time. The number of bubbles (and hence GVs) required to effectively damage a site depends on the nature of the tissue at the site. Generally, the greater number of GVs used, the greater number of bubbles produces, and therefore the greater the energy provided towards damaging the tissue. A single GV can be used to create a single bubble that can undergo cavitation, but most practical applications will require more as will be understood by a skilled person. The amount of gas contained by the GVs should be selected be high enough to support cavitation at the desired condition. For example, low expression of GVs in mammalian vs. bacterial cells required higher pressure for achieving cavitation. For targeted GVs: if molecular selectivity of cavitation activity is needed, the GVs need to be able to arrive at their target and accumulate there, while being practically absent from the surrounding tissue during the insonation. The GV degradation rate is preferably matched. Increasing attached GV concentration at the target can be achieved by increasing the dose of injected GVs of by tuning their coating or GvpC structure. In the case of RGD, for example, one can choose between several variants of this peptide, with different linkers that have different attachment efficiencies. Depending on the GV type used, the environment the GVs are used in, and the ultrasound parameters, the number of GVs present can create acoustic shadowing (see Example 1, FIG. 10). This can lead to gradual depth-dependent GV collapse and an inward going "cavitation wave." One can control the expression of GVs either by changing the concentration of inducer or adapting the gene circuit based on pre-clinical experiments, for example as shown in FIG. 6.

GVs have longer lifespans in vivo and ex vivo than most other forms of cavitation nuclei. Purified GVs can survive for months and years at 4 degC before GvpC dissociates from Ana GVs. Inside the body, most systemically injected GVs will be degraded by the liver less than an hour. This degradation is a result of macrophages in the liver being able to engulf and digest GVs. However, a persistent gas vesicle signal can be seen after subcutaneous injection for 2 hours. These GVs were not in contact with macrophages and were not degraded during that time window.

In order to ensure the bubbles cavitate close to the target cell, some embodiments of methods and systems that include delivering the GV type in proximity of the cavitation target (e.g. target cell to be effected by the cavitation) also includes, for purified GVs, the GV type being functionalized to include binding tags on the GV capable to bind to a target molecule presented on the cavitation target (e.g. a receptor protein presented on the cell walls of a cavitation target cell) as described in GV type as described in U.S. Ser. No. 15/663,635 filed on Jul. 28, 2017 incorporated by reference in its entirety. This proximity allows the GV type to serve as ultrasound-triggered disruptors of the plasma membrane, causing cell death and creating therapeutic benefits such as making the interior of the target cells more accessible to synergistic drugs and discovery by the immune system In embodiments herein, functionalizing the GV type can include genetically modifying the Gyp protein. One or more protein tags can be added through genetic modification of a GvpC protein or a variant thereof by fusing a gene encoding the one or more protein tags to the gvpC gene (including variants GvpC protein described in U.S. application Ser. No. 15/663,665 incorporated herein by reference in its entirety). In particular, in some embodiments herein described, one or more protein tags can be added through genetic modification of a GvpC protein or a variant thereof in accordance with the present disclosure of a set type of GV. As examples, affinity tags can be used to separate the engineered GvpC as part of producing arginine-glycine-aspartate (RGD) tagged GVs: RGD can be used for binding to cancer cells, but other tags can be used for binding to cells, specific locations, or other GVs. Ana GVs can be clustered stripped using Amine-Reactive Crosslinker (NHS) chemistry directly to GvpA. NHS chemistry can also be used for binding GVs together or adding fluorophores to them (see e.g. Lakshmanan, Anupama, et al. "Preparation of biogenic gas vesicle nanostructures for use as contrast agents for ultrasound and MRI." Nature protocols 12.10 (2017): 2050). An example of functionalization includes streptavidin-functionalization to attach to HER2 receptors of antibodies.

In embodiments using a delivery cell, the delivery cell can be chosen, or engineered, to have an affinity for the target. For example, T-cells and macrophages go to the rims of tumors, while some bacteria can home in on tumors and colonize deep inside them. In some embodiments, the delivery cells are functionalized to bind to a cavitation target. For example, CAR-T cells engineered to be delivery cells can bind to tumor cells.

In embodiments using a delivery cell, the cell can be additionally engineered to facilitate use. For example, the delivery cell membrane can be weakened to aid the lysing from cavitation.

In order to verify that the GVs are at the target site, the methods can further include a step of imaging the target site before and/or during cavitation. Imaging can be done with ultrasound, MRI, or other means. In order to prevent collapse of the GV type prior to the application of the collapse pulse, ultrasound imaging is performed at a pressure below the collapse threshold of the GV type. In some embodiments, the GVs used for cavitation can also be used as contrast for ultrasound imaging. In other embodiments, contrast agents other than the GV type can be used mixed in with the GV type. This can include another GV type, for example an imaging GV type that has a collapse threshold lower than the collapse threshold of the GV type used for cavitation. In that way, the imaging GV type can be collapsed for imaging without inferring with the cavitation. In some embodiments, a GV type can be functionalized with fluorescent molecules to allow imaging. Any non-destructive (does not cause collapse of the functionalized GVs) imaging technique can be used, including B-mode ultrasound, amplitude modulation ultrasound, optical coherence tomography (OCT), MRI, etc. Imaging can be done with the functionalized GVs as the contrast agent, or with a separate contrast agent (including other GVs) being mixed in with the functionalized GVs.

Another method of non-destructive ultrasound imaging is to perform differential imaging between the location before GVs are introduced and after the GVs are introduced, using ultrasound pressures below the collapse threshold of the GVs. Using this method, the imaging GVs and the cavitation GVs can be the same GVs (same types).

Methods and systems to create cavitation herein described further comprise applying an ultrasound pulse to the target site after the delivering, the applying ultrasound pulse having a positive pressure above the collapse threshold of the GV type and a negative pressure and pulse length sufficient to cavitate bubbles released by the GV type after collapse. In some embodiments, applying an ultrasound pulse is accomplished by sending strong, short electrical pulses to a piezo-electric transducer directed at the target site. An ultrasound pulse can have amplitudes (positive and negative pressure) and a center frequency that is considered "inert" (nondamaging) for in vivo use, such that the damage to the target site is performed, if at all, by the cavitation and not directly by the applied ultrasound.

In embodiments, the center frequency, amplitudes (positive and negative pressure), pulse duration, duty cycle, and number of pulses of the ultrasound pulse can be controlled by adjusting settings on the device producing the ultrasound based on the needs of the particular task, for example collapsing GVs and causing cavitation (positive pressure above the collapse threshold, high negative pressure, long pulse length) or imaging the GVs (positive pressure below the collapse threshold and shorter pulse length).

Figure 3:
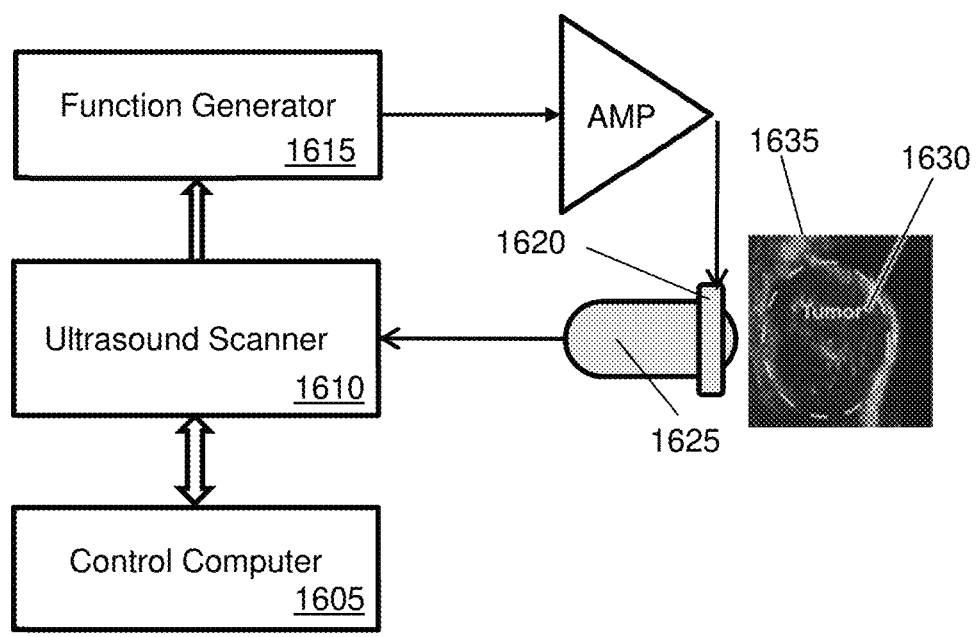
FIG. 3 illustrates an exemplary focused ultrasound (FUS) system with passive-acoustic mapping using linear arrays.

FIG. 3 shows an example setup for focused ultrasound (FUS). A control computer (1605) controls the parameters and receives image data from an ultrasound scanner (1610). The ultrasound scanner (1610) receives data from one or more linear arrays (1625) situated at different angles to the target site (1630). The ultrasound (1610) triggers a function generator (1615) to generate shaped ultrasound from a transducer (1620), providing a focused volume of ultrasound response within the region of interest (1635). In some embodiments focused ultrasound is used. In some embodiments, the ultrasound is not focused. In both cases, the location of the cavitation is determined by the distribution of GVs within the tissue exposed to ultrasound having sufficient pressure for collapse and cavitation.

In PAM (passive acoustic mapping), the cavitating bubbles also behave as acoustic sources, and since their emissions encompass large spectral ranges, they can be separated from the original low frequency FUS signal. Then, the signals recorded in each of the "listening" elements of the higher frequency imaging transducer can be integrated to form a spatiotemporal map or the cavitation activity.

In embodiments of the present disclosure, the ultrasound pulse used for cavitation is applied at a positive pressure (collapse amplitude) at least as high as the collapse threshold of the GVs. This is distinguished from non-destructive (non-GV collapsing) imaging, which has to use a positive pressure below the collapse threshold. In embodiments of methods herein described and related systems and compositions, amplitudes, number and duration of pulses are selected based on the GV type used. Generally speaking, to collapse GV types with stronger shells (higher collapse thresholds), one needs to use higher collapse amplitudes and lower frequencies.

Exemplary Acoustic collapse pressures for GV type are reported in Table 1 below from U.S. application Ser. No. 16/736,681 filed on Jan. 7, 2020 incorporated by reference in its entirety

TABLE 1

Exemplary Gas Vesicle

| Gas Vesicle Type | gvp genes of the Gene Cluster forming Gas Vesicle | Acoustic Collapse Pressure |
|---|---|---|
| Naturally ooccuring in *B. megaterium* | Mega-gvpB, Mega-gvpN Mega-gvpF, Mega-gvpG, Mega-gvpL Mega-gvpS, Mega-gvpK, Mega-gvpJ, Mega-gvp-R, Mega-gvp-T and Mega-gvpU | 1.9 MPa |
| Engineered | Mega-gvpB, Mega-vpN Mega-gvpF, Mega-gvpG, Mega-gvpL Mega-gvpS, Mega-gvpK, Mega-gvpJ, and Mega-gvpU | 1.9 MPa |
| Naturally ooccuring in *Anabaena flos-aquae* | Ana-gvpA, Ana-gvpC, Ana-gvpN, Ana-gvpJ, Ana-gvpK, Ana-gvpF, Ana-gvpG, Ana-gvpV, Ana-gvpW | 0.9 MPa |

TABLE 1-continued

Exemplary Gas Vesicle

| Gas Vesicle Type | gvp genes of the Gene Cluster forming Gas Vesicle | Acoustic Collapse Pressure |
|---|---|---|
| Engineered | Ana-gvpA, Ana-gvpN, Ana-gvpJ, Ana-gvpK, Ana-gvpF, Ana-gvpG, Ana-gvpV, Ana-gvpW | 0.6 MPa |
| Hybrid engineered | Ana-gvpA gen, Mega-gvpR, Mega-gvpN, Mega-gvpF, Mega-gvpG, Mega-gvpL, Mega-gvpS, Mega-gvpK, Mega-gvpJ, gvpT and gvpU | 0.6 MPa |
| Hybrid engineered | Ana-gvpA, Ana-gvpC, Mega-gvpN Mega-gvpF, Mega-gvpG, Mega-gvpL Mega-gvpS, Mega-gvpK, Mega-gvpJ, and Mega-gvpU | 2.2 MPa |
| Hybrid engineered | Ana-gvpA, Ana-gvpC, Mega-gvpN Mega-gvpF, Mega-gvpG, Mega-gvpL Mega-gvpR Mega-gvpS, Mega-gvpT Mega-gvpK, Mega-gvpJ, and Mega-gvpU | 2.2 MPa |
| Hybrid engineered | Ana-gvpA, Ana-gvpC Ana-gvpN; Mega- Mega-gvpF, Mega-gvpG, Mega-gvpL Mega-gvpS, Mega-gvpK, Mega-gvpJ, and Mega-gvpU | 2.2 MPa |
| Hybrid engineered | Ana-gvpA, Ana-gvpC Ana-gvpN; Mega- Mega-gvpF, Mega-gvpG, Mega-gvpL Mega-gvpR, Mega-gvpS, Mega-gvpT, Mega-gvpK, Mega-gvpJ, and Mega-gvpU | 2.2 MPa |

Additional collapse pressure for specific can be found by a skilled person upon reading of the present U.S. application Ser. No. 15/613,104 filed on Jun. 2, 2017 and patented as U.S. Pat. No. 10,493,172 incorporated herein by reference in its entirety.

When the GVs are collapsed, the released gas creates nanobubbles. In most cases, the nanobubbles can combine to form larger microbubbles. These bubbles are then cavitated by the ultrasound pulses that were used to collapse the GVs. Typically, larger bubbles produce greater damage for an equal distance (see e.g. Qin, Peng, et al. "Effect of non-acoustic parameters on heterogeneous sonoporation mediated by single-pulse ultrasound and microbubbles." Ultrasonics sonochemistry 31 (2016): 107-115.

In order to cavitate the bubbles formed from the gas released by the collapse of the GV type, the ultrasound pulse is applied with a pulse duration sufficient to cavitate the bubbles.

The mechanical stress caused by cavitation in proximity of any cavitation target accordingly can cause damage to the cavitation target as will be understood by a skilled person. Even significant stress may exist even when deformation is negligible or non-existent (a common assumption when modeling the flow of water), mechanical stress typically results in deformation, movement, damage and/or disruption of a target structure. In some embodiments herein, ultrasound passive cavitation detection (PCD) is used to give quantitative cavitation measurements and/or indicate bioeffects of the cavitation. See e.g. Smith, Cameron A B, and Constantin C. Coussios. "Spatiotemporal assessment of the cellular safety of cavitation-based therapies by passive acoustic mapping." Ultrasound in Medicine & Biology (2020).

Cavitation activity caused by ultrasound is dependent on the features of the ultrasound wave. Five ultrasound parameters connected with cavitation are amplitude, frequency, pulse duration, duty cycle, and number of ultrasound pulses applied. These parameters can be determined experimentally for a given application and GV type as will be understood by a skilled person. These parameters can determine if cavitation occurs and/or what type of cavitation occurs (stable vs. inertial). The type of cavitation is deterministic of what mechanical effects the cavitation will have on the cavitation target. For example, while inertial cavitation can be useful for destructive effects (e.g. lysing a cell wall, ablating cells, fractioning tissue structures, material dispersion), stable cavitation can be used to create microstreaming or gently open the membranes of cells (pinching/or pushing) or separate cells as part of a blood brain barrier opening. The mechanical index (MI) can also be considered as a useful parameter for cavitation control in terms of the degree of mechanical stress being applied, the MI being derived from the other parameters as discussed herein. The type of cavitation and its level can be assessed from PCD or PAM measurement. See e.g. the on-the-fly monitoring and control (1725) based on passive acoustic detection and mapping shown in FIG. 7.

See the example waveform of FIG. 1 with respect to the five parameters. The central parameters that control the resulting mechanical and thermal effects are discussed in this illustration. These parameters include the peak negative pressure (10), and the peak positive pressure (15). The peak negative pressure is central in determining the degree and type of cavitation while the peak positive pressure is important for causing GV collapse. During the on-time of the signal (20), bubbles cavitate and coalesce. Rectified diffusion and bubble disintegration to smaller bubbles are also possible under specific conditions. During the off time between the pulses, non-coated bubbles will gradually dissolve and heat will dissipate into the surrounding environment. In some embodiments, the duty cycle is kept below 5-10% (e.g. if mechanical effects are desired). In some embodiments, the duty cycle is kept above 5-10% (e.g. if thermal effects are desired). In some embodiments, the duty cycle for collapse and cavitation is higher than the duty cycle used for imaging techniques, for example above 0.2%.

In some embodiments, the negative pressure of the ultrasound pulses is used to distinguish the cavitation between inertial cavitation (bubble fragmentation) and stable cavitation (bubble oscillation), with lower pressure levels producing stable cavitation and higher pressure levels producing inertial cavitation. In some embodiments, the threshold between stable and inertial cavitation can be determined experimentally by determining at what cavitation amplitude there is no significant cavitation signal (see e.g. Example 1 FIG. 10, panel c) and selecting a first pressure value with significant (e.g. above 0.5 dB above the noise floor on average) harmonic signal as being a negative pressure sufficient for stable cavitation and selecting a second pressure value with significant (e.g. above 0.5 dB) non-harmonic or broadband signal and above the first pressure value as being a negative pressure sufficient for inertial cavitation. In some embodiments of methods herein described and related systems and compositions, the ultrasound pulse used for cavitation is applied at a negative pressure sufficient for the cavitation of the bubbles to be stable cavitation. In some embodiments this negative pressure is less than 0.6 MPa and greater than 0.2 MPa, at 0.67 MHz. In some embodiments of methods herein described and related systems and compositions, the ultrasound pulse used for cavitation is applied at a negative pressure sufficient for the cavitation of the bubbles to be inertial cavitation. In some embodiments, this negative pressure is at least 0.6 MPa at 0.67 MHz. In some embodiments, ultrasound pulses of frequencies below imaging frequencies are used for collapse and cavitation, for example below 2.5 MHz.

This is, however, for a specific center frequency. In some embodiments, the combination of center frequency and negative pressure amplitude relates to the distinction between inertial cavitation and stable cavitation, in terms of the mechanical index (MI). In general, higher MI results in inertial cavitation while lower favor stable cavitation. The specific threshold depends on the bubble size distribution and pulse length. For example, short imaging pulses should not result in cavitation activity without injecting cavitation nuclei below MI=1.9. Microbubbles will show inertial cavitation activity at MI values as lower as MI=0.4, and bubbles released from GVs will show similar activity at MI=0.5. See e.g. Example 1 and FIG. 10. There are no significant cavitation effects below MI=0.12 (e.g. 0.1 MPa at 0.67 MHz). In some embodiments of methods herein described and related systems and compositions, the ultrasound pulse used for cavitation is applied at an MI sufficient for the cavitation of the bubbles to be stable cavitation. In some embodiments this MI is less than 0.73, for purified GVs in solution at 0.67 MHz. In some embodiments of methods herein described and related systems and compositions, the ultrasound pulse used for cavitation is applied at an MI sufficient for the cavitation of the bubbles to be inertial cavitation. In some embodiments, this MI is at least 0.73, for purified GVs in solution at 0.67 MHz. In some embodiments where permanent damage to the target is desired, inertial cavitation is used. In some embodiments where permanent damage to the target is not desired, stable cavitation is used. In some embodiments, a MI higher than what is used for imaging is used, for example 2.8. For high MI, like 2.8 and above, the duty cycle can be below 0.2% as the likelihood of causing cavitation with a single pulse increases as the MI increases.

The applied frequency can change the collapse threshold of the GVs: GV collapse occurs in lower pressure levels at lower frequencies than they do at higher frequencies, which is a factor to consider when providing a GV type for cavitation. The following is an exemplary method to determine a collapse vs. applied pressure for a given frequency. Prepare an imaging phantom and embed the GV sample in it. One can use gel phantoms (1% agarose in PBS) with wells, and cast a mixture of GVs and agarose into these wells. Then, take a high frequency ultrasound image of the phantom at a pressure level that will not collapse any of the GVs. Then send short focused ultrasound pulses (FUS) at the tested frequency with increasing pressure and take an additional ultrasound image after each of these FUS pulses. Use pulses as short as possible to limit cavitation effects on the phantom. The change in the ultrasound signals measured from these GVs (taken from the high frequency images) as function of the FUS pressure gives the collapse curve. This process can be repeated at several relevant FUS frequencies. From these curves, one can engineer a cavitation method's frequency based on the GV type, or select a GV type based on the frequency to be applied. See the above described FIG. 3 for an example FUS setup.

In order to ensure inertial cavitation (in use for, for example, lysing a cell wall or other destructive effects), the ultrasound cavitation pulse is, in addition to being applied at a cavitation amplitude high enough for cavitation, also applied at a frequency low enough to produce inertial cavitation (e.g., having an MI over 0.73). Inertial cavitation causing ultrasound pulse frequencies range from 250 KHz to 3 MHz, most typically in a range below 1.5 MHz. A common therapeutic frequencies for cavitation are 0.5 and 0.67 MHz. As the mechanical index predicts, creating cavitation at lower frequencies demands lower pressure levels. In some embodiments, the center frequency of the ultrasound pulse used for cavitation is from 250 KHz to 1.5 MHz. In some embodiments, the center frequency of the ultrasound pulse used for cavitation is from 250 KHz to 3 MHz. In some embodiments, the center frequency of the ultrasound pulse used for cavitation is 0.67 MHz. Therefore, GV collapse occurs in lower pressure levels at lower frequencies than they do at higher frequencies, which is a factor to consider when providing a GV type for cavitation.

In embodiments of the present disclosure, the ultrasound pulse used for cavitation is maintained long enough to ensure that cavitation occurs, and the desired effect takes place, before the bubbles dissolve into the surrounding liquid. Bubble dissolution can take about 1 ms, however, its duration is largely dependent on the original bubble size (see e.g. WT Shi et al. "Destruction of contrast nanobubbles and the association with inertial cavitation", Ultrasound Med. Biol. 26(6):1009-19, July 2000). Therefore, a longer pulse length and/or a shorter pulse repetition interval generally corresponds to an increased cavitation effect (see Example 2 and FIGS. 13A-13B).

In embodiments of methods herein described and related systems and compositions the ultrasound pulse can be applied at a duty cycle that ensures that the dominant effects are mechanical (for example, if cavitation target is a cell and the cavitation is used for lysing a cell). To have a reasonable axial resolution, ultrasound imaging uses relatively short pulses of several cycles at most, typically lower than 0.1%. Higher duty cycles can be used for cavitation. Duty cycle values for cavitation are only limited by thermal effects that become dominant at 5-10%, which can reduce the efficiency of the mechanical (lysing) effects of cavitation. In some embodiments, the ultrasound pulse used for cavitation is applied at a duty cycle between 1% and 5%. In some embodiments, the ultrasound pulse used for cavitation is applied at a duty cycle between 0.1% and 5%. In some embodiments, the ultrasound pulse used for cavitation is applied at a duty cycle between 0.1% and 10%. The number of pulses needed to create an effective level of cavitation depends on many factors and can be determined experimentally by comparing the effect on samples with GVs cavitating compared to a control without using GV cavitation over a range of ultrasound application times. In some embodiments, the applying an ultrasound pulse comprises applying for at least 30 seconds.

The number of pulses needed to create an effective level of cavitation depends on many factors and can be determined experimentally by comparing the effect on samples with GVs cavitating compared to a control without using GV cavitation over a range of ultrasound application times. In some embodiments, the applying an ultrasound pulse comprises applying for at least 30 seconds. When using multiple GV types for cavitation, one can make sure that the cavitation of the more fragile GVs doesn't collapse the stronger GVs (local pressures can exceed the driving FUS pressure). This can be achieved by comparing ultrasound images of the GV mixture vas the fragile GVs after FUS exposure. To see if cavitation is maintained over several pulses, one can perform PCD measurements during each pulse and compare the measured signals. To determine if longer pulses are advantageous, see FIG. 6.

In embodiments wherein the cavitation target are cells, a large number of inertially cavitating bubbles near a cell wall can lyse the cell, depending on the number of bubbles present and the strength of the cell wall.

In some embodiments, methods and systems for lysing cells at the target site comprise delivering to a target site containing the target tissue a gas vesicle (GV) type having a GV type collapse threshold, the delivering performed to provide the GV type in proximity of the target cell; and applying a ultrasound pulse at to the target site after the delivering, the ultrasound pulse having a positive pressure, a negative pressure and a pulse duration, the positive pressure being above the collapse threshold of the GV type, the negative pressure and a pulse duration being sufficient to cavitate bubbles released by the GV type after collapse. an applied pressure above the collapse threshold of the GV type, the applied pressure sufficient to cavitate bubbles released by the GVs after collapse, the cavitated bubbles lysing the target cell.

In order to ensure the bubbles cavitate close to the target cell, some embodiments of methods and systems that include delivering the GV type in proximity of the target cell also includes the GV type being functionalized to include binding sites that bind to the target cell. The target cell can be a tumorous cell, for example. This proximity allows the GV type to serve as ultrasound-triggered disruptors of the plasma membrane, causing cell death and creating therapeutic benefits such as making the interior of the target cells more accessible to synergistic drugs and discovery by the immune system.

Figure 4:
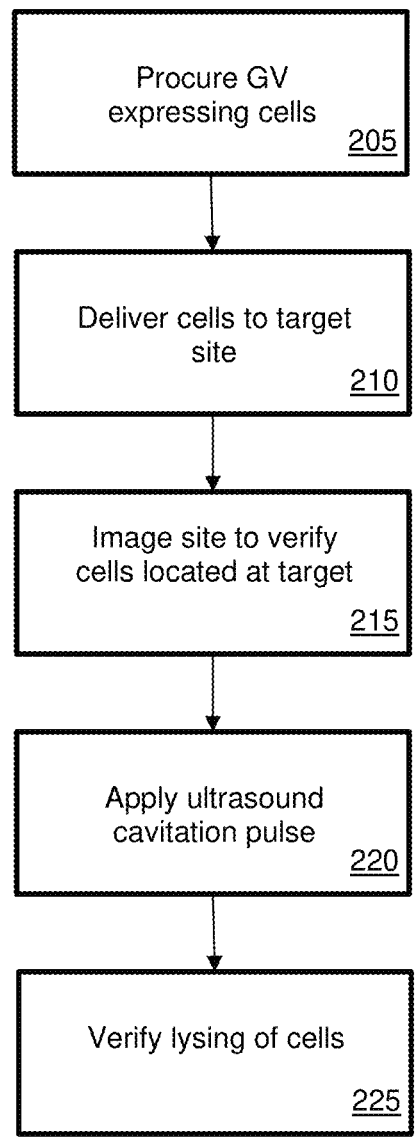
FIG. 4 shows an example method of using a GV expressing bacteria for therapeutic cavitation.

FIG. 4 provides an example method for using cell-expressed GVs for therapeutic cavitation. First, cells (bacteria, mammalian cells, archaea, etc.) that express the desired GVs for cavitation are provided (205). These can be taken from existing cells that have been properly engineered, or they can be newly engineered cells. The cells can also be engineered to express a specific protein that is desired to be delivered to the target site (such as a drug). The cells are delivered to the target site (210). Examples of delivery methods include injection and ingestion (e.g. pill). These "delivery cells" can then be induced to express the GVs. This can be by, for example, a chemical being introduced into the bloodstream or by a thermal switch. Imaging can then be used (215) to determine if the cells are located at the target site in sufficient quantity (enough for sufficient therapeutic effect). The imaging can also determine if the GVs were formed in the cells. As with functionalized GVs, the imaging would be non-destructive to the expressed GVs. An ultrasound pulse can then be applied (220) by ultrasound, causing the GVs to collapse in turn causing the GVs to release gas bubbles which then undergo inertial cavitation, the mechanical effect of which lyses the cells the GVs were expressed in. The sudden lysing of the cells can cause damage to surrounding tissue and/or allow the expressed proteins in the cells to be released into the target site. Imaging can then be applied again (225) to determine if the cell destruction was completed.

In some embodiments, methods and systems for lysing cells at the target site comprise delivering to a target site containing the target tissue a delivery cell containing a gas vesicle (GV) type having a GV type collapse threshold, the GV type having a GV type collapse threshold the delivering performed for a time and under conditions allowing expression of the GV type in the cell; and when the delivery cell is in proximity of the target cell, applying a ultrasound pulse to the target site after the delivering, the ultrasound pulse having a positive pressure, a negative pressure and a pulse duration, the positive pressure being above the collapse threshold of the GV type, the negative pressure and a pulse duration being sufficient to cavitate bubbles released by the GV type after collapse, the cavitated bubbles lysing the delivery cell thereby lysing the target cell.

In some embodiments, a delivery cell is lysed by GV seeded cavitation in proximity to the target cell, the delivery cell seeding a cavitating bubble that opens the target cell and, without dissolving, continue vibrating under the ultrasound pulse to mechanically effect the target cell. In some embodiments, the delivery cell is selected for high GV expression per cell and large cell size. The probability of the delivery cell being lysed is in proportion to the peak negative pressure and the pulse length. Passive acoustic measurements can be used to detect cavitation over time.

In those embodiments, the delivering can further comprise triggering expression of the gas vesicle (GV) type in the delivery cell; and contacting the delivery cell comprising an expressed GV type with the target tissue. In some preferred embodiments, the delivering can further comprise contacting the target tissue with the delivery cell; and then either wait for the biochemical even and/or triggering expression of the gas vesicle (GV) type in the delivery cell after the contacting as described in GV type as described in U.S. Ser. No. 15/663,635 filed on Jul. 28, 2017 and/or Ser. No. 16/736,683 filed on Jan. 7, 2020 incorporated by reference in their entirety.

In those embodiments, the GV type is therefore provided within the delivery cell and contacting the GV type with the target site is performed by contacting the delivery cell comprising the GV type with the target site before or after expression of the GV type in the delivery cell.

For using a delivery cell to deliver the GVs to the target site, the delivery cells are selected or engineered, allowed or induced to reproduce to a desired population, then placed in a delivery medium. In those embodiments providing a delivery cell configured to express the GV type can performed by providing a cell naturally capable of expressing the GV type and/or by engineering a cell to express the GV type as described in U.S. Ser. No. 15/663,635 filed on Jul. 28, 2017 and/or Ser. No. 16/736,683 filed on Jan. 7, 2020 both incorporated herein by reference in their entirety as will be understood by a skilled person.

Accordingly, in embodiments wherein the GV type is comprised within a delivery cell, the delivering can comprise providing a cell genetically engineered to express a GV type the as an output of a genetic circuit in which input is the biochemical event and/or a trigger molecular component as described in GV type as described in U.S. Ser. No. 15/663, 635 filed on Jul. 28, 2017 and/or Ser. No. 16/736,683 filed on Jan. 7, 2020.

In some embodiments, the delivery cell can further comprise a payload substance/compound, and delivering the GV type is performed to release the payload substance/compound in the target site, preferably in proximity of the cavitation target. In some embodiments, the target compound being introduced and held by the delivery cell or a target compound is expressed, either naturally or engineered, by the delivery cell prior to cavitation. In some embodiments, a payload is a therapeutic substance, such as a protein also expressed by the cell that has a therapeutic effect on tissues at a target site where the cells are lysed or a fluorescing protein to act as a marker. In some embodiments, the delivery cell does not contain the target compound, but it is lysed near the target compound to disperse it or increase its uptake by cells. In some embodiments, the dispersal is over a distance greater than 1 mm. In some embodiments, the target compound includes one or more of nanobodies (e.g. CD47nb), cytokines (e.g. CCL121), and anti-cancer protein drugs (e.g. Azurin, Theta-toxin, Hemolysin E (HlyE)).

In an example, macrophages can be loaded with doxorubicin (see e.g. Xu, Zhili, et al. "Real-Time Imaging Tracking of Engineered Macrophages as Ultrasound-Triggered Cell Bombs for Cancer Treatment." Advanced Functional Materials (2020): 1910304). As shown as example in FIG. 17C, a payload release was accomplished by 30 cycle ultrasound pulses at 0.85 MPa (negative pressure).

For example, methods and systems herein described can be performed is to deliver GV type in proximity of a cavitation target deep into cancerous tissue to provide a mechanical stress through cavitation resulting in killing of the cancerous cells, then the method can be performed by providing bacteria that can colonize the deep hypoxic cores of tumors as delivery cells for GVs which can further include an anti-cancer drug as a payload substance compound, alone or in combination with GV types engineered to be functionalized with a binding tag specific for a target molecule of the cancerous cell to provide cavitation on the surface of the As an additional example, a delivery cell configured for expressing the GV type can be configured to have expression of the GV type when a trigger compound or molecule is present in the target site and therefore to cavitate and cause mechanical stress and related modification of the cavitation target only when triggered by the trigger compound or molecule thus providing the GV type in response to a changing environment.

In order to verify that the cavitation occurred as planned, imaging can be performed on the target site after cavitation. The imaging methods can be the same as those used prior to cavitation, with the understanding that the GVs collapsed for cavitation will be in a collapsed state if the cavitation was successful. For example, an image showing a large reduction of non-collapsed GVs can indicate a successful collapse of the GVs.

In some embodiments, the method includes imaging before and after cavitation. In some embodiments, the method includes imaging only before cavitation. In some embodiments, the method includes imaging only after cavitation. In some embodiments, the method does not include imaging. In some embodiments, there is imaging performed throughout.

Figure 5:
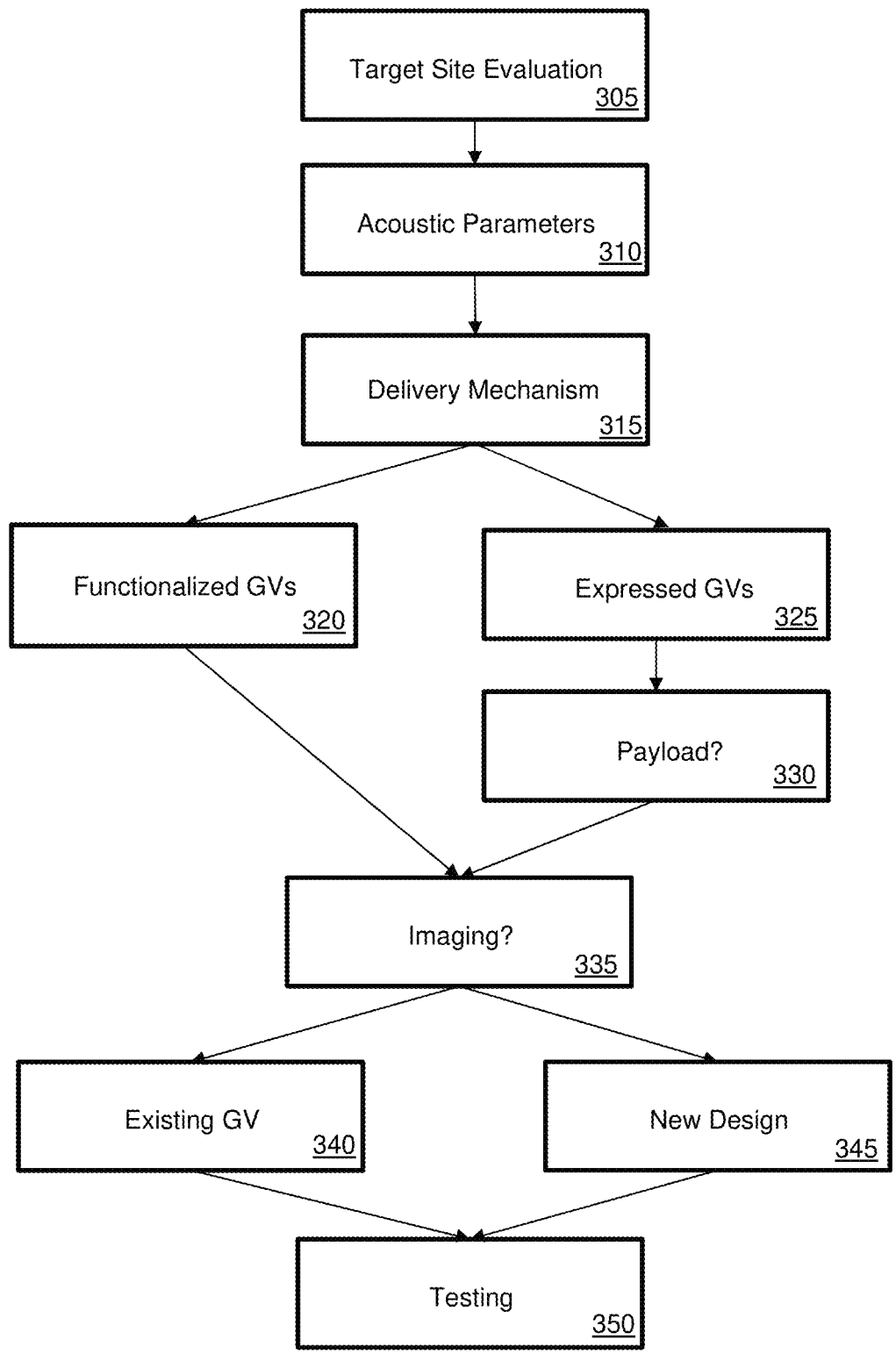
FIG. 5 shows an example method for designing a GV for therapeutic cavitation.

FIG. 5 provides an example method for determining what GV type to use for a given therapeutic application. The order and inclusion of steps is exemplary—other similar methods could also be used.

An initial inquiry can be determining what the objective is (305). In particular, what is the target for the cavitation and what is the desired effect? Examples include lysing the cell walls of a particular tissue or delivering a particular drug to a specific site. This can provide important parameters that will guide further steps, parameters such as cell wall strength, tissue susceptibility to ultrasound, etc.

Another consideration that can be made is how vulnerable the tissue and surrounding tissue is to ultrasound pressure, setting ranges for the acoustic parameters to be used (310). If the goal of the therapeutic cavitation is to only damage specific tissues, then the acoustic pressures used would have to be below an amount that would cause unintended collateral damage to surrounding tissues, at the frequencies being used for cavitation. This means that the GVs to be used will have to have an acoustic collapse threshold, for the intended frequency being used, in that range. An example is in performing cavitation-based therapy in the upper abdomen. Since the alveoli in the lungs are also air-filled sacks, they could be damaged by low-frequency ultrasound, and frequencies higher than 0.5 MHz are typically used. In this contest, a low GV collapse threshold is critical.

The parameters of the ultrasound would have to be sufficient for the desired cavitation. See e.g. FIG. 6. See also Holland, CHRISTY K., and Robert E. Apfel. "An improved theory for the prediction of microcavitation thresholds" IEEE transactions on ultrasonics, ferroelectrics, and frequency control 36.2 (1989): 204-208 and Church, Charles C. "Frequency, pulse length, and the mechanical index" Acoustics Research Letters Online 6.3 (2005): 162-168, for guidance on the parameters.

Another consideration is what delivery system of the GVs to use (315). If a payload (330) is desired, then expressing GVs in a cell to be injected to the site (325) would be chosen. If the desired effect is lysing a cell without delivering a payload, then either functionalized GVs (320) or cells delivered to the site with expressed GVs (325) can be used.

For functionalized GVs (320), a determination of which moieties to use for binding to the target site. As expected, the moiety should bind to the target site and not to nearby non-target tissue. This choice can change the acoustic properties of the GVs, in particular the collapse threshold of the GV. For example, the adding of moieties to the GV shell can weaken it, reducing the collapse threshold. This can be taken into account when designing (345) the GV and during testing (350).

For delivery by a cell expressing the GV (325), several considerations can be taken into account. For example, the selection of injected cell to use. Factors include what damage the cell itself might cause to the tissue or host body outside of the cavitation event, how many GVs would need to be expressed to lyse the injected cell strongly enough for the intended effect (damaging surrounding tissue and/or delivering a payload), what GVs can be successfully expressed in a given cell, in what ways can the cell be delivered to the site, what areas of the body/tissue that particular type of cell is delivered (for example, T-cells and macrophages go to the rims of tumors, while bacteria colonize deep inside them), etc.

For expressed GVs (325), there is the option of delivering a payload (330), either with or instead of damaging target tissue mechanically. If this is desired, then considerations such as payload type (what substance is being delivered), payload amount, effect if any of the payload on the GV collapse and subsequent cavitation (as the payload and GVs will, at some point, be in the same cell together), etc. can be taken into account.

Another consideration is if imaging is desired (for example, for determining if the GVs have reached the target site) and, if so, what type of imaging to use (335). The imaging needs to be a type that is non-destructive to the GVs, so the GVs remain intact for the ultrasound pulse. To maximize the number of bubbles being released (the number of GVs collapsing), the GV can be selected/designed to have a relatively low collapse threshold, which is in contrast to the GV selection/design for non-destructive imaging, which prefers a high collapse threshold. In embodiments herein, both imaging amplitudes and cavitation amplitudes are considered when selecting/designing the GV type with respect to collapse threshold.

From all the considerations made (305-335), a GV can be selected, either from a list of existing GVs (340) or as a newly designed GV (345). The selection and design (340, 345) will depend upon the acoustic properties determined by the considerations (305-335), for example what range can the acoustic collapse pressure of the GVs fall into. The range can involve ideas such as ensuring the GVs do not collapse prior to the ultrasound pulse (threshold too low) and ensuring that the GVs collapse from a ultrasound pulse that does not have unintended effects on the tissue's host (threshold too high).

Given all of the factors that have to be taken into account (305-345), testing the GVs (350) can be useful for ensuring that the GVs will perform as intended. A test (350) can be performed on the final product GV (340, 245), but also intermediate tests can also be performed along the way (305-335) for proof-of-concept evaluations on if a particular design is in the right direction. For example, for expressed GV to be delivered to a site with a payload, a test can be performed on GVs expressed in vitro with no payload included in the cells, to determine an estimate of the acoustic collapse pressure threshold of the GV, with further testing being made with the payload included to see if it has any effect on that estimate.

In some embodiments herein described, multiple GV types can be delivered simultaneously for controlled multiple cavitation events. In particular, methods and systems for creating multiple cavitation events comprise delivering a first GV type and a second GV type to a target site, the first GV type having a first collapse threshold and the second GV type having a second collapse threshold. After both GV types are present at the target site, a first ultrasound pulse is applied at a collapse amplitude above the first collapse threshold and under the second collapse threshold, the first ultrasound pulse having a pulse duration sufficient to cavitate bubbles generated by the first GV type collapsing. After the first ultrasound pulse is applied, a second ultrasound pulse is applied having a collapse amplitude greater than the second collapse threshold and a cavitation amplitude sufficient for cavitation. For a first example, two GV types are functionalized to attach to two different target cells, which are then lysed sequentially by the sequential cavitation events. For another example, two sets of delivery cells can be delivered to the target site, one delivery cell expressing the first GV type and containing a first compound and the other delivery cell expressing the second GV type and containing a second compound, the first compound and second compound then being released sequentially by the sequential cavitation events. Uses for using multiple GV types include: propelling stronger GVs by cavitating weaker ones; having the ability to choose between several cavitation doses, depending on the peak positive pressure; and combining cavitation with destructive imaging. Additionally, multiple delivery cells can be used, where one delivery cell expresses GVs for cavitation and the other delivery cell expresses the payload for release upon cavitation of the GVs.

FIG. 6 provides an example method for selecting ultrasound parameters suitable for producing GV cavitation and achieving desired effects on surrounding cells or materials. First, GVs that have been functionalized to bind to the target receptor sites, or cells (bacteria, mammalian cells, archaea, etc.) that express GVs are produced (605). These can be either previously engineered GVs, cells that have been previously properly engineered, or they can be newly engineered GVs or cells. The cells can also be engineered to express a specific protein that is desired to be delivered to the target site (such as a drug). Then, the FUS and imaging/PCD configuration and frequencies are selected according to the desired application (610). Examples of important parameters taken into consideration when determining the configuration of the system include the depth of the target, its size, and close by structures. Then, in vitro PCD tests are performed (615) to facilitate the selection of ultrasound parameters including the pulse peak positive pressure the peak negative pressure, pulse length, and duty-cycle. Additional parameters that can be tuned according to PCD signals include the GV concentration and type. Next, in vitro phantom experiments are performed to test the interaction of the GVs or delivery cells with their surroundings (620). These tests can include measuring the payload release from cells, testing for payload propulsion into tissue mimicking phantoms and measuring the lysis of delivery cells or neighboring target cells. All previously selected parameters can be fine-tuned according to these results. Pre-clinical experiments can be performed to test the effect of tissue attenuation and structure on the cavitation activity (625). Finally, the GVs or GV expression cells can be tested for the desired in vivo scenario (630).

Figure 7:
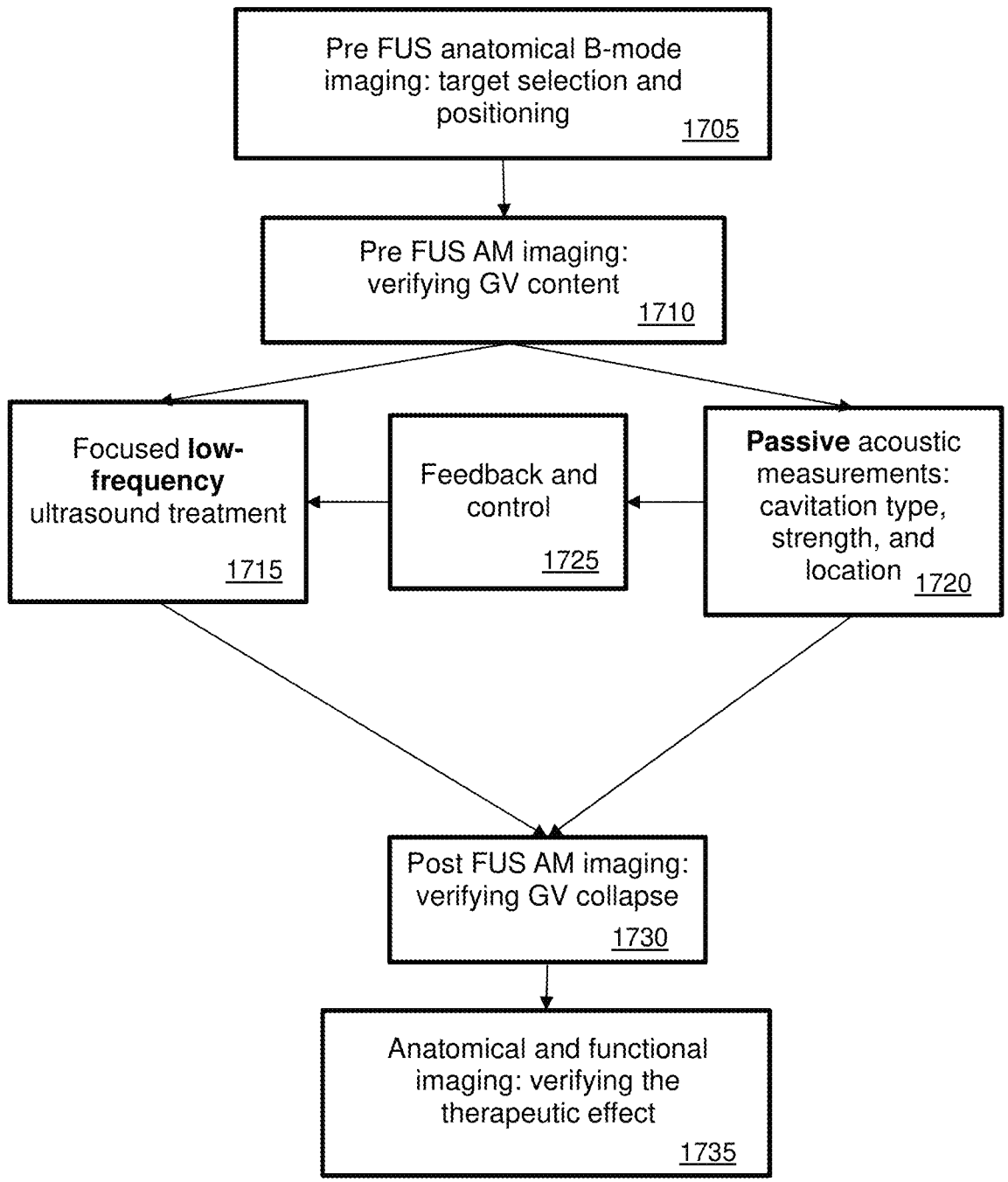
FIG. 7 shows an example ultrasound-guided cavitation session including planning, therapy, control, and treatment monitoring.

FIG. 7 provides an example sequence of ultrasound imaging-guided FUS treatment. Ultrasound guidance is described although other imaging modalities can be used. All imaging and passive acoustic measurements are performed at typical imaging frequencies of several megahertz. After the alignment of the imaging and FUS transducer, anatomical B-mode imaging can be used to locate the position if the FUS beam in space and position it at the desired target location (1705). AM imaging is sensitive to the unique contrast of GVs and can be used for verifying the GV content at the target (1710). Then, a sequence of low frequency FUS pulses are transmitted (1715). Passive acoustic measurements can be performed in parallel, providing functional information of the type of cavitation activity, its strength, and location (1720). This information can be used for adding automatic feedback and control to the FUS sequence. This can include changing the pressure level to switch between inertial and stable cavitation or shutdown of the FUS treatment if safety concerns arise (1725). After the completion of the treatment, another AM scan can be performed to verify GV collapse, as another proxy for in-vivo pressure measurement (1730). Finally, post treatment anatomical and functional imaging can be performed to verify the therapeutic effect (1735). Additional monitoring can be performed at later time, if needed.

FIG. 8 provides an example of information given by PCD processing. PCD measurements taken without activating the FUS system give information about the noise floor of the system. This information is later used as a baseline for assessing cavitation activity. Stable cavitation is characterized by harmonic signals with signal spiking around the multiples of the FUS frequency. Inertial cavitation is characterized by wideband signal. See e.g. FIG. 10, panel c. The power of the measured cavitation signal (805) is indicative to the cavitation power and can quantified and expressed in real units, given the proper calibration. It is possible to quantitatively assess the degree of stable (815) vs. inertial (810) cavitation by comparing the power in the harmonic bands to the power outside them. Finally, if passive cavitation measurements are performed using an array of elements (e.g. imaging probe), it is possible to beamform the received signals and produce a spatiotemporal map of cavitation activity in space. Relevant information on the on-target and off-target cavitation activity can be deduced from such map and enable close loop control of cavitation activity.

EXAMPLES

The GVs and related compositions, systems and methods herein disclosed are further illustrated in the following examples, which are provided by way of illustration and are not intended to be limiting.

In particular, the examples herein illustrate exemplary methods and protocols for preparing exemplary wild type and genetically engineered gas vesicles protein structure, and related characterizing testing and using these structure for inertial cavitation under ultrasound in vivo and in vitro. A person skilled in the art will appreciate the applicability and the necessary modifications to adapt the features described in detail in the present section, to additional gas vesicle protein structure and related methods and systems according to embodiments of the present disclosure.

The following materials and methods were used in the experiments illustrated in the Examples.

Gas Vesicle Purification, Modification, and Quantification:

*Anabaena flos-aquae* GVs were produced and purified according to a published protocol[29]. As a quality assurance step, OD measurement were performed for each sample at 0-12 bar using an echoVis Vis-NIR light source coupled with an STS-VIS spectrometer (ocean optics), and a 176.700-QS sample chamber (Hellma Analytics). The outer structural protein GvpC was removed from GVs used in the in vivo experiment to facilitate their ultrasound detection. GvpC was removed and replaced by an engineered, recombinantly expressed, protein, GvpC-RGD, for experiments in which GVs were attached to U87 cells[18]. Prior to experiments, GV concentrations were measured using a spectrophotometer (Thermo Scientific NanoDrop™ ND-1000) at 500 nm.

In Vitro Passive Cavitation Detection:

The in vitro setup was aligned in a three-step process. First, an L22-14v 128-element Verasonics™ imaging probe was positioned such that its focus, set to a depth of 8 mm, was positioned at the center of 1 cm×1 cm 3D-printed chamber. Then, an optic fiber hydrophone (Precision Acoustics™) was positioned at the center of the chamber using B-mode imaging. Finally, a 670 kHz (Precision Acoustics) or 3 MHz FUS transducer (Ultrasonic S-Lab) was mounted on a computer-controlled 3D translatable stage (Velmex™) orthogonally to the Verasonics™ probe. A MATLAB program automatically scanned and aligned the transducer's focus at the center of the chamber, according to the feedback from the hydrophone.

A solution of purified GVs ($OD_{500}$=0.5, or 0.3 nM, unless stated differently) or GV-expressing bacteria was gently pipetted into the 3D printed chamber to minimize introduction of bubbles. Purified GVs solutions had been prepared several days in advance to allow natural degassing. The Verasonics™ scanner was programmed to function in zero-amplitude transmit so it could be used as a passive cavitation detector. A Verasonics™ MATLAB script was written to synchronize the acquisition of GV soundwaves by triggering the FUS burst and accounting for propagation time of the insonating wave to the focus. The GV solution was stirred during acquisition using a micro stir bar and magnetic stirrer (Thermo Scientific™). Raw data was saved into .mat files for further processing.

To compensate for the slow rise time of the Precision Acoustics transducer, a custom signal generator waveform with 33 cycles was created such that the first 4 cycles had 1.5× the peak amplitude as the last 29 cycles; this waveform induced our FUS to reach the desired peak negative pressure (PNP) output at the 4th cycle. In experiments where the effect of the number of cycles on cavitation was investigated, a waveform with 3 cycles at 2× the amplitude of the remaining cycles was used so that the desired PNP was reached at the 3rd negative peak.

In Vitro Cancer Cell Sonoporation Experiments:

Glass bottom 35 mm petri dishes (Matsunami) were modified to enable U87 cell culture and subsequent ultrasound application. The glass was removed using a glass cutter and a Mylar film (Chemplex, 2.5 μM thickness) was fixed over the hole via a polydimethylsiloxane elastomer (Sylgard 184 silicone, Dow Corning). After curing for 2 hours at 40° C., these dishes were sterilized using UV light. U87 cells were plated on the Mylar film dish and incubated for 2 days at 37° C. in 2 mL of DMEM media. In order to facilitate the attachment of RGD-GVs to the cells membrane, the GVs were resuspended in fresh DMEM medium (final concentration of 0.5 $OD_{500}$) and added to the center of the dishes. The center of each dish was sealed using an 18 mm round cover glass and kept inverted for 2 hours at room temperature. Then, cells were washed and recovered with fresh DMEM. Finally, 10 μg/ml propidium iodide (PI, Invitrogen) was added to the medium just before the ultrasound experiment.

The cells were insonated using a 670 kHz transducer (Precision Acoustics™) that was positioned in the water tank at an angle of 20° relative to the water surface, to minimize standing waves. The ultrasound transducer was aligned to the microscope using a hydrophone. First, the tip of the fiber-optic hydrophone (Precision Acoustics™) was brought into optical focus and positioned in the center of the image. Then, the transducer was shifted until the hydrophone reading was maximized. The cells were insonated for 10 seconds with PNP=1.5 MPa ultrasound pulses at a 2 ms pulse repetition rate. Fluorescence recording began 1 minute before insonation, continued throughout ultrasound exposure, and ended 6 minutes after insonation. Change in the cells' fluorescence signals were collected and recorded using a 10× immersion objective (Olympus, NA 0.3), and a sCMOS camera (Zyla 5.5, Andor) at a 10 Hz frame rate. After this acquisition, saponin (Sigma™, 100 μg/ml) was used to perforate all cell membrane, and the resulting image was used as a mask for cell body detection. The fluorescence images were processed using NeuroCa™[37] to extract the fluorescent signals from individual cells. Cells were defined as PI-positive if signal intensity increased by more than 2% following ultrasound application.

High Frame Rate Camera Imaging Experiments:

A high-speed microscopy setup capable of directly capturing GV collapse and bubble cavitation events was assembled. The setup used a 2W 532 nm laser (CNI™, MLL-F-532-2W) controlled by an optical beam shutter (Thorlabs™ SH05, KSC101). Right angle prism mirrors direct the laser light through a water bath and into a sample dish containing the imaged samples.

For imaging purified GVs, the GVs were coated with biotin by incubating them for 1 hour with sulfo-NHS-biotin (Thermo Fisher Scientific) with a 10,000-fold molar excess of sulfo-NHS-biotin to GVs. Then, the non-attached biotin was removed from the cell solution with two rounds of dialysis in PBS. The Mylar dishes were prepared by first treating them with UV light, and then incubating each dish with 180 μL of 0.1 mg/mL Poly-D-lysine hydrobromide. Then, the PDL coated Mylar dish was incubated with sulfo-NHS-biotin (Thermo Fisher Scientific, 180 μL, 2 mM) for 1 hour. After washing the free biotin with PBS (3 rounds) The dish was incubated with streptavidin (G-Biosciences, 180 μL, 7.35 μM) for 1 hour. The dishes were then washed again to remove the free streptavidin. Finally, the GVs were attached to the dishes. After adding 180 μL of GVs at an $OD_{500}$=2 to each dish, the center of each dish was sealed using an 18 mm round cover glass and kept inverted for 2 hours at room temperature. Then, excess GVs were washed with PBS.

Dishes containing GVs or cells were positioned above a water tank and aligned with the transducer focus as described above. A 10× water immersion Plan Fluor objective (Olympus™ NA 0.3) was lowered into the solution in the dish. A series of prism mirrors and converging lenses with focal lengths of 200 mm and 50 mm delivered the image into a Shimadzu™ HPV-X2 camera, which acquired 256 images (see FIG. 14) over 51.2 μs, at a sampling rate of 5 million frames per second. To account for acoustic propagation through water, the camera was externally triggered to begin acquisition 40 μs after the start of the ultrasound pulse. A single pulse with PNP=1.4 MPa was used to insonate the sample in these experiments.

Bacterial Expression Experiments:

GV-expressing *Salmonella typhimurium* were produced by transforming cells with a plasmids encoding an engineered GV operon[22,29] followed by a NanoLuc® luciferase (Lux). Cells transformed with a NanoLuc plasmid were used as controls for these in vitro experiments. Constructs were assembled using Gibson cloning. The genetic constructs were placed in pTD103 plasmids (gift from J. Hasty), with expression driven by a luxI promoter upon induction with 3 nM N-(β-ketocaproyl)-1-homoserine lactone (AHL). The cells were cultured for 24 hours at 30° C. after induction, then centrifugated for 4 hours at 150×g and 4° C. for enrichment of the buoyant cells. Samples of cells used in PCD experiments were stored for two days at 4° C. before these experiments and were always gently pipetted so as to minimize media gassing and bubble formation. Samples of cells used for the NanoLuc release experiment were washed four times by 2 hours of centrifugation at 150×g and 4° C. to remove NanoLuc molecules that were already present in the media prior to the experiment.

PCD recordings from GV-expressing cells were performed using the same setup and protocol used in PCD recordings from purified GVs, except that solutions were at a concentration of $OD_{600}$=1. The same experimental setup was also used in the bacteria lysis and the payload release experiments; however, in these experiments, samples were insonated for 30 seconds at 300 kHz, PNP=1 MPa, and a pulse repetition interval of 2 ms to ensure that the entire sample was insonated. For colony counts, the cells were plated on agar plates with Kanamycin antibiotic. Plates were imaged using a ChemiDoc™ Gel Imaging System and the epi white light protocol. Then, the colonies were counted to determine total colony forming units. In the payload release experiments, the solution was aspirated from the chamber after the exposure to ultrasound, pipetted into 100 kDa Spin-X(R) UF concentrators (Corning) and centrifuged at 300 g for 30 minutes to separate the supernatant fluid from the pellet and the buoyant cells. Then, the NanoLuc signal was measured using a Nano-Glo Luciferase assay kit (Promega) and a plate reader system (molecular devices). Full chemical lysis of cells using SoluLyse™ Protein Extraction Reagent (Genlantis) was used as positive control.

Mammalian Expression and Experiments:

mARG-HEK cells were grown in 10 cm dishes. Once they reached 60-70% confluency, they were induced with 1 μg/mL doxycycline and 5 mM sodium butyrate for 6 days. The cells were then trypsinized and resuspended in fresh DMEM before moving to the cavitation chamber. The samples were positioned in agar wells at the center of acoustically transparent cuvette as discussed above. In these experiments, samples were insonated for 30 seconds at 334 kHz, PNP=1 MPa, and a pulse repetition interval of 2 ms. Cells were stained with Zombie NIR viability dye (BioLegend) following the manufacturer's protocol, and cell lysis was measured using cell cytometry. Relative cell death was measured using the Beckman Coutler Cytoflex Flow Cytometer (Beckman Coutler Inc.) based on Zombie NIR fluorescence.

In Vitro Ultrasound Imaging of GV Expressing Cells:

To create phantoms for in vitro ultrasound imaging, wells were casted with molten 1% w/v agarose in PBS using a custom 3D-printed template. Next, trypsinzed cells were mixed at a 1:1 ratio with 42° C. low-melt agarose and loaded into the wells before solidification. The volume of each well was 25 µl and contained $2 \times 10^5$ cells. The phantoms were submerged in PBS, and ultrasound images were acquired using a Verasonics Vantage system and L22-14v transducer (Verasonics™). See FIG. 3 for an example setup. Each amplitude modulation (AM) frame was formed from 89 focused beam ray lines, each with a 40-element aperture and 8 mm focus [Ref: Maresca, D. et al. Nonlinear ultrasound imaging of nanoscale acoustic biomolecules Nonlinear ultrasound imaging of nanoscale acoustic biomolecules. 073704, (2017)]. A 3-half-cycle transmit waveform at 17.9 MHz was applied to each active array element. Each image captured a circular cross-section of a well with a 4-mm diameter and center positioned at a depth of 8 mm. In AM mode, the signal was acquired at 0.27 MPa (2V) for 10 frames and the acoustic pressure was increased to 1.57 MPa (10V) to collect 46 additional frames. Ultrasound images were constructed by subtracting the collapsing frame by frame 4 post-collapse.

In Vivo Passive Cavitation Detection:

All in vivo experiments were performed on BALB/c female mice, under a protocol approved by the Institutional Animal Care and Use Committee of the California Institute of Technology. No randomization or blinding were necessary in this study. Mice were anaesthetized using 1-2.5% isoflurane during all the injection and imaging procedures. The MC26 colorectal cancer cell line were maintained per standard cell culture techniques. Five female BALB/c mice, aged 8 weeks, were given subcutaneous inoculations of $1 \times 10^6$ MC26 cells into both right and left hind flanks. Tumors were monitored and permitted to grow to a diameter of 6-10 mm over 10-20 days.

A 3D-printed theranosic holder co-aligned a 0.67 MHz FUS transducer (Precision Acoustics) and an L22-14v 128-element imaging probe (Verasonics™) by fixing the FUS focus at 12 mm along the imaging plane (FIG. 18A, panel a). The holder places the FUS cone facing downwards and the imaging probe at approximately 30° from the vertical. A 3D-printed needle guide was mounted to the side of the cone such that the tip of a 1-inch 30 g injection needle also intersected the focus. The holder was mounted on a manually-controlled 3D positioner.

Mice were anaesthetized, maintained at 37° C. on a heating pad, depilated over the tumor region, and positioned with tumor facing directly upwards. Prior to the experiment, the ultrasound gel was centrifuged at 2000×g for 10 minutes to remove bubbles, heated to 37° C., and then carefully applied to couple the cone and probe to the tumor. B-mode anatomical imaging was used to confirm absence of bubbles in gel application and to position the center of the tumor at an axial depth of 12 mm. B-mode and amplitude modulation (AM)[21] images of the tumor were saved pre- and post-insonation. Insonation was done with a single 30-cycle, PNP=1 MPa burst. The same PCD script was used as for in vitro PCD acquisitions.

As part of the experiment, 20 µl $OD_{500}$=4.5 GVs (with GvpC removed) or saline were infused directly into the tumor at a flow rate of 10 µl min$^{-1}$ via a Genie Touch syringe pump through PE10 catheter tubing and a 30 g needle (BD). Injection at the focal zone was confirmed via B-mode imaging by locating the needle tip, and AM and B-mode images were recorded pre- and post-insonation. PCD measurements were performed during each insonation.

Cavitation effect on liver tissue in vivo:

Five female BALB/c mice, aged 8 weeks were included in each group. The 3D-printed in vivo theranosic holder was aligned and used as discussed above. Mice were anaesthetized, maintained at 37° C. on a heating pad, depilated over the abdomen and lower torso region, and place in a supine position. The therapeutic and imaging transducer we coupled to the mouse using centrifuged ultrasound gel prepared as described above. B-mode anatomical imaging was used position the FUS beam at the region of interest in the liver tissue.

200 µL of $OD_{500}$=37 Ana GVs (with GvpC removed) or saline were infused systemically using a tail vain catheter at a flow rate of 100 µL min$^{-1}$ via a Genie Touch syringe pump through PE10 catheter tubing and a 30-gauge needle (BD). to confirm liver uptake and post-treatment GV collapse, B-mode and amplitude modulation (AM) [Ref: Maresca, D. et al. Nonlinear ultrasound imaging of nanoscale acoustic biomolecules Nonlinear ultrasound imaging of nanoscale acoustic biomolecules. 073704, (2017)] scans of the liver were saved pre- and post-injection, and post-insonation. Here insonation comprised 30-cycle ultrasound pulse train at 670 kHz, PNP=1.5 MPa and 2 ms pulse repetition interval for 30 s.

Following ultrasound exposure, we perfused the mice and collected their livers. Tissue was fixed for 48 hours in 10% formalin and then moved to 70% EtOH for storage. Next, the fixed tissue was embedded in paraffin, sectioned and stained with H&E. The ImageJ [Ref: Schneider, C. a, Rasband, W. S. & Eliceiri, K. W. NIH Image to ImageJ: 25 years of image analysis. *Nat. Methods* 9, 671-675 (2012)] color unmixing function was applied to the H&E images, resulting in separate images of the tissue, the blood, and the background [Ref: Bar-Zion, A., Yin, M., Adam, D. & Foster, F. S. Functional flow patterns and static blood pooling in tumors revealed by combined contrast-enhanced ultrasound and photoacoustic imaging. *Cancer Res.* 76, 4320-4331 (2016)] according to their distinct characteristic colors. The color un-mixing parameters are included in Table 2. Bleeding was quantified by summing over the blood-positive pixels (grayscale >220) and by counting the hemorrhagic foci. Hemorrhagic foci were defined according to the H&E images as areas showing bleeding, in red, surrounded by necrotic tissue in pink.

Table 2 lists the pixel values used for color un-mixing of H&E stains. In particular, the following RGB values were used for performing a color un-mixing (deconvolution) operation, separating the H&E stains to images showing red blood cells in red (gray dotted areas), and liver tissue in purple (black region).

TABLE 2

| Component | R | G | B |
|---|---|---|---|
| Blood | 223 | 78 | 97 |
| Tissue | 198 | 82 | 140 |
| Background | 243 | 243 | 242 |

Passive Cavitation Detection Data Processing:

The acoustic emissions acquired by the PCD were sampled by the Verasonics™ scanner at 62.5 MHz and processed using a MATLAB (2017b, Mathworks) script. Single channel, 8192-point FFT frequency spectrum estimations of the RF recordings from the 128 transducer elements were averaged to produce each PCD frequency spectrum estimation.

In order to calculate the average amount of stable cavitation, an acquisition with clear harmonic response was used to manually select and save the peak harmonic frequencies (see Table 3). Then, a trend curve was fitted to each spectral estimation using the MATLAB Curve Fitting tool. The smoothing parameter was chosen such that the resulting curves included only the broadband signal and not any harmonic peaks. This smoothened curve was subtracted from the original frequency spectrum, and the resulting flattened spectrum with harmonic peaks was integrated over the peaks, each with a bandwidth of 191 kHz for the 670 kHz measurements, or 610 kHz for 3 MHz measurements. These bandwidths were manually selected to include the full harmonic peak. Integrals were performed using trapezoidal sums, then the integral was divided by the number of peaks multiplied by the peak bandwidth.

TABLE 3

| Detected Harmonic # | Frequency ($f_0$ = 0.67 MHz) | Frequency ($f_0$ = 3 MHz) |
|---|---|---|
| 1 | 8.04 | 8.96 |
| 2 | 8.71 | 11.93 |
| 3 | 9.38 | 14.95 |
| 4 | 10.05 | 17.93 |
| 5 | 10.72 | 20.86 |
| 6 | 11.40 | 23.83 |
| 7 | 12.06 | |
| 8 | 12.73 | |
| 9 | 13.40 | |
| 10 | 14.08 | |
| 11 | 14.74 | |
| 12 | 15.42 | |
| 13 | 16.08 | |
| 14 | 16.75 | |
| 15 | 17.43 | |
| 16 | 18.09 | |
| 17 | 18.76 | |
| 18 | 19.43 | |
| 19 | 20.11 | |
| 20 | 20.77 | |
| 21 | 21.44 | |
| 22 | 22.11 | |
| 23 | 22.78 | |
| 24 | 23.45 | |
| 25 | 24.12 | |
| 26 | 24.79 | |
| 27 | 25.46 | |
| 28 | 26.13 | |
| 29 | 26.81 | |

Frequencies of peak harmonic signals detected by PCD. Harmonics of the central frequency $f_0$=0.67 MHz are presented in the middle, and harmonics of the central frequency $f_0$=3 MHz are presented on the right.

In order to calculate the average amount of broadband emission, baseline noise at PNP=0 MPa was subtracted from each reading. Then, the flattened spectrum with harmonic peaks was subtracted. The spectrum was integrated between 7.4 MHz and 28.6 MHz, which marked the beginning and end of baseline noise, then divided by 21.2 MHz.

Statistical Analysis:

For statistical significance testing, two-sided heteroscedastic t-tests were used with a significance level of type I error set at 0.05 for rejecting the null hypothesis, unless mentioned otherwise. A Wilcoxon rank sum test was used in high-speed camera experiment that include a control group which was proven to be non-Gaussian using a Lilliefors test (P<0.001). A two-way ANOVA test was used in the payload release experiment. Sample sizes for all experiments, including animal experiments, were chosen on the basis of preliminary experiments to be adequate for statistical analysis.

Data and Code Availability:

MATLAB codes are available from the corresponding author upon reasonable request. Plasmids sequences are included in Table 4. All other materials and data are available from the corresponding author upon reasonable request.

Table 4 shows the genetic constructs used in this study. All plasmids were constructed using the pTD103 backbone with a NanoLuc protein payload, with or without a GV-producing gene cassette. Sources of genetic elements: pTD103 plasmids: J. Hasty, UCSD (see "A sensing array of radically coupled genetic 'biopixels'". Prindle A, Samayoa P, Razinkov I, Danino T, Tsimring L S, Hasty J. Nature. 2011 Dec. 18; 481(7379):39-44. doi: 10.1038/nature10722. 10.1038/nature10722 PubMed 22178928); ARG1: Addgene #106473 (see Bourdeau, Raymond W., et al. "Acoustic reporter genes for noninvasive imaging of microorganisms in mammalian hosts." Nature 553.7686 (2018): 86-90.); NanoLuc: Addgene #87696 (see "Optogenetic control with a photocleavable protein", PhoCl. Zhang W, Lohman A W, Zhuravlova Y, Lu X, Wiens M D, Hoi H, Yaganoglu S, Mohr M A, Kitova E N, Klassen J S, Pantazis P, Thompson R J, Campbell R E. Nat Methods. 2017 Mar. 13. doi: 10.1038/nmeth.4222. 10.1038/nmeth.4222 PubMed 28288123).

TABLE 4

| Plasmid | GV cassette | Payload |
|---|---|---|
| pABZ_01 | ARG1 (A2C) | NanoLuc |
| pABZ_02 | — | NanoLuc |

Example 1: Use of Gas Vesicles as Nuclei for Inertial Cavitation

The use of GVs to nucleate bubbles for inertial cavitation has been verified with experiments providing proof of principle that GVs collapse under applied acoustic pressure, release the air contained inside them to the surrounding media that can be used for inertial cavitation according to the series of steps schematically illustrated in FIG. 9C.

In particular, the GV's amphiphilic protein shell encloses a stable, gas-filled structure (FIG. 9A). which can be imaged by transmission electron microscopy (TEM) (FIG. 9B). An ultrasound (US) pulse with a positive pressure higher than the critical collapse pressure $P_{col}$ collapses the GV, resulting in a nanoscale bubble. The released nanobubble undergoes cavitation if the peak negative pressure of the US pulse reaches below the critical cavitation pressure $P_{cav}$. Over several cycles, the nanobubble is converted into a micronscale bubble, which can eventually undergo violent inertial cavitation. (see FIG. 9C, Scale bar represents 100 nm).

The ability of such collapse to take place at specific pressure thresholds, defined by GVs' DNA sequence and protein composition, has been used for background-subtracted molecular imaging[13, 14, 18, 22]. Under most conditions, gas molecules released from collapsed GVs are expected to form nanoscale bubbles, which should dissolve within milliseconds due to Laplace pressure. However, it was expected that at ultrasound frequencies in the sub-MHz range, these free bubbles can also serve as seeds for cavitation, a process in which bubbles expand and contract during the negative and positive phases of sound waves, respectively, and can grow in size through rectified diffusion of gas and coalescence[23]. Such processes are favored at lower ultrasound frequencies and higher peak negative pressures. In addition, bubbles can be stabilized by the presence of hydrophobic surfaces[23], such as the exposed interior of collapsed GV shells. It was envisioned that at low frequency, positive pressure above GVs' critical collapse threshold would release gas nanobubbles through GV collapse, then negative pressure would cause bubble growth. At low ultrasound cavitation amplitudes, the resulting bubbles would undergo stable cavitation—a sustained periodic oscillation of gas bubble size. At high cavitation amplitudes, the bubbles would undergo rapid growth and violent collapse in a process known as inertial cavitation, unleashing powerful mechanical effects[24] (FIG. 9C).

To test the hypothesis that GV can seed bubble cavitation, acoustic emissions of GVs purified from *Anabaena flos-aquae* (Ana) were measured during exposure to sub-MHz ultrasound. Focused ultrasound (FUS) was applied to GV suspensions in a custom-build chamber with acoustically transparent walls, while emitted signals were recorded with an orthogonally positioned imaging transducer acting as a passive cavitation detector (PCD" (FIG. 10, panel a). The method for in vitro passive cavitation detection is described in the general procedure above. Unless stated otherwise, the samples were insonated throughout the study at 0.67 MHz, within the range of frequencies commonly used in therapeutic ultrasound. The PCD transducer was a 128-element linear array with a center frequency of 18 MHz. Bubbles undergoing stable cavitation emit sound waves at harmonic multiples of the transmitted frequency, while those undergoing inertial cavitation produce emissions with broad spectral content.

Using this setup, both stable and inertial cavitation were observed as shown in FIG. 10.

Harmonic signals, indicative of stable cavitation, were clearly elicited at 0.2 MPa peak negative pressure (FIG. 10, panels b, c), while broadband spectral emissions, characteristic of inertial cavitation, were observed at higher pressure levels (FIG. 10, panels b, d). The detected harmonic signal suggests that the released nanobubbles could be coalescing into micron size bubbles. The attenuation of ultrasound at high GV concentrations explains the lower cavitation signal beyond a certain concentration. These values were significantly higher than those recorded from buffer or solutions of bovine serum albumin (BSA), which served as a protein control. Broadband emissions increased moderately with the pulse length (FIG. 10, panel e, n=12), and pulses with only 3 peak negative cycles were sufficient to produce signals 25±0.7 dB above the noise floor, consistent with other cavitation studies[25,26]. As expected, the measured broadband signal increased with GV concentration until reaching a peak at 0.3 nM (FIG. 10, panel f), above which acoustic shadowing interfered with measurement (see FIG. 11). These results suggest that GVs are able to serve as nuclei for inertial cavitation at 0.67 MHz.

Since GV are also used for ultrasound imaging, typically at frequencies of several MHz, cavitation responses at 3 MHz was also measured. At this frequency inertial cavitation required much higher pressures (FIG. 12, panels a-b), consistent with the lower efficiency of free bubble cavitation at higher frequencies, as well as the increased pressure required to collapse GVs at frequencies above the gas permeation rate of their protein shell[27]. This result affirms the ability of GVs to be imaged safely using typical diagnostic parameters[20,21] while serving as seeds for inertial cavitation at lower frequencies.

Example 2: Ultrafast Optical Imaging of GV-Seeded Bubble Formation and Cavitation To more directly visualize the process by which GVs nucleate the formation of cavitating bubbles, GVs prepared as indicated in Example 1 were purified GVs were coated with biotin by as described above. Then, the GVs were attached to acoustically transparent biotin-streptavidin coated Mylar dishes. Each dish was filled with 180 μL of GVs at an OD500=2 and excess GVs were removed after a 2-hour incubation time. Full details on sample preparation and details on how the imaging was performed can be found in High frame rate camera imaging experiments section of the general protocol above.

In particular, this process was imaged optically using an ultra-high frame rate camera, acquiring images at 5 million frames per second (FIG. 13A, panel a). The GVs were attached to acoustically transparent Mylar-bottomed dishes using biotin and streptavidin. Before insonation, a dark pattern indicative of intact GVs (FIG. 13A, panel b) was observed, whose gas interiors scatter visible light[16,28]. After ultrasound was applied and reached sufficient collapse amplitude, this dark pattern suddenly disappeared, revealing GV collapse occurring on a time scale of 0.2 μs (0.4-0.6 μs, FIG. 13A, panel b and FIG. 14). 2.4 μs later, dark bubbles were observed forming and cavitating inside the field of view (FIG. 13A, panel b).

Meanwhile, control dishes with biotin coating alone failed to show significant cavitation (FIG. 13A, panel c). Videos were further analyzed to track the temporal relationship between GV collapse and bubble cavitation. After forming, bubbles grew and shrank at the frequency of the ultrasound waves (FIG. 13A, panel d). By comparing the phase of the wave at which GVs disappear with the phase of maximal bubble growth rate, it can be confirmed that GVs collapse at the positive pressure peak, while maximal growth of the resulting bubbles occurs at the peak negative pressure, $\pi$ apart in phase (FIG. 13B, panel e). Furthermore, as expected, the bubble size peaked at $3/2\ \pi$, at the conclusion of rarefaction (FIG. 13B, panel f). Similar results were seen across multiple bubbles (FIG. 13B, panel g). This data provides direct support for the mechanistic model depicted in FIG. 9C.

Example 3: Receptor-Targeted GVs Serve as Acoustically Detonated Cellular Disruptors This example is carried out to test an application of biomolecular cavitation using GVs: acoustically detonated killing of tumor cells with receptor-target GVs.

To test this application, GVs were genetically engineered to display an RGD peptide on the C-terminus of their external shell protein GvpC, thereby targeting them to $\alpha v \beta_3$ integrin receptors commonly overexpressed in tumors[29]. These nanostructures were incubated with U87 glioblastoma cells cultured on acoustically transparent Mylar film (FIG. 15A, panels a and b). For visualization, GVs were also labeled with Alexa Fluor 488. To monitor cellular disruption, the media was supplemented with propidium iodide (PI), a membrane-impermeable fluorophore that becomes fluorescent upon entering disrupted cells and intercalating with nucleic acids. Details on in vitro cancer cell sonoporation experiments can be found in the general procedure section above.

Prior to ultrasound exposure, there was negligible PI signal. However, after insonation for 10 seconds, gradual PI uptake was observed in many cells throughout the field of view (FIG. 15B, panels c-d), as quantified relative to PI uptake after saponin treatment at the end of the experiment (FIG. 15C, panel e). Ultrasound alone in the absence of GVs did not result in significant PI uptake.

To directly visualize the effect of ultrasound on GVs attached to U87 cells, the cells were imaged at 5 million frames per second. After the collapse of cell-attached GVs (FIG. 16, a-b) bubble formation and cavitation were observed (FIG. 15C, panel f; FIG. 16, panel c). The number of cavitation events in cells targeted with GVs was significantly larger than the number of random cavitation events in untreated cells (FIG. 15C, panel g). The spatial heterogeneity of cavitation in the high-speed camera experiment (FIG. 15C, panel f; FIG. 16, panel c) was consistent with the clustering of PI-positive cells next to each other (FIG. 15B, panel c). Together with fluorescence imaging, these results suggest that GVs can be used as targeted, acoustically triggered warheads for cellular disruption.

Example 4: Genetically Expressed GVs Enable Cells to Undergo Inertial Cavitation This example was carried out to test another application of biomolecular cavitation using GVs: triggered cavitation of intracellular GVs in engineered bacteria, leading to cell lysis and payload release.

In addition to their use as purified protein nanostructures, GVs can be expressed inside engineered cells, as shown recently in *E. coli* Nissle 1917 and *S. typhimurium* using a hybrid GV-encoding gene cluster[22]. It is therefore hypothesized that bacterial cells expressing GVs could be triggered to undergo intracellular bubble formation and cavitation under low frequency ultrasound, resulting in cellular lysis and the release of a co-expressed protein payload (FIG. 17A, panel a).

To test this concept, a 14-gene operon was engineered combining GV-encoding genes GvpA-GvpU from the ARG1 gene cluster[22] with a gene encoding the luminescent NanoLuc protein as a model releasable payload (FIG. 17A, panel b). This construct was transformed into *S. typhimurium* SL1344 (see Bacterial expression experiments section above for details), which has been used in multiple experimental bacterial therapies[2,3]. Cells transformed with this gene cluster produced abundant cytoplasmic GVs, as confirmed with optical phase microscopy (FIG. 17A, panel c). To test whether the GV-expressing bacteria could serve as sources of inertial cavitation, wide-band acoustic emissions from cell suspensions exposed to focused ultrasound were measured. Since it was previously shown that ARG1 GVs have a relatively high collapse pressure[22], a lower ultrasound frequency of 300 kHz was used in these experiments to ensure efficient collapse of the heterologously expressed GVs at achievable pressure levels. In response to 300 kHz ultrasound pulses, the GV-expressing *S. typhimurium* emitted a high level of wide-band signals, increasing with the peak negative pressure (FIG. 17B, panel d). Similar activity was not observed in control cells expressing just NanoLuc.

Next, the lysis of GV-expressing cells in response to focused ultrasound was examined and the release of their co-expressed protein payload was measured. In an assay comparing the number of colonies formed on agar plates by cells that were exposed to ultrasound to cells that were not, it was found that significantly fewer colonies were produced by GV-expressing *S. typhimurium* cells following ultrasound exposure, compared to equivalent experiment with NanoLuc controls (FIG. 17B, panel e). The bioluminescence of the media, corresponding to payload release, was also significantly elevated in GV-expressing cells exposed to ultrasound compared to controls (FIG. 17C, panel f, two-way ANOVA analysis: percentage of variation attributed to the interaction is 20.46% with p=0.0001, n=6). Taken together, these results suggest that GV-expressing engineered cells can serve as ultrasound-triggered cellular "explosives", releasing proteins into their surroundings in response to a remote trigger.

To demonstrate acoustic detonation in mammalian cells, focused ultrasound was applied to HEK293T cells genetically engineered to express GVs in response to chemical induction [Ref: Farhadi, A., Ho, G. H., Sawyer, D. P., Bourdeau, R. W. & Shapiro, M. G. Ultrasound imaging of gene expression in mammalian cells. *Science* (80-.). 365, 1469-1475 (2019)] (FIG. 17C, panel g), comparing induced cells to uninduced controls (see Mammalian expression and experiments section above for details). Ultrasound exposure resulted in cell lysis, as observed by counting cells labeled with a positive cell death marker using flow cytometry (FIG. 17C, panel h). This lysis was highly specific to GV-expressing cells, with 8.32% dead compared to 0.522% of controls. The partial lysis of detonated cells is attributed to the relatively small quantity of GVs produced by mammalian cells compared to bacteria using existing genetic constructs (FIG. 19) [Ref: Farhadi, A., Ho, G. H., Sawyer, D. P., Bourdeau, R. W. & Shapiro, M. G. Ultrasound imaging of gene expression in mammalian cells. *Science* (80-.). 365, 1469-1475 (2019)], and is expected to be improved in the future with additional genetic engineering.

Example 5: In Vivo Use of GVs as Cavitation Nuclei

After establishing GVs as biomolecular and cellular cavitation nuclei in vitro and in cellulo as shown in the other examples, the ability of GVs to nucleate cavitation in vivo was tested in a mouse tumor xenograft. Details on the in vivo testing can be found in In vivo passive cavitation detection section of the general procedure above.

A 3D-printed holder was developed to co-align the foci of both the focused transducer and the imaging transducer at the center of the tumor (FIG. 18A, panel a), with a needle guide incorporated to facilitate precise injections into the tumor core. This setup enabled one to perform ultrasound-guided-ultrasound-therapy experiments, in which images of the GVs inside the tumor were acquired and PCD measurements at the injection site were performed. Adult BALB/c mice were injected in the flanks with two MC26 tumors, one in each side. After the tumors reached diameters of 6-10 mm, ultrasound-guided GV injections and cavitation were performed. Using anatomical ultrasound scans to observe the tumor boundaries and select the injection point (FIG. 18A, panel b, left), one tumor was injected in each mouse with purified GVs and the contralateral tumor was injected with saline as a vehicle control. To facilitate GV imaging *Anabaena* GVs were used in which GvpC has been removed[18], allowing them to produce non-linear ultrasound signals easily distinguishable from background using an amplitude modulation pulse sequence[21] (FIG. 18A, panel b, middle). FUS was applied to the tumors before and after GV or saline injection, while recording PCD signals. Strong broadband signals representing inertial cavitation were only detectable in GV-injected tumors (FIG. 18B, panels c-d). After FUS exposure, the contrast from injected GVs disappeared after focused ultrasound exposure, confirming their collapse (FIG. 18A, panel b, right). These results confirm that GVs can serve as biomolecular cavitation nuclei in the context of a disease-relevant living tissue.

To demonstrate the mechanical effect of GV detonation on in vivo tissue, GVs were administered intravenously to mice for uptake by the liver. This organ was chosen for its relatively homogenous, well-perfused tissue with minimal background necrosis. In addition, GVs naturally accumulate in the liver after intravenous injection [Ref: Shapiro, M. G. et al. Biogenic gas nanostructures as ultrasonic molecular reporters. *Nat. Nanotechnol.* 9, 311-6 (2014).; Le Floc'h, J. et al. In vivo Biodistribution of Radiolabeled Acoustic Protein Nanostructures. *Mol. Imaging Biol.* 20, 230-239 (2018)]. Details on how this experiment was carried out can be found in Cavitation effect on liver tissue in vivo section of the general procedure above.

In particular, engineered Ana GVs were injected into the tail vein and their uptake by the liver was monitored using nonlinear ultrasound. (FIG. 18C, panel e). FUS was then applied, spatially targeting the medial lobe. Following ultrasound exposure, liver tissue was collected for histological analysis. Color-unmixed images of hematoxylin and eosin (H&E)-stained sections revealed necrosis and blood extravasation specifically in the FUS-targeted lobe in mice injected with GVs (FIG. 18C, panel f) Such tissue damage which was virtually absent in regions not targeted with ultrasound and in saline-injected controls (FIG. 18C, panels g-h). These results confirm the capacity of systemically delivered GVs to produce mechanical tissue disruption upon spatiotemporal triggering with ultrasound.

Example 6: Gas Vesicle Expression in Bacteria and Mammalian Cells

Gas vesicles were expressed as indicated in the materials and method in *S. typhimurium* cells (Bacterial expression experiments) and in $HEK_{293T}$ cells (Mammalian expression experiments). See Example 4.

The imaging was performed as indicated in the materials and methods (in vivo ultrasound imaging of GV expressing cells. The results are illustrated in FIG. 19 and in particular in FIG. 19 Panel (a) the ultrasound images of agarose phantoms containing *S. typhimurium* cells gas expressing vesicle are shown, taken after a pressure ramp. The initial amplitude modulation (AM) frame shows the echo from collapsing gas vesicles (left, Peak US,), and the second one presents the residual signal from the cells after bubble dissolution (middle, Collapsed). The gas vesicle specific signal, calculated as the difference between these two images, reveals high gas vesicle content in bacteria (right, Difference).

In FIG. 19 Panel (b) the ultrasound images of agarose phantoms containing gas vesicle expressing $HEK_{293T}$ cells are shown. The partial volume occupied by gas vesicle in mammalian cell is much lower than in bacteria, resulting in lower differential signal in the right image.

Example 7: Effects of GV Cavitation on Surrounding Tissue

The results of Example 5 are shown in FIG. 20. In particular histologic stains of liver samples were collected after systemic saline injection followed by FUS exposure (negative control, FIG. 20 a-d) or GV injection and sonication (FIG. 20 e-h).

Color deconvolution was applied to H&E stains of liver sections (a, e) to create separate red blood cell (FIG. 20 b, f) and tissue (FIG. 20 c, g) images. The residual un-mixed images are presented in (FIG. 20 d, h). Necrotic regions in the H&E images (FIG. 20 a, zoom-in in i) were found around hemorrhagic foci (FIG. 20 c, zoom-in in j) in the livers of mice injected with gas vesicles following focused ultrasound exposure. Scale bar is 2 mm (FIG. 20 d, h), 200 µm (FIG. 20 j).

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and arrangements to additional gas vesicles, related components, genetic or chemical variants, as well as in compositions, methods and systems herein described, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Milenic, D. E., Brady, E. D. & Brechbiel, M. W. Antibody-Targeted Radiation Cancer Therapy. 3, (2004).
2. Din, M. O. et al. Synchronized cycles of bacterial lysis for in vivo delivery. *Nature* 536, 81-85 (2016).
3. Danino, T. et al. Programmable probiotics for non-invasive urinary detection of cancer. *Sci. Transl. Med.* 7, 1-36 (2015).
4. Kotula, J. W. et al. Programmable bacteria detect and record an environmental signal in the mammalian gut. *Proc. Natl. Acad. Sci.* 111, 4838-4843 (2014).
5. Archer, E. J., Robinson, A. B. & Süel, G. M. Engineered *E. coli* that detect and respond to gut inflammation through nitric oxide sensing. *ACS Synth. Biol.* 1, 451-457 (2012).
6. Claesen, J. & Fischbach, M. A. Synthetic microbes as drug delivery systems. *ACS Synth. Biol.* 4, 358-364 (2015).
7. Daniel, C., Roussel, Y., Kleerebezem, M. & Pot, B. Recombinant lactic acid bacteria as mucosal biotherapeutic agents. *Trends Biotechnol.* 29, 499-508 (2011).
8. Steidler, L. et al. Treatment of Murine Colitis by *Lactococcus* Secreting Interleukin-10. *Adv. Sci.* 289, 1352-1355 (2011).
9. Davila, M. L. et al. Efficacy and Toxicity Management of 19-28z CAR T Cell Therapy in B Cell Acute Lymphoblastic Leukemia. 6, (2014).
10. Jackson, H. J., Rafiq, S. & Brentjens, R. J. Driving CAR T-cells forward. *Nat. Publ. Gr.* 13, 370-383 (2016).
11. Piraner, D. I. et al. Going Deeper: Biomolecular Tools for Acoustic and Magnetic Imaging and Control of Cellular Function. (2017). doi:10.1021/acs.biochem.7b00443
12. Rev, A. et al. Biomolecular Ultrasound and Sonogenetics. (2018).
13. Shapiro, M. G. et al. Biogenic gas nanostructures as ultrasonic molecular reporters. *Nat. Nanotechnol.* 9, 311-6 (2014).
14. Lu, G. J. et al. imaging of gas-filled protein nanostructures. *Nat. Mater.* 17, (2018).
15. Pfeifer, F. Distribution, formation and regulation of gas vesicles. *Nat. Rev. Microbiol.* 10, 705-715 (2012).
16. Walsby, A. E. Gas Vesicles. *Annu. Rev. Plant Physiol.* 26, 427-439 (1975).
17. Shapiro, M. G. et al. xenon magnetic resonance imaging. *Nat. Chem.* (2014). doi:10.1038/nchem.1934
18. Lakshmanan, A. et al. Molecular Engineering of Acoustic Protein Nanostructures. *ACS Nano* 10, 7314-7322 (2016).
19. Kunth, M., Lu, G. J., Witte, C., Shapiro, M. G. & Schro, L. Protein Nanostructures Produce Self-Adjusting Hyperpolarized Magnetic Resonance Imaging Contrast through Physical Gas Partitioning. (2018). doi:10.1021/acsnano.8b04222
20. Maresca, D., Sawyer, D. P., Renaud, G., Lee-gosselin, A. & Shapiro, M. G. Nonlinear X-Wave Ultrasound Imaging of Acoustic Biomolecules. *Phys. Rev. X* 8, 41002 (2018).
21. Maresca, D. et al. Nonlinear ultrasound imaging of nanoscale acoustic biomolecules Nonlinear ultrasound imaging of nanoscale acoustic biomolecules. 073704, (2017).
22. Bourdeau, R. W. et al. Acoustic reporter genes for noninvasive imaging of microorganisms in mammalian hosts. *Nature* 553, 86-90 (2018).
23. Kwan, J. J. et al. Ultrasound-Propelled Nanocups for Drug Delivery. *Small* 11, 5305-5314 (2015).
24. Coussios, C. C. & Roy, R. A. Applications of Acoustics and Cavitation to Noninvasive Therapy and Drug Delivery. (2008). doi:10.1146/annurev.fluid.40.111406.102116
25. Holland, C. K. & Apfel, R. E. An Improved Theory for the Prediction of Microcavitation Thresholds. 204-208 (1989).
26. Church, C. C. & Church, C. C. Frequency, pulse length, and the mechanical index. 162, 1-8 (2007).
27. Cherin, E. et al. Acoustic behavior of *Halobacterium salinarum* gas vesicles in the high-frequency range: experiments and modeling. *Ultrasound Med. Biol.* 43, 1016-1030 (2017).
28. Walsby, A. E. The pressure relationships of gas vacuoles. *Proc. R. Soc. London. Ser. B. Biol. Sci.* 178, 301-326 (1971).
29. Lakshmanan, A. et al. Preparation of biogenic gas vesicle nanostructures for use as contrast agents for ultrasound and MRI. *Nat. Protoc.* 12, 2050-2080 (2017).
30. Häcker, G., Redecke, V. & Häcker, H. Activation of the immune system by bacterial CpG-DNA. *Immunology* 105, 245-251 (2002).
31. Dang, L. H., Bettegowda, C., Huso, D. L., Kinzler, K. W. & Vogelstein, B. Combination bacteriolytic therapy for the treatment of experimental tumors. *Proc. Natl. Acad. Sci. U.S.A.* 98, 15155-60 (2001).
32. Ryan, R. M. et al. Bacterial delivery of a novel cytolysin to hypoxic areas of solid tumors. *Gene Ther.* 16, 329-339 (2009).
33. Forbes, N. S., Munn, L. L., Fukumura, D. & Jain, R. K. Sparse initial entrapment of systemically injected *Salmonella typhimurium* leads to heterogeneous accumulation within tumors. *Cancer Res.* 63, 5188-5193 (2003).
34. Cobbold, R. S. *Foundations of biomedical ultrasound*. (Oxford University Press, 2006).
35. Zhang, H. F., Maslov, K., Sivaramakrishnan, M., Stoica, G. & Wang, L. V. Imaging of hemoglobin oxygen satu- 36. Beard, P. Biomedical photoacoustic imaging. *Interface Focus* 1, 602-631 (2011).
37. Jang, M. J. & Nam, Y. NeuroCa: integrated framework for systematic analysis of spatiotemporal neuronal activity patterns from large-scale optical recording data. *Neurophotonics* 2, 035003 (2015).
38. Schneider, C. a, Rasband, W. S. & Eliceiri, K. W. NIH Image to ImageJ: 25 years of image analysis. *Nat. Methods* 9, 671-675 (2012).

The invention claimed is:

1. An ultrasound pressure-based method comprising:
   delivering a gas vesicle (GV) to a target site, the GV having a GV type collapse threshold pressure;
   setting an ultrasound generation system to produce ultrasound pulses having a positive pressure set above the GV type collapse threshold pressure and a negative pressure; and
   applying the ultrasound pulses to the target site, thus:
   collapsing the GV by the positive pressure of the ultrasound pulses, thereby forming gas bubbles; and
   driving cavitation of the gas bubbles by the negative pressure.

2. The method of claim 1, further comprising imaging the target site before applying the ultrasound pulses.

3. The method of claim 2, wherein the imaging comprises one of ultrasound imaging or MRI.

4. The method of claim 3, wherein the imaging comprising using the GV as a contrast agent.

5. The method of claim 2, further comprising imaging the target site after applying the ultrasound pulses.

6. The method of claim 1, wherein the ultrasound pulses are applied with a center frequency no greater than 2.5 MHz.

7. The method of claim 6, wherein the ultrasound pulses have a mechanical index above 0.12.

8. The method of claim 7, wherein the ultrasound pulses have a mechanical index above 2.8.

9. The method of claim 1, wherein the GV is a plurality of GVs.

10. A method of applying a mechanical stress to a cavitation target in a target site, the method comprising:
    delivering to the target site containing the cavitation target one or more gas vesicles (GVs) having a GV type collapse threshold, the delivering positioning the GVs in proximity of the cavitation target, and
    applying ultrasound pulses to the target site after the delivering, the ultrasound pulses having a positive pressure set above the GV type collapse threshold pressure and a negative pressure and being selected to both collapse the GV type and to, by the negative pressure, cavitate bubbles created by the GVs after collapse, the cavitated bubbles applying the mechanical stress to the cavitation target.

11. The method of claim 10, wherein the cavitation target is an inorganic target.

12. The method of claim 10, wherein the mechanical stress is selected from the group consisting of destroying, damaging, pushing, pinching, propelling, mixing, and deforming.

13. The method of claim 10, further comprising imaging the target site at a first time to verify delivery of the GVs at the target site and imaging the target site at a second time to verify an effect of the cavitating of the bubbles.

14. The method of claim 1, being a method of lysing a target cell of a target tissue at the target site, further comprising lysing the target cell by the cavitated bubbles.

15. The method of claim 1, wherein the ultrasound pulse has a center frequency selected to be less than 2.5 MHz.

16. The method of claim 15, wherein the GV are functionalized to attach to tissue at the target site.

17. The method of claim 15, wherein the delivering the GV to tissue at the target site comprises expressing the GV in a delivery cell that is delivered to the target tissue.

18. The method of claim 15, wherein the GV contains a payload compound that has a therapeutic effect on tissue at the target site.

19. The method of claim 1, wherein the delivering the GV to the target site comprises delivering a delivery cell containing the GV, and wherein cavitated bubbles lyse a target cell by lysing the delivery cell.

20. The method of claim 19, wherein the delivery cell expresses the GV.

21. The method of claim 19, wherein the delivery cell contains a hybrid cluster.

22. The method of claim 1, being a method of delivering a payload compound to a target tissue at the target site, wherein the delivering the GV to the target site comprises delivering a delivering cell configured to express the payload compound, the delivering performed for a time and under conditions allowing expression of the GV in the delivery cell, and wherein the cavitated bubbles lyse the delivery cell and deliver the target compound to the target tissue.

23. The method of claim 22, wherein the target compound is a protein expressed by the delivery cell.

24. The method of claim 22, wherein the allowing the expression of the GV in the delivery cell occurs before the delivering the delivery cell.

25. The method of claim 22, further comprising ultrasound imaging or MRI imaging the delivery cell at the target site.

26. The method of claim 22, wherein the target compound is a therapeutic substance.

27. The method of claim 1, wherein the ultrasound pulses have at least one of: a duty cycle above 0.2% or a mechanical index above 2.8.

* * * * *